(12) United States Patent
Shah et al.

(10) Patent No.: US 12,201,598 B2
(45) Date of Patent: Jan. 21, 2025

(54) IMMUNOREGULATORY MICROPARTICLES FOR MODULATING INFLAMMATORY ARTHRITIDES

(71) Applicant: The Regents of the University of California, Oakland, CA (US)

(72) Inventors: Nisarg Shah, San Diego, CA (US); David A. McBride, San Diego, CA (US); Nunzio Bottini, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 18/474,108

(22) Filed: Sep. 25, 2023

(65) Prior Publication Data
US 2024/0033242 A1   Feb. 1, 2024

Related U.S. Application Data

(63) Continuation of application No. PCT/US2022/021966, filed on Mar. 25, 2022.

(60) Provisional application No. 63/166,873, filed on Mar. 26, 2021.

(51) Int. Cl.
| | | |
|---|---|---|
| *A61K 31/203* | (2006.01) | |
| *A61K 9/00* | (2006.01) | |
| *A61K 9/50* | (2006.01) | |
| *A61P 19/02* | (2006.01) | |

(52) U.S. Cl.
CPC .......... *A61K 31/203* (2013.01); *A61K 9/0019* (2013.01); *A61K 9/5031* (2013.01); *A61P 19/02* (2018.01)

(58) Field of Classification Search
CPC ..... A61P 19/02; A61K 31/203; A61K 9/0019; A61K 9/5031
See application file for complete search history.

(56) References Cited

U.S. PATENT DOCUMENTS

| | | |
|---|---|---|
| 2013/0236509 A1 | 9/2013 | Van Noort |
| 2017/0182068 A1 | 6/2017 | Bodick et al. |
| 2018/0064666 A1 | 3/2018 | Lu et al. |

FOREIGN PATENT DOCUMENTS

CN   107929263 A   4/2018

OTHER PUBLICATIONS

Makadia et al. Polymers (Basel), 2011, 3(3), p. 1377-1397. (Year: 2011).*
PCT International Search Report and Written Opinion for PCT/US2022/021966, mailed, Jun. 27, 2022, (19 pages.).
Liu et al., The role of all-trans retinoic acid in the biology of Foxp3+ regulatory T cells, Cell Mol Immunol, Feb. 2, 2015, vol. 12(5), pp. 553-557, [retrieved on Jun. 1, 2022].
Bakdash et al., Retinoic acid primes human dendritic cells to induce gut-homing, IL-10 producing regulatory T cells, Mucosal Immunology, Jul. 16, 2014, vol. 8, pp. 265-278, [retrieved on Jun. 1, 2022].
Lu et al., Critical role of all-trans retinoic acid in stabilizing human natural regulatory T cells under inflammatory conditions, Proc Natl Acad Sci USA, Aug. 6, 2014, vol. 111 (33), pp. E3432-E3440, [retrieved on Jun. 2, 2022].
Wang et al., Retinoic acid enhances the production of IL-10 while reducing the synthesis of IL-12 and TNF-alpha from LPS-stimulated monocytes/macrophages, J Clin Immunol, Jan. 26, 2007, vol. 27(2), pp. 193-200, [retrieved on Jun. 6, 2022].
Duriancik et al., Vitamin A as a Regulator of Antigen Presenting Cells. The Journal of Nutrition, Jun. 16, 2010, vol. 140(8), pp. 1395-1399, [retrieved on Jun. 6, 2022].
Mosquera et al., All-Trans Retinoic Acid Inhibits Migration and Invasiveness of Rheumatoid Fibroblast-Like Synoviocytes, J Pharmacol Exp Ther, Feb. 29, 2020, vol. 372, pp. 185-192, [retrieved on Jun. 6, 2022].
Neumann et al., Biodegradable poly (L-lactic acid) (PLLA) and PLLA-3-arm blend membranes: The use of PLLA-3-arm as a plasticizer, Polymer Testing, Mar. 16, 2017, vol. 60, pp. 84-93, [retrieved on May 31, 2022].

* cited by examiner

*Primary Examiner* — Kara R McMillian
(74) *Attorney, Agent, or Firm* — Eversheds-Sutherland (US) LLP

(57) ABSTRACT

Described herein are compositions and methods for treating inflammatory arthritic conditions that are effective systemically without causing generalized immunosuppression when administered locally into an inflammatory arthritis-affected joint or a draining lymph node of the arthritis-affected joint of a patient.

20 Claims, 40 Drawing Sheets

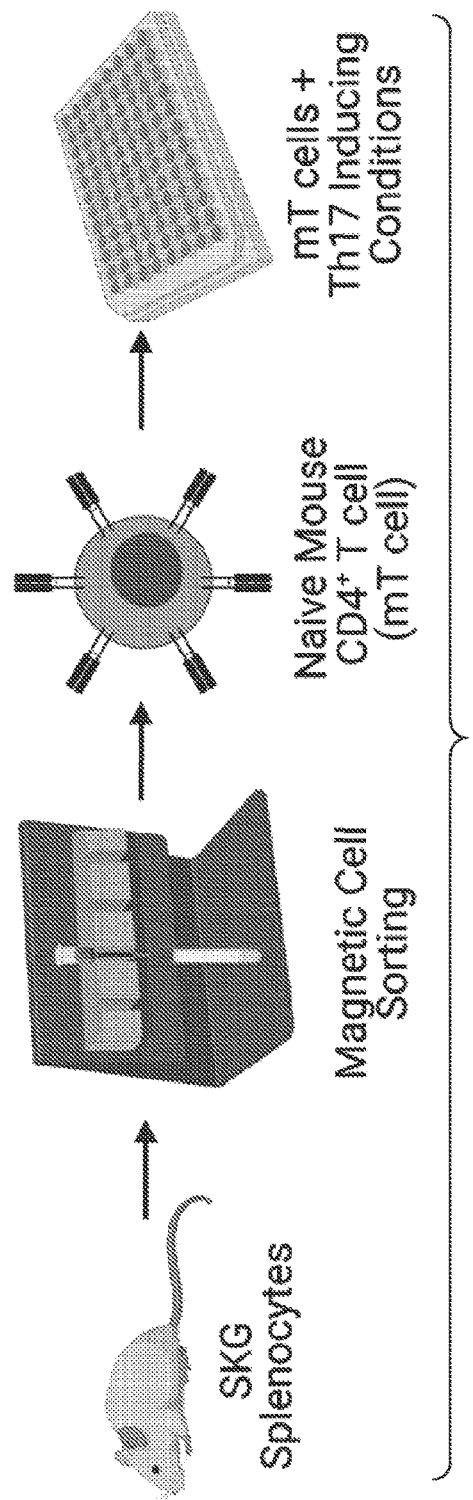
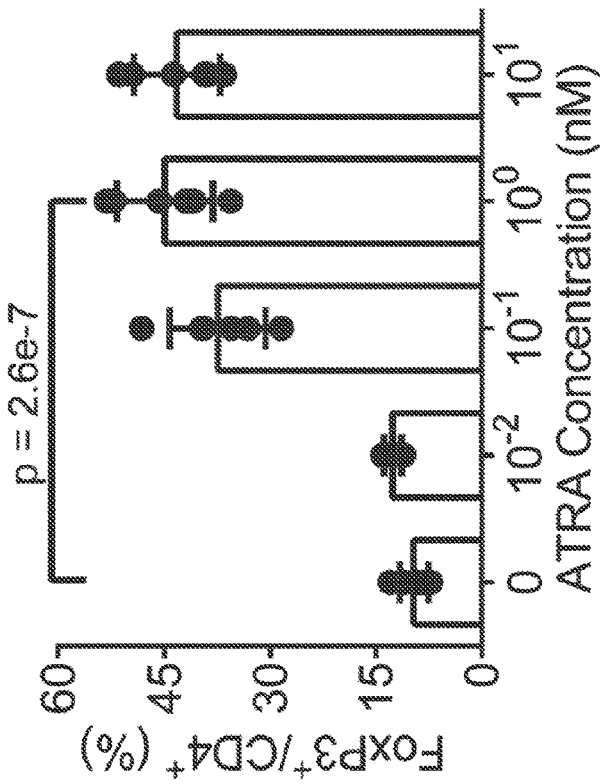
Fig. 1A
Fig. 1B

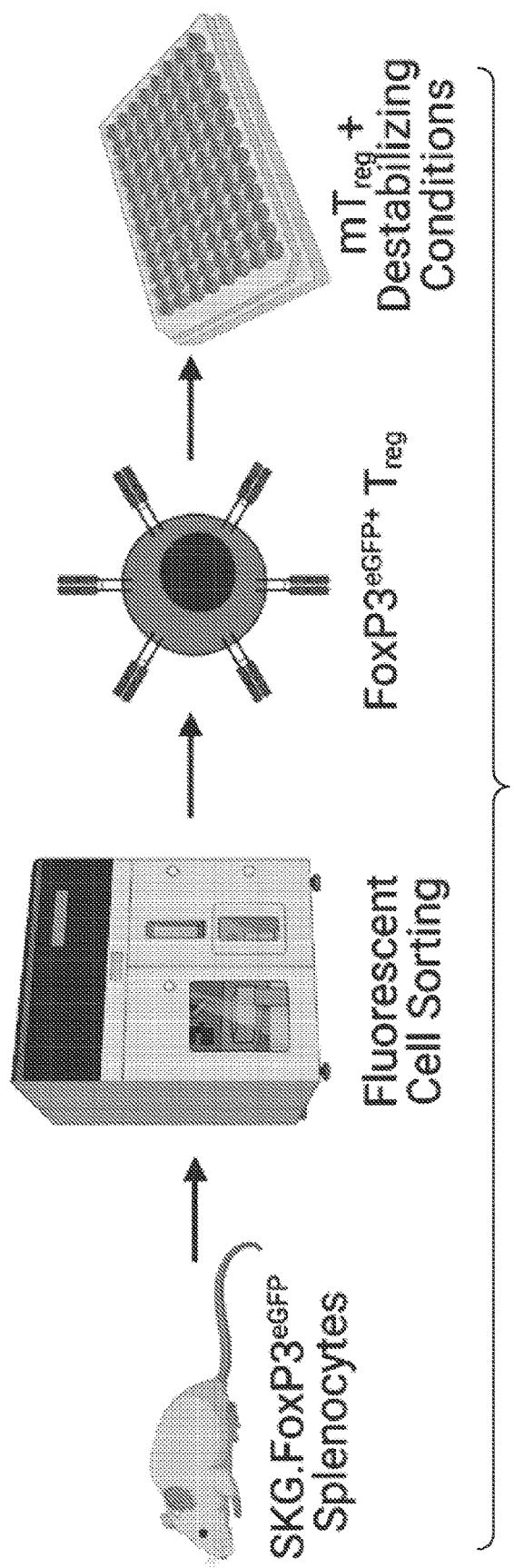
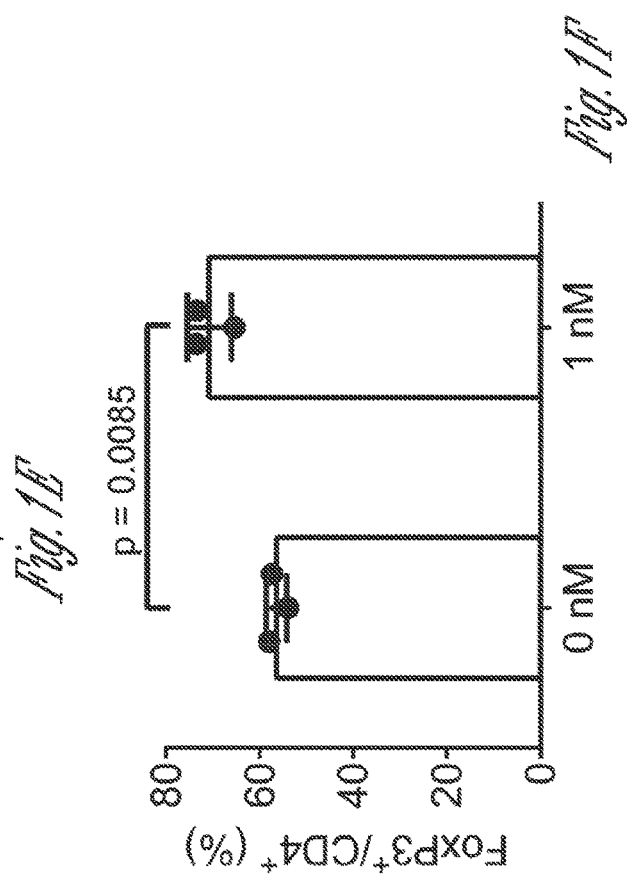
Fig. 1E
Fig. 1F $$(1)\ \frac{dC_1}{dt} = -k_{12}C_1 + k_{21}C_2 z - k_e C_1$$

$$(2)\ \frac{dC_2}{dt} = \frac{k_{12}C_1}{z} - k_{21}C_2 + \frac{dm_{MP}(t)}{dt}\frac{1}{V_2}$$

| Parameter | $k_{12}$ | $k_{21}$ | $k_e$ | $V_2$ | $z$ |
|---|---|---|---|---|---|
| Value | 0.2 h⁻¹ | 0.2 h⁻¹ | 0.84 h⁻¹ | 20 µL | 0.0013 |

Fig. 4B

| | $C_{max,1}$ | $t_{max,1}$ |
|---|---|---|
| 10.6 µm | 16 pM | 133 hr |
| | $C_{max,2}$ | $t_{max,2}$ |
| | 130 nM | 123 hr |

| | $C_{max,1}$ | $t_{max,1}$ |
|---|---|---|
| 6.5 µm | 40 pM | 87 hr |
| | $C_{max,2}$ | $t_{max,2}$ |
| | 146 nM | 97 hr |

| | $C_{max,1}$ | $t_{max,1}$ |
|---|---|---|
| 3.9 µm | 20 pM | 124 hr |
| | $C_{max,2}$ | $t_{max,2}$ |
| | 162 nM | 119 hr |

Fig. 4E

IMMUNOREGULATORY MICROPARTICLES FOR MODULATING INFLAMMATORY ARTHRITIDES

CROSS REFERENCE TO RELATED APPLICATIONS

This application is a continuation of PCT Application No. PCT/US2022/021966, filed Mar. 25, 2022, which claims the priority of U.S. provisional application Ser. No. 63/166,873, filed Mar. 26, 2021, the disclosure of which is incorporated herein by reference in its entirety.

FEDERAL FUNDING

This invention was made with government support under F31AR079921, T32AR064194, T32CA153915, P30AR073761, R03DE031009, P30CA23100, and UL1TR001442 awarded by the National Institutes of Health and ECCS-2025752 awarded by the National Science Foundation. The government has certain rights in the invention.

BACKGROUND

Inflammatory arthritides affect millions of people worldwide. These conditions cause swelling and both acute and chronic joint pain. Inflammatory arthritides lower the quality of life and are a leading cause of disability. Inflammatory arthritis describes many conditions that locally and systemically affect joints, tissues around the joints, and other connective tissues. Rheumatoid Arthritis (RA), Psoriatic arthritis, and ankylosing spondylitis are the most common forms of inflammatory arthritis. Other forms of the disease include osteoarthritis, childhood arthritis, fibromyalgia, gout, and lupus.

Rheumatoid arthritis (RA) is a form of autoimmune inflammatory arthritis characterized by systemic inflammation of the joints. Systemic inflammation associated with RA also causes damage to other tissues and organs such as the skin, eyes, lungs, heart, and blood vessels. RA-affected joints are infiltrated with immune cells, including hyperactivated pathogenic CD4+ T cells which produce pro-inflammatory mediators. For example, in moderate to severe RA, polyclonal CD4+ T cells with reactivity against multiple cartilage extracellular matrix epitopes have been isolated in the peripheral blood and synovium. These hyperactivated immune cells produce pro-inflammatory cytokines that contribute to the structural damage of joints, causing pain, swelling, bone erosion, and joint deformity.

Conventional medications for inflammatory arthritis include painkillers, steroids, and nonsteroidal anti-inflammatory drugs. Conventional disease modifying anti-rheumatic drugs (DMARDs) that cause generalized immunosuppression such as methotrexate and sulfasalazine have also greatly improved the prognosis of inflammatory arthritis such as RA. Biologic DMARDs such as tumor necrosis factor inhibitors (e.g. etanercept), interleukin-6 inhibitors (e.g. tocilizumab), and interleukin-1 receptor antagonist (e.g. anakinra), and janus kinase inhibitors (e.g. tofacitinib) target specific mediators of inflammation including pro-inflammatory cytokines and their receptors. However, all the above medications operate through non-specific immunosuppression and increase the risk of opportunistic and serious infections, cancer and reduce the effectiveness towards vaccines. Urinary tract infections and upper respiratory infections are common side effects from immunosuppressive medications. More serious effects of immunologic disruption can include pneumonia, cellulitis, diverticulitis, and acute pyelonephritis. Current DMARDs also fail to induce RA remission in over 30% of patients. Therefore, a need exists for agents that can modulate the immune system to reduce inflammatory arthritis symptoms and tissue damage with minimal to null generalized immunosuppression.

SUMMARY

Compositions and methods are described herein that are useful for the treatment of inflammatory arthritides by immunomodulation that is effective systemically without causing generalized immunosuppression. The compositions and methods include use of biodegradable microparticles (MPs) comprising an immunomodulatory agent delivered by intra-articular injection directly into an inflammatory arthritis-affected joint or associated draining lymph nodes, local subcutaneous tissue, or the joint capsule of the inflammatory arthritis-affected joint. The MPs provides for the sustained or extended localized release of an immunomodulatory agent encapsulated or bound to the MPs for a time sufficient to reduce inflammation or structural joint damage in the inflammatory arthritis-affected joint and at least one other inflammatory arthritis-affected joint that was not directly treated.

Inflammatory arthritis-affected joints, such as in RA-affected joints, are infiltrated with immune cells, including hyperactivated pathogenic CD4+ T cells which produce pro-inflammatory mediators. For example, in moderate to severe RA, polyclonal CD4+ T cells with reactivity against multiple cartilage extracellular matrix epitopes have been isolated in the peripheral blood and synovium. Joint-infiltrating CD4+ T cells comprise pathogenic T helper (Th), which are pro-inflammatory, and disease protective T cells expressing FoxP3, called regulatory T cells ($T_{reg}$). $T_{reg}$ cells generally suppress inflammatory T cells. However, in response to pathogenic inflammation, $T_{reg}$ cells can lose immunoregulatory function and convert to an "ex$T_{reg}$ cell" phenotype which produce pro-inflammatory cytokines, such as interleukin (IL)-17. A numerical imbalance between $T_{reg}$ cells and autoreactive pro-inflammatory CD4+ T cell subsets, including retinoic acid receptor-related orphan receptor gamma (RORγ)t-expressing Th17 cells, and impaired $T_{reg}$ cell function due to the presence of ex$T_{reg}$ cells in chronically inflamed joints and draining lymph nodes are major contributors to the pathogenesis of RA.

The RA disease process, similar to human RA is modeled well in the Sakaguchi (SKG) mouse model. SKG mice develop spontaneous Tb17-dependent arthritis. The onset of arthritis can be accelerated by fungal component injections. SKG mouse arthritis exhibits symmetric involvement of joints, positivity for rheumatoid factor, anti-citrullinated peptide antibodies, elevation of key RA cytokines including IL-6, IL-1 and tumor necrosis factor (TNF), cartilage and bone destruction and reduced bone density similar to human RA. The SKG mouse model of RA simulates the insufficient $T_{reg}$ cell function and $T_{reg}$ cell stability described in many patients with RA. SKG mouse $T_{reg}$ cells co-transferred with SKG CD4+ T cells into immunodeficient recombination activating gene 2 (Rag2-KO) mice inhibit disease development. The SKG $T_{reg}$ cells also downregulate FoxP3 and convert to pathogenic IL-17+ ex$T_{reg}$ in arthritic joints and draining lymph nodes.

Compositions and methods described herein provide an immunomodulatory agent delivered by intra-articular (IA) injection into the inflammatory arthritis-affected joint or its associated draining lymph nodes, local subcutaneous tissue, or the joint capsule. The immunomodulatory agent delivered through these routes induces local expansion and stabilization of $T_{reg}$ cells and the production of anti-inflammatory cytokines in the inflammatory arthritis-affected joint. In addition to promoting local immunomodulation, recirculation of expanded and stabilized $T_{reg}$ cells and associated anti-inflammatory cytokines results in systemic amelioration of arthritis severity with minimal systemic immunosuppression. The local release of the immunomodulatory agent encapsulated in the IA administered MPs stimulates local expansion and stabilization of disease protective $T_{reg}$ cells. Since these disease protective $T_{reg}$ cells, as well as pathogenic T cells can recirculate systemically throughout immune organs, locally expanded and stabilized $T_{reg}$ cells can suppress joint specific autoimmunity systemically without suppressing local and systemic non-joint-specific immune responses.

Therefore, described herein are MPs encapsulating an immunomodulatory agent that induces the systemic expansion and stabilization of arthritis-protective $T_{reg}$ cells without systemic immunosuppression. For example, a high affinity retinoic acid receptor (RAR) agonist that induces arthritis-protective $T_{reg}$ cells can be encapsulated in the MPs. The RAR agonist can include all-trans retinoic acid (ATRA), which has been demonstrated to induce disease protective $T_{reg}$ cells after systemic administration. The MPs may comprise any suitable biodegradable or bioabsorbable polymer. For example the MPs may comprise a poly (D,L-lactide-co-glycolide), including poly-(lactic-co-glycolic) acid (PLGA) to generate RAR agonist-encapsulated PLGA MPs. Intra-articular injection directly into an inflammatory arthritis-affected joint or associated draining lymph nodes, local subcutaneous tissue, or the joint capsule of ATRA-encapsulated PLGA MPs that provides localized, sustained release of the RAR agonist. For example, the RAR agonist ATRA enhances differentiation of naïve SKG mouse and human T cells into $T_{reg}$ cells and stabilizes SKG mouse and human $T_{reg}$ cells in inflammatory Th17 polarizing conditions. The ATRA-encapsulated PLGA MPs are retained in inflammatory arthritis-affected joints or associated draining lymph nodes, local subcutaneous tissue, or the joint capsule after local injection.

The ATRA encapsulated PLGA MPs provide sustained or extended release of bioactive ATRA, for a time sufficient to reduce inflammation, reduce bone loss, enhance $T_{reg}$ cells in the injected joint or associated draining lymph nodes, local subcutaneous tissue, or the joint capsule, and improves arthritis symptoms systemically without evidence of non-specific suppression of T cell-dependent immune responses. For example, the biodegradable MPs can sustain a continuous release of the $T_{reg}$-inducer in the inflammatory arthritis-affected joint of the patient for at least 21 days. The biodegradable MPs can also sustain a continuous release of the $T_{reg}$-inducer in the inflammatory arthritis-affected joint of the patient for approximately three months.

Methods are also described herein that involve administration to a patient suffering from inflammatory arthritis, or suspected to have subclinical inflammatory arthritis, a composition that includes a DMARD with the encapsulated immunomodulatory agent MPs. The encapsulated immunomodulatory agent MP is administered to the patient through local injection into the inflammatory arthritis-affect joint or its draining lymph nodes, subcutaneously near the joint, or into the joint's capsule. The DMARD may be administered orally, subcutaneously, or intravenously to the patient. Examples of inflammatory arthritis that can be treated include, psoriatic arthritis, RA, ankylosing spondylitis, osteoarthritis, juvenile arthritis, fibromyalgia, gout, or lupus.

DESCRIPTION OF THE FIGURES

FIGS. 1A-H illustrate that all-trans retinoic acid (ATRA) differentially promotes $T_{reg}$ cell enhancement and Th17 suppression in a dose dependent manner. FIG. 1A schematically illustrates an in vitro experiment to assess the effect of ATRA on TH17 and $T_{reg}$ cell differentiation from naïve CD4+ mouse T (mT) cells in Th17 inducing conditions. FIG. 1B illustrates the quantification of FoxP3 expression in CD4+ mT cells differentiated in Th17 inducing conditions with concentrations of ATRA between 0-10 nM. FIG. 1C illustrates the quantification of IL-17 expression in CD4+ mT cells differentiated in Th17 inducing conditions with concentrations of ATRA between 0-10 nM. FIG. 1D illustrates the quantification of RORγt expression in CD4+ mT cells differentiated in Th17 inducing conditions with concentrations of ATRA between 0-10 nM. FIG. 1E schematically illustrates a $T_{reg}$ cell destabilization experiment in model inflammatory conditions. FIG. 1F illustrates the quantification of FoxP3 expression in $T_{reg}$ cells following a destabilization assay with or without 1 nM ATRA. FIG. 1G illustrates quantification of IL-17 expression in $T_{reg}$ cells following a destabilization assay with or without 1 nM ATRA. FIG. 1H illustrates the quantification of RORγt expression in $T_{reg}$ cells following a destabilization assay with or without 1 nM ATRA Data in FIGS. 1B-D and F-H are the mean±S.D. of representative experiments and were performed in three experimental replicates. Statistical analyses in FIGS. 1B-D and F-H were performed using unpaired Student's two tailed t-tests.

FIG. 2A is a schematic depicting the steps for the synthesis of 50:50 poly-(lactic-co-glycolic) ATRA microparticles (referred to as ATRA-encapsulated PLGA MPs or PLGA-ATRA MPs) FIGS. 2B, D, and F depict scanning electron micrographs (SEMs) of ATRA-encapsulated PLGA MPs homogenized at varying speeds to produce particles with average MPs diameters of 10.6, 6.5, and 3.9 μm, respectively. Averages displayed in FIGS. 2B, D. and F represent the average volume averaged diameters across three batches per particle size. FIGS. 2C, E, and G depict the ATRA-encapsulated PLGA MPs size distribution within a single representative batch for each homogenization speed, including the volume averaged size and standard deviation. FIG. 2C depicts the ATRA-encapsulated PLGA MPs size distribution for particles with a volume average of MPs diameters of 9.6 μm. FIG. 2E depicts the ATRA-encapsulated PLGA MPs size distribution for particles with volume average MPs diameters of 6.3 μm. FIG. 2G depicts the ATRA-encapsulated PLGA MPs size distribution for particles with volume average MPs diameters of 3.9 μm. FIG. 2H depicts the release profile of ATRA from 10 mg of ATRA-encapsulated PLGA MPs with a volume average of 10.6 μm ATRA-encapsulated PLGA MPs, 6.5 μm ATRA-encapsulated PLGA MPs, or 3.19 μm ATRA-encapsulated PLGA MPs in 1 mL of release solution over 28 days. FIG. 2I depicts the efficacy of ATRA released from ATRA-encapsulated PLGA MPs formulations at various timepoints in the CD4+ mT cell Th17 differentiation assay depicted in FIG. 1A. FIG. 2J depicts the efficacy of ATRA released from ATRA-encapsulated PLGA MPs formulations at various timepoints in the CD4+ mT cell destabilization assay described in FIG. 1E. FIG. 2K depicts the efficacy of ATRA released from ATRA-encapsulated PLGA MPs formulations at various timepoints in CD4+ human hT cell differentiation assays. Concentrations of diluted supernatants as measured by nanodrop are shown beneath the timepoint. Diameter averages in FIGS. 2B, D and F are based on analysis of three batches per size; data in FIGS. 2C, E and G are distributions and diameter averages from a single batch for each size, compiled from analysis of three different image sections per size; FIG. 2C was performed for two additional batches for each size and similar results were obtained; data in FIGS. 2H-K are the mean±S.D. of representative experiments; FIG. 2H represents data from three separate release replicates performed a single batch of particles for each size; FIGS. 2I and J were performed twice: FIG. 2K was performed twice with two independent donors. Statistical analysis in FIG. 2H was performed by comparing the area under the curve for each replicate using an unpaired Student's two tailed t-test, *=<0.05. **=<0.01; analyses in FIG. 2I-K were performed using unpaired Student's two tailed t-test.

FIG. 3A is a schematic depicting the experimental set up assessing the efficacy of ATRA-encapsulated PLGA MPs in treating mid-stage arthritis and retention of the ATRA-encapsulated PLGA MPs at the injection site. FIG. 3B depicts the quantification of fluorescent signal from intra-articular (IA) injected Cy5-tagged PLGA-Blank MPs using an in vivo imaging system (IVIS) to track particle residence and degradation. FIGS. C-F depict the quantification of arthritis progression in mice treated with either 2 µg ATRA-encapsulated PLGA MPS or mice injected IA with dose-matched bolus ATRA. Quantification includes comparison of aggregate clinical scores as shown in FIG. 3C, comparison of clinical scores of ipsilateral and contralateral hind paws as shown in FIG. 3D, aggregate ankle thickness of hind paws as shown in FIG. 3E, and a comparison of ankle thickness of ipsilateral and contralateral hind paws as shown in FIG. 3F. FIG. 3G depicts disease progression by clinical score of arthritis in SKG mice injected with mannan on day 0 to synchronize arthritis onset, and treated on day 14 with either 2 µg 35 ATRA-encapsulated PLGA MPs or control unloaded PLGA-Blank MPs. FIG. 3H depicts the aggregate clinical scoring of hind paws that received treatment (ipsilateral) vs hind paws that received sham PBS injection (contralateral). FIG. 3I depicts the quantification of arthritis progression using hind ankle thickness in SKG mice. FIG. 3M depicts a Comparison of ankle thickness between ipsilateral and contralateral ankles in treated and control mice. Data in FIG. 3B are the mean±S.D. of normalized radiant efficiency of Cy5-tagged PLGA-Blank MPs in n=9 mice; data in FIGS. C-J are the mean±SEM; FIGS. C-F (n=5 mice for ATRA-encapsulated PLGA MPs, n=5 mice for bolus IA ATRA) and FIGS. G-J (n=10 mice for ATRA-encapsulated PLGA MPs, n=11 mice for PLGA-Blank MPs) represent data from a single experiment performed with sets of littermate mice: Statistical analyses in FIG. 3B were performed using an unpaired Student's two-tailed t-test; statistical analyses in FIGS. C-J were performed using a linear mixed-effects model.

FIGS. 4A-E. Shows modeling of ATRA-encapsulated PLGA MPs pharmacokinetics in vivo. FIG. 4A is a Schematic of two-compartment pharmacokinetic model depicting release of ATRA from ATRA-encapsulated PLGA MPs, transfer of ATRA between the synovium and peripheral blood, and elimination of ATRA from the peripheral blood via the kidneys. FIG. 4B depicts the governing differential equations for the model compartments and parameter values for first order model coefficients. FIG. 4C depicts the model-computed concentration profiles in the peripheral blood based on in vitro release profiles of 10.6 µm, 6.5 µm, and 3.9 µm ATRA-encapsulated PLGA MPs. FIG. 4D depicts model-computed concentration profiles of ATRA in the synovial fluid. FIG. 4E depicts the maximum concentration ($C_{max}$) and the time at which it occurs ($t_{max}$) values for the release profiles. Data in FIGS. 4C-E represent model outputs using the parameters depicted and the average ATRA release profile determined in vitro.

FIG. 5A-B depicts representative hematoxylin and eosin (H&E) staining of ankles from SKG mice with mannan-induced arthritis treated with either PLGA-Blank MPs or ATRA-encapsulated PLGA MPs demonstrating immune cell infiltration (immune cells shown at arrows). FIG. 5C depicts quantification of ankle inflammation by immune cell infiltration via automated histomorphometric analysis of aggregate ankle data. FIG. 5D depicts quantification of ankle inflammation by immune cell infiltration via automated histomorphometric analysis of aggregate ipsilateral (ipsi) vs contralateral (contra) ankle data. FIG. 5E-F depict representative safranin-O staining showing bone erosion and proteoglycan loss of the talus/tibia junction (shown at arrows). FIG. 5G depicts quantification of proteoglycan loss as aggregate scores. FIG. 5F depicts quantification of proteoglycan loss as ipsilateral vs contralateral scores. Images in FIGS. 5A-B and FIGS. 5E-F are representative images; data in FIGS. 5C, D, G, and H represent the mean±S.D. Histology is from mice represented in clinical and immunological data in FIG. 3 and FIG. 4. Aggregate data were taken from n=7 mice for the PLGA-Blank MPs data and n=4 mice from the ATRA-encapsulated PLGA MPs data. Statistical analysis in FIG. 5C was performed using an unpaired Student's two-tailed t-test; statistical analyses in FIG. 5D were performed using unpaired Student's two-tailed test between treatment groups and paired Student's two-tailed t-test between ipsilateral and contralateral groups within the same treatment group; statistical analysis in FIG. 5G was performed using a Mann-Whitney test; statistical analyses in FIG. 5H were performed using Mann-Whitney test between treatment groups and Wilcoxon test between ipsilateral and contralateral groups within the same treatment group. FIGS. 5I-J depict quantification of bone erosion in the hind paws of mice treated with PLGA-Blank MPs or ATRA-encapsulated PLGA MPs demonstrating the chondroprotective effects of ATRA-encapsulated PLGA MPs. FIG. 5I displays aggregate bone erosion scoring of both hind paws, while FIG. 5 displays the scores disaggregated by the directly treated ipsilateral hind paw or the untreated contralateral hind paw, demonstrating that chondroprotection is observed in both the treated joint and the untreated joint in mice treated with ATRA-encapsulated PLGA MPs.

FIG. 6A depicts the clinical scores from mice treated with either PLGA-Blank MPs or ATRA-encapsulated PLGA MPs at 2, 20, or 200 µg doses. Data for 2 µg ATRA-encapsulated PLGA MPs and PLGA-Blank MPs are the same data in FIG. 3, shown here and in FIGS. 6B and 6D for comparison to alternate doses. FIG. 6B depicts the change in ankle thickness of arthritic SKG mice injected with mannan and treated on day 14 with either 2 µg ATRA-encapsulated PLGA MPs or control blank PLGA (PLGA-Blank) microparticles. FIG. 6C depicts the aggregate clinical scores of hind paws that were directly treated (ipsilateral) or contralateral to treatment from mice treated on day 14 with either 2, 20, or 200 μg ATRA-encapsulated PLGA MPs or PLGA-Blank MPs. Data for groups in FIGS. 6A-C, were powered as follows: PLGA-Blank (n=11), ATRA-encapsulated PLGA MPs 200 μg (n=5), ATRA-encapsulated PLGA MPs 20 μg (n=3), ATRA-encapsulated PLGA MPs 2 μg (n=10). ****indicates p<0.0001. Statistical analyses for FIGS. 6A-C were performed using a linear mixed effects model. Differences between ipsilateral and contralateral scores in b and c were not significant.

FIG. 7A is a schematic showing the induction of arthritis in fate-mapping mice and subsequent treatment and endpoint. FIG. 7B-D depict the quantification of IL-17 expression by tdTomato$^+$CD4+ T cells isolated from the spleen (shown in FIG. 7B), draining lymph nodes (shown in FIG. 7C), or ankles (shown in FIG. 7D) of fate-mapping mice. Paired points represent littermates, wherein one littermate was treated IA with PLGA-Blank MPs, and the other littermate was treated IA with ATRA-encapsulated PLGA MPs.

FIG. 8B depicts the clinical scores of SKG mice with arthritis treated with either PLGA-Blank MPs (n=2) or ATRA-encapsulated PLGA MPs (n=3). Immunization with OVA did not impact clinical score progression in either cohort in comparison to previous trials with arthritic SKG mice. FIG. 8C depicts log 10 of anti-OVA IgG1 titers from a titer assay measured at OD405=0.3 both immediately before booster immunization and 10 days after booster immunization. FIG. 8D is a schematic depicting an OVA vaccination assay in healthy C57B1/6 mice. FIG. 8E depicts log 10 of anti-OVA IgG1 titers from a titer assay measured at OD405=0.3. FIG. 8F depicts Tetramer+CD4+ T cell counts from processed mouse splenocytes 20 days after initial immunization with OVA. Data in FIG. 8B represent the mean±SEM for PLGA-Blank MPs treated (n=2) and ATRA-encapsulated PLGA MPs treated (n=3) mice, data in FIGS. 8C, E. and F represent the mean±S.D. of n=2, n=5, and n=5 biological replicates, respectively. Statistical analyses in FIGS. 8C, E, and F were performed using an unpaired Student's two-tailed t-test.

FIGS. 9A-B depicts the clinical score of SKG mice injected subcutaneously between the scapula of ATRA-encapsulated PLGA MPs, dose-matched Bolus of ATRA in corn oil, and vehicle alone (corn oil). Neither bolus ATRA nor ATRA-encapsulated PLGA MPs provided improvement in clinical score (FIG. 9A) or ankle swelling (FIG. 9B).

FIG. 10A depicts the quantification of FOXP3 expression in CD4+ T cells after 24-hour pretreatment with either nothing (None), 1 nM ATRA (ATRA), or IL-2, followed by removal and washing of the cells, and transfer to Th17 inducing conditions. FIG. 10B depicts quantification of IL-17 expression in CD4+ T cells after a 24-hour pretreatment with either nothing (None), 1 nM ATRA (ATRA), or IL-2, followed by removal and washing of the cells, and transfer to Th17 inducing conditions.

FIG. 11A depicts the quantification of the counts per peak of the three groupings of differentially accessible regions (DARs) (Common, Th17 Control>ATRA Treated, ATRA Treated>Th17 Control) showing the spread in the differences in counts per peak of the different regions. FIG. 11B depicts the quantification of DARs by counts per peak between cells cultured in Th17 inducing conditions with (ATRA Treated) or without (Th17 Control) 1 nM ATRA. FIG. 11C is a heatmap of all DARs grouped in rows by those enriched in the ATRA treated group or those enriched in the Th17 Control group. Heatmapping was performed by determining the z-score of the DAR in a given sample as compared to the row. FIG. 11D depicts a Genome browser plot for Th17 and $T_{reg}$ associated genes.

DETAILED DESCRIPTION

Figure 1C:
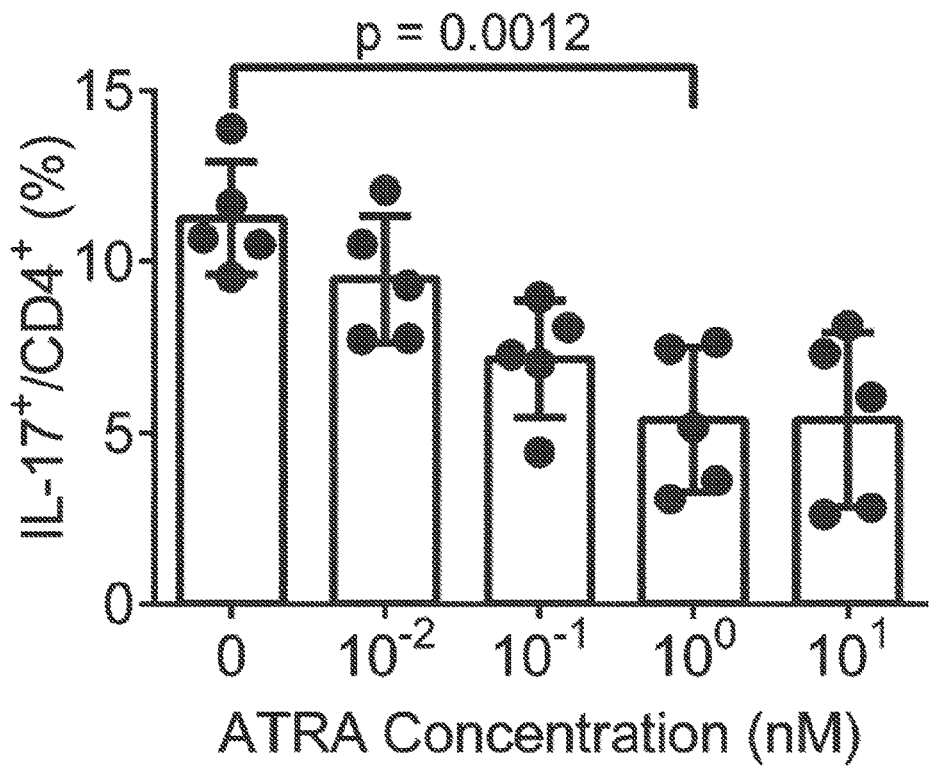

Compositions and methods are described herein that are useful for treating inflammatory arthritis in a patient. The compositions described herein can be administered to treat subjects, such as animals or humans, in need of such treatment, or who can develop a need for such treatment. For example, the compositions can reduce the incidence and severity of immune system-related disorders or diseases. Examples of immune system-related disorders or diseases that can be treated include inflammatory arthritis conditions such as psoriatic arthritis, rheumatoid arthritis (RA), ankylosing spondylitis, osteoarthritis, childhood arthritis, fibromyalgia, gout, and lupus. The patient can be treated when their joints are not actively inflamed by inflammatory arthritis, such as when the patient is in remission, to reduce the severity or prevent recurrence. The patient can also be treated when they are in a pre-symptomatic phase of inflammatory arthritis to reduce the severity or prevent the further development or onset of the disease.

Methods for treating inflammatory arthritis in a patient may comprise local administration of an immunomodulatory agent MP into at least one of an inflammatory arthritis-affected joint, a draining lymph node of the inflammatory arthritis-affected joint, a subcutaneous tissue in the vicinity of the inflammatory arthritis-affected joint, or a joint capsule of the inflammatory arthritis-affected joint of the patient. The immunomodulatory agent may comprise any composition that modifies the microenvironment in the inflammatory arthritis-affected joint and systemically affects at least one other inflamed joint without causing generalized systemic immunosuppression. For example, the immunomodulatory agent can modify the microenvironment by reducing bone erosion, inflammation, and reducing cartilage damage. The agent can also modulate the immune microenvironment of the joint by reducing the amount of pro-inflammatory cytokines or chemokines, increasing anti-inflammatory cytokines, or modulate the role of various immune cells such as B-cells, T-cells, and macrophages in inflammation.

Immunomodulatory Agent

The immunomodulatory agent can comprise a regulatory $T_{reg}$-inducer, a synovial fibroblast modulator, or an antigen presenting cell modulator that is at least partially encapsulated in a biodegradable material. The $T_{reg}$-inducer can induce FOXP3 expression in naïve CD4+ T cells. The $T_{reg}$-inducer can comprise a retinoic acid receptor (RAR)

agonist. The RAR agonist can comprise all trans retinoic acid (ATRA). The immunomodulatory agent may also induce IL-10 expression in naïve CD4+ T cells.

The immunomodulatory agent can comprise a disease modifying anti-rheumatic drug (DMARD), wherein the DMARD is encapsulated within the biodegradable material. The DMARD can also be excluded from the at least partially encapsulated immunomodulatory agent and can instead be administered to the patient orally, subcutaneously, or intravenously separately and concurrently with administering the at least partially encapsulated immunomodulatory agent to the patient. Treating the patient with a combination of the $T_{reg}$-inducer and DMARD can synergistically reduce inflammation or bone loss in the inflammatory arthritis-affected joint.

The immunomodulatory agent can not include TGF-β either encapsulated in the MPs or attached to the surface of the MPs. TGF-β is known to induce non-specific $T_{reg}$ expansion which leads to generalized immunosuppression. Moreover, intra-articular TGF-β injection has been demonstrated to induce inflammation, synovial hyperplasia, osteophyte formation and can exacerbate an inflamed joint. Intra-articular TGF-β injection has also been demonstrated to accelerate the onset of inflammatory arthritis, whereas local inhibition of TGF-β has been shown to improve $T_{reg}$/Th17 balance.

MPs Comprising an Immunomodulatory Agent

MPs comprising the immunomodulatory agent can be administered by intraarticular injection (TA) into an inflammatory arthritis-affected joint to reduce the severity of inflammation. Encapsulation of the immunomodulatory agent can facilitate sustained release of the immunomodulatory agent at therapeutically relevant concentrations to suppress disease progression in only the treated joint not in the untreated joints. Recirculation of immunomodulatory agent expanded and stabilized $T_{reg}$ cells and associated anti-inflammatory cytokines are responsible for the systemic suppression on disease progression in non-injected joints.

For example, the regulatory T cell ($T_{reg}$)-inducer, such as ATRA, at least partially encapsulated in a biodegradable microparticle, such as ATRA-encapsulated PLGA MPs, can stabilize a population of Tug cells within the inflammatory arthritis-affected joint and at least one other inflamed joint when the composition is administered into at least one of the inflammatory arthritis-affected joint directly by intra-articular injection, the draining lymph node of the inflammatory arthritis-affected joint, a subcutaneous tissue in the vicinity of the inflammatory arthritis-affected joint, or a joint capsule of the inflammatory arthritis-affected joint of the patient. Stabilizing the population of $T_{reg}$ cells within the inflamed joint can include increasing a ratio of $T_{reg}$ cells to dysfunctional $T_{reg}$ cells. The dysfunctional $T_{reg}$ cells can include pro-inflammatory $T_{reg}$ phenotype T cells. The dysfunctional $T_{reg}$ cells can also include Th17-like $exT_{reg}$ phenotype T cells or Th1-like $exT_{reg}$ phenotype T cells. ATRA-encapsulated PLGA MPs treatment can also enhance a systemic production of anti-inflammatory cytokines in the patient.

ATRA-encapsulated PLGA MPs can be administered by intra-articular injection (IA) into an inflammatory arthritis-affected joint reducing inflammation severity in SKG mice. This correlates with enhancing anti-inflammatory $T_{reg}$ cells over pro-inflammatory Th17 cells. The ATRA encapsulated MPs promote the differentiation of mouse and human $T_{reg}$ cells, prevented mouse $T_{reg}$ cell destabilization, and inhibit Th17 cells. Although bolus injection of ATRA in solution can deliver ATRA directly to the joint, associated lymph nodes and soft tissues, this method of injection has little to no effect on arthritis progression. This is likely due to inability to maintain adequate concentrations of ATRA to expand and stabilize $T_{reg}$ cells due to the rapid clearance of injected ATRA solution from the joint, lymph nodes and associated soft tissues. In contrast, encapsulating ATRA in injected PLGA-based MPs facilitates sustained release of ATRA at therapeutically relevant concentrations to suppress disease progression for at least four (4) weeks post-injection. IA ATRA-encapsulated PLGA MPs reduced arthritis severity in SKG mice and stabilized clinical scores in both treated and untreated joints.

Consistent with disease modulation, end-point histological evaluations in both the ipsilateral ankle joints that received IA treatment and contralateral joints that received sham IA injections demonstrated a reduction in fifteen (15) distinct types of infiltrating immune cells, bone erosions and proteoglycan loss. These results indicate that ATRA-encapsulated MPs, in addition to reducing inflammation, also act as a systemic disease-modifying agent in SKG arthritis. Based on these results, the locally injected IA-based immunomodulatory agent encapsulated polymer MP approach described herein demonstrated both local and systemic therapeutic efficacy. This approach is distinct from IA steroid injections which are used in some RA patients, to temporarily reduce inflammation in individual joints that fail to respond to systemically delivered DMARDs.

ATRA encapsulated PLGA MPs can equally affect ipsilateral-injected and contralateral-uninjected joints in the same patient. Systemic disease modulation using this method may not be associated with generalized suppression of T cell-dependent immune responses. Rather, the enhancement of $T_{reg}$ cells over Th17 cells in the ankles and draining lymph nodes of ATRA encapsulated PLGA MPs treated SKG mice demonstrates local enhancement of $T_{reg}$ cells and systemic recirculation of these cells and associated anti-inflammatory cytokines improves arthritis regression. This finding is also consistent with the observation that enhanced numbers of $exT_{reg}$ cells increase arthritis severity in the SKG mouse arthritis model. A administration of ATRA encapsulated PLGA MPs in SKG mice improved $T_{reg}$ cell stability limiting the conversion of $T_{reg}$ cells to $exT_{reg}$ cells.

The number of capillaries and capillary permeability can increase in RA joints. This results in rapid clearance of injected therapies, especially low molecular weight compounds like ATRA in solution, from the RA affected joints. As IA injections can only be administered safely to the patient with limited frequency, rapid clearance of injected drugs in solution cannot be overcome simply by increasing the frequency of drug administration. Increasing the concentration of injected drugs in solution can result in prolonged joint exposure to the drug. However elevated injected drug concentrations can cause local toxicity within the joint. Rapid release of large concentrations of injected drug can also cause undesired side effects if taken up by off-target tissues after exit from the joint. In contrast, ATRA-encapsulated PLGA MPs can provide release of sustained or extended release of local concentrations of ATRA, which can reduce the severity of inflammation or bone loss in the inflammatory arthritis-affected joint and at least one other inflammatory arthritis-affected joint of the patient into which the composition was not directly administered. The release profile of ATRA from IA administered ATRA-encapsulated PLGA MPs is insufficient to cause systemic ATRA exposure above an immunosuppressive threshold.

The therapeutic efficacy of locally administered ATRA-encapsulated PLGA MPs can be more therapeutically efficacious than systemic treatment with DMARDs in SKG mice. The improvement in arthritis scores by IA ATRA-encapsulated PLGA MPs can be superior to the reported efficacy of methotrexate, a first line conventional DMARD, in SKG mice. This can be despite the administration of a 1.0 mg/kg daily dose that is ~20-fold greater than the typical clinically administered dose in humans. The efficacy of IA ATRA-encapsulated PLGA MPs can be comparable systemic administration of biologic DMARDs such as weekly 100 μg anti-IL-17 antibody treatment in SKG mice or weekly 200 μg anti-IL-6R antibody. Since ATRA-encapsulated PLGA MPs are not associated with generalized suppression of T cell dependent immune responses, they could also serve as an immunoregulatory adjuvant to administration of currently approved DMARDs for enhancing disease control without further impairing the protective immune response.

The improvement in clinical and histomorphometrical evaluations in SKG mice treated with IA ATRA-encapsulated PLGA MPs can correlate with improved $T_{reg}$ cell to Th17-like $exT_{reg}$ phenotype cell ratio or $T_{reg}$ to Th1-like $exT_{reg}$ phenotype T cell ratio. For example, following IA injection of ATRA-encapsulated PLGA MPs, $T_{reg}$ cell populations can be enhanced over Th17-like $exT_{reg}$ phenotype cells in the ipsilateral ankle within 3 days, and by 21 days post-treatment. This enhancement can be observed locally, such as in the draining lymph nodes of both ankles, but cannot be observed in the spleen. These results are consistent with data from fate mapping SKG mice, in which $T_{reg}$ cell stability in joint-draining lymph nodes appeared to be enhanced 11 days following IA injection of ATRA-encapsulated PLGA MPs. Together with the in vitro enhancement of $T_{reg}$ cell function mediated by ATRA, these results demonstrate that systemic disease-specific immunomodulation can be attributed to recirculation of $T_{reg}$ cells from the treated joint, rather than systemic immunosuppression by ATRA.

The IA ATRA-encapsulated PLGA MPs can be distinct from other preclinical immunoregulatory strategies being evaluated in autoimmune inflammatory arthritis such as antigen-specific immunomodulation using tolerogenic vaccines in collagen-induced arthritis (CIA) mice, ex vivo generation and 17 infusion of tolerogenic $T_{reg}$-inducing dendritic cells by incubation with a mixture of RA autoantigens (Rheumavax) and ex vivo generation and infusion of a chimeric antigen receptor (CAR)-$T_{reg}$ against one or multiple RA autoantigens. The efficacy of Rheumavax and CAR-$T_{reg}$ cell approaches can be limited by the paucity of known autoantigens that can be targeted as substantial antigenic spread is known to occur in RA.

ATRA-encapsulated PLGA MPs can have the advantage of acting locally at the site of inflammation to promote disease specific $T_{reg}$ cells without a priori knowledge of the participating epitopes. ATRA-encapsulated PLGA MPs can durably suppress inflammatory arthritis disease progression in treated mice, without immunosuppression of T cell-mediated immune responses. ATRA-encapsulated PLGA MPs can be equally effective at suppressing disease progression after a single IA injection into the inflammatory arthritis-affected joint at a dose ranging from 2-200 μg. This ATRA dose is significantly lower than frequent systemically administered ATRA doses ranging from 0.5-25 mg/kg, used in other autoimmune disease mouse models modulating inflammation in uveitis, experimental autoimmune encephalomyelitis, and inflammatory autoimmune arthritis. For example, ATRA-encapsulated PLGA MPs can be effective at suppressing disease progression after a single IA injection into the inflammatory arthritis-affected joint at a dose ranging from 2-20 μg.

The calculated maximum systemic exposure to ATRA in vivo after a single IA ATRA-encapsulated PLGA MPs injection ($C_{max}$) is 40 pM, which can be well below the concentrations reached with doses that have been associated with toxicity in rodents (>14 mg/kg). The pharmacokinetic model described herein predicted a therapeutically efficacious concentration of ATRA in the synovial fluid of the treated inflammatory arthritis-affected joint and a non-immunosuppressive systemic concentration.

Inflammatory arthritis can lead to chronic pain and disability. While DMARDs have transformed disease management, a large fraction of patients continue to struggle to achieve remission. Deepening immunosuppression in patients who are only partially responsive to specific DMARDs, for example by combining a second DMARD, is not currently a viable option. The ability to modulate pathogenic immune cells to delay clinical disease progression, coupled with preservation of cartilage proteoglycan (PG) and reduced bone erosion (BE), supports the utility of IA ATRA-encapsulated PLGA MPs as a locally delivered agent that provides a systemic disease-specific clinical benefit without generalized immunosuppression.

ATRA-encapsulated PLGA MPs mediated local immunomodulation, when administered early in the development of inflammatory arthritis such as RA. This result supports the use of ATRA-encapsulated PLGA MPs as an effective monotherapy to slow or prevent progression of disease. Periodical injections of ATRA-encapsulated PLGA MPs can serve as an immunoregulatory adjuvant in combination with currently approved DMARDs to enhance control of disease without further impairing the immune response to infections and cancer. ATRA-encapsulated PLGA MPs can be lyophilized and stored for extended periods and potentially be used off-the-shelf. In addition, the temperature stability of small molecule therapeutics like ATRA compared to less temperature stable antibodies offers the ability for more economically preferable room temperature storage compared to refrigerated storage. ATRA-encapsulated PLGA MPs injections into the inflammatory arthritis-affected joint can be performed under fluoroscopic and ultrasound guidance techniques if needed. Importantly, systemically delivered ATRA has been reported to be chondroprotective in CIA mice and in models of osteoarthritis (OA). In addition, systemic administration of ATRA does not cause musculoskeletal symptoms. Taken together, these results indicate ATRA can be well-tolerated and safe for IA delivery.

Biodegradable/Bioresorbable Polymer

The immunomodulatory agents described herein can be at least partially encapsulated in a biodegradable/bioresorbable material that can comprise an agent that delays absorption. Prolonged absorption of injectable compositions can be brought about by including in the composition an agent which delays absorption, for example, monostearate salts and gelatin. Moreover, the compounds described herein can be formulated in a time release formulation, for example in a composition that includes a slow-release polymer. The composition can be prepared with carriers that will protect the immunomodulatory agent from rapid release, such as a controlled release formulation, including implants and microencapsulated delivery systems.

The polymer comprised in the microparticles described herein be any suitable biodegradable polymer. Non-limiting examples of polymers include poly(caprolactone) (PCL), ethylene vinyl acetate polymer (EVA), poly(lactic acid)

(PLA), poly(L-lactic acid) (PLLA), poly(glycolic acid) (PGA), poly(lactic-co-glycolic acid)(PLGA). PLGA-poly(ethylene glycol) block copolymer; poly(L-lactic-T-glycolic acid) (PLLGA), poly(D,L-lactide) (PDLA), poly(D,L-lactide-co-caprolactone) (PDLA), poly(D,L-lactide-co-caprolactone-co-caprolactone), poly(D,L-lactide-co-caprolactone-co-glycolide), poly(D,L-lactide-co-PPO-co-D,L-lactide), poly(D,L-lactide-co-PPO-co-D,L-lactide), polyhydroxylalcanoates, poly(hydroxybutyrate) (P4HB), poly-L-lysine (PLL), poly-L-glutamic acid, poly(hydroxy acids), polyanhydrides, poly(ester amides), polyamides, poly(ester ethers), polycarbonates, polyphosphates, polyphosphoesters, polyphosphazines, polydioxazones, polyurethanes, derivatized celluloses such as alkyl celluloses, hydroxyalkyl celluloses, cellulose ethers, cellulose esters, nitro celluloses, carboxymethylcellulose, polyvinylalcohols, polyaminoacids, poly(butyric acid), poly(valeric acid), poly(levulinic acid), and combinations of one or more of the aforementioned polymers or block-copolymers of two or more of the aforementioned polymers.

For example, the polymer can be PLGA. The lactic acid:glycolic acid ratio in a PLGA polymer is from about 50:50 to about 99:1 (e.g., from about 75.25 to about 90:10; about 70:30 to about 90:10; about or from about 80:20 to about 90:10; about 85:15 to about 75:25; about 85:15; or about 75:25). In some embodiments, the PLGA can have a weight average molecular weight (MW) of from about 20 kDa to about 1000 kDa (e.g., from about 50 kDa to about 500 kDa; about 100 kDa to about 300 kDa; or about 150 kDa to about 250 kDa. The PLGA can have a polydispersity index no greater than 3, no greater than 2.5, no greater than 2, or even no greater than about 1.8. In some embodiments the polymer has a glass transition temperature from about 25° C. to about 65° C., from about 30° C. to about 55° C., or from about 35° C. to about 50° C.

Alternatively, the polymer can be PLA. The PLA can have a weight average molecular weight (MW) of from about 20 kDa to about 1000 kDa (e.g., from about 40 kDa to about 500 kDa; about 60 kDa to about 300 kDa; or about 80 kDa to about 250 kDa. In some embodiments, the PLA can have a polydispersity index no greater than 3, no greater than 2.5, no greater than 2, or even no greater than about 1.8.

Multi-block copolymers are also contemplated herein, including triblock copolymers of the biodegradable/bioresorbable polymers described herein.

In other examples, the polymer is PLA/PLGA block copolymer. The PLA/PLGA block copolymer can have a weight average molecular weight (MW) of from about 10 kDa to about 300 kDa, about 20 kDa to about 200 kDa. or about 40 kDa to about 100 kDa. In some embodiments, the PLA/PLGA block copolymer can have a polydispersity index no greater than 3, no greater than 2.5, no greater than 2, or even no greater than about 1.8.

Blends of two or more polymers described herein are also contemplated. For example, blends of PLA and PLGA are contemplated, where the PLA is blended with the PLGA or the PLGA is blended with the PLA in about a range of ratios including 15:85, 25:75, 50:50, etc. For example, blends of PCL and PLGA are contemplated, where the PCL is blended with the PLGA or the PLGA is blended with the PLA in about a range of ratios including 15:85, 25:75, 50:50, etc.

Extended-release formulations can include one or more biodegradable polymers described herein for specific tuning of release and degradation characteristics. The biodegradable/bioresorbable polymers can be in any form including uncapped polymers, wherein the termini are carboxylic acid termini; or capped polymers wherein the termini are partially or even fully capped as esters (e.g., as $(C_1-C_6)$alkyl esters, such as methyl, ethyl, propyl and butyl esters; $(C_6-C_{14})$aryl-$(C_1-C_6)$alkyl esters, such as benzyl and napthylmethyl esters; and combinations thereof). The $(C_1-C_6)$alkyl and/or the $(C_6-C_{14})$aryl portions of the cap can be substituted with one or more groups such as —$NR^1R^2$ groups, where $R^1$ and $R^2$ are independently selected from H, $(C_1-C_6)$alkyl, $(C_6-C_{14})$aryl, and $(C_6-C_{14})$aryl-$(C_1-C_6)$alkyl groups. The $(C_1-C_6)$alkyl and/or the $(C_6-C_{14})$aryl portions of the cap can be substituted with one or more groups such as —$OR^1$ groups, where $R^1$ is selected from H, $(C_1-C_6)$alkyl, $(C_6-C_{14})$aryl, and $(C_6-C_{14})$aryl-$(C_1-C_6)$alkyl groups.

The polymer can include an amphiphilic block copolymer. In additional specific embodiments, the polymer can include a copolymer of lactic acid and glycolic acid (e.g., PLGA). In additional specific embodiments, the polymer can include at least one of PLGA-block-PEG and PLGA. In block copolymers of PLGA and PEG, the PEG block can have a molecular weight of from about 500 Da to about 40,000 Da (e.g., from about 1,000 Da to about 20,000 Da; or about 2.000 Da to about 10,000 Da.

Biodegradable/bioresorbable polymers also include polylactic acid-co-caprolactone, polyethylene glycol, polyethylene oxide, poly lactic acid-block-poly ethylene glycol, poly glycolic acid-block-poly ethylene glycol, poly lactide-co-glycolide-block-poly ethylene glycol, poly ethylene glycol-block-lipid, polyvinyl pyrrolidone, poly vinyl alcohol, a glycosaminoglycan, polyorthoesters, polysaccharides, polysaccharide derivatives, polyhyaluronic acid, polyalginic acid, chitin, chitosan, chitosan derivatives, cellulose, hydroxyethylcellulose, polypeptides, polylysine, polyglutamic acid, albumin, polyhydroxy alkonoates, polyhydroxy valerate, polyhydroxy butyrate, proteins, polyphosphate esters, lipids, and mixtures thereof.

The MPs employed herein have a suitable and appropriate dimension. In some examples, the microparticles can be oval, spherical, elliptical, tubular, etc. In addition to the shape, the MPs will have a suitable diameter to provide the MPs with resistance to phagocytosis by macrophages or escape from the inflammatory arthritis-affected joint or the draining lymph node that the MPs were directly administered into. For example, the MPs may have an average diameter of approximately 5 μm up to approximately 20 μm. In another example, the MPs can have a particle diameter of approximately 20 μm up to approximately 50 μm.

In addition, the MPs will have a particle size distribution, which can be quantified by a "D value." The term "D50," as used herein refers, to the 50th percentile number- or volume-based median particle diameter, which is the diameter below which 50% by number or volume of the particle population is found. Other percentages such as D10 (10%), D90 (90%), D99 and D100 (100%) are also commonly used. The term "D99," as used herein, refers to the 99th percentile of either a number- or volume-based median particle diameter, which is the diameter below which 99% by number of volume of the particle population is found. The number or volume measurement is indicated by [num] for number or [vol] for volume.

The microparticles of the various embodiments described herein can have a D50 particle diameter of approximately 5 μm up to approximately 20 μm. The microparticles of the various embodiments described herein can have a D50 particle diameter of approximately 20 μm up to approximately 50 μm. The microparticles can also have a diameter of less than about 5 μm (e.g., a D50 particle diameter of about 1 μm to about 5 μm; about 1.5 to about 4 μm; about 1.75 to about 3.5 μm; or about 2 to about 3 μm). In other embodiments, the microparticles can have a D90 particle diameter of less than about 9 μm (e.g., a D90 particle diameter of about 2 μm to about 9 μm; about 3 μm to about 7 μm; or about 3.5 μm to about 6 μm). In still other embodiments, the microparticles can have a D99 particle diameter of less than about 10 μm (e g, D99 particle diameter of about 3 μm to about 10 μm; about 4 μm to about 9 μm; about 4.5 to about 8 μm; or about 5 μm to about 7 μm). In other embodiments, the microparticles have a D100[num] particle diameter of less than about 15 μm (e.g., a D100 particle diameter of about 3 μm to about 12 μm, about 4 μm to about 11 μm; or about 5 μm to about 10 μm.

Particle diameters and particle size distributions can be determined by single particle optical sizing (SPOS) as described, for example, in U.S. Pat. No. 9,423,335, which is incorporated by reference as if fully set forth herein. Other methods for determining particle diameters and particle size distributions can also be used, including SEM, microscopy, light scattering, laser diffraction, coulter counter (electrical zone sensing), and digital image analysis.

The microparticles will have a density. The density is from about 0.5 to about 2 g/mL (e.g., from about 0.5 to about 1.5 g/mL; about 0.75 g/mL to about 1.5 g/mL; and about 1.0 g/mL to about 1.5 g/mL). The microparticles are biodegradable. In additional embodiments, the microparticles are bioerodible. In additional embodiments, the microparticles are biocompatible.

The microparticles can be present in any suitable and appropriate concentration, in the injectable compositions described herein, so long as the injectable compositions are still flowable and injectable. It should be understood, however, that a certain composition will ultimately cease to be injectable when a specific concentration of solids is reached. The microparticles can be present in a concentration of about 1 mg/mL to about 500 mg/mL in the vehicle (e.g., from about 50 mg/mL to about 250 mg/mL; about 100 mg/mL to about 500 mg/mL; about 10 mg/mL to about 300 mg/mL; or about 1 mg/mL to about 200 mg/mL).

The immunomodulatory agent can be present in a weight of up to about 50 wt. % of the polymer (e.g., from about 5 wt. % to about 50 wt. %; about 10 wt. % to about 40 wt. %; about 15 wt. % to about 35 wt. %; about 20 wt. % to about 35 wt. %; or about 20 wt % to about 40 wt. % of the polymer). The polymer comprising the API is used to produce the microparticles of the various embodiments described herein. In some embodiments, microparticles can be produced from such a polymer to give microparticles having high IA loading and that still exhibit controlled burst and sustained release. In further specific embodiments, the immunomodulatory agent can be present in a weight of up to about 40 wt. % of the polymer. In alternative specific embodiments, the immunomodulatory agent can be present in a weight of at least about 10 wt. % of the polymer. In further specific embodiments, the immunomodulatory agent can be present in a weight of at least about 20 wt % of the polymer. In alternative specific embodiments, the immunomodulatory agent can be present in a weight of about 20 to about 35 wt. % of the polymer or about 20 to about 40 wt. % of the polymer.

The immunomodulatory agent can be present in a weight of up to about 50 wt. % of a plurality of microparticles (e.g., from about 1 wt. % to about 5 wt. %; about 5 wt. % to about 50 wt. %, about 10 wt. % to about 40 wt. %; or about 15 wt. % to about 30 wt. % of a plurality of microparticles), wherein the weight percent can be adjusted to account for the presence of other materials that can be present m the microparticles.

The specific amount (measured in units of mass) of the IA(s) employed in the injectable compositions will typically depend, for example, on the amount of composition to be delivered. The amount of composition to be delivered will typically depend, for example, on the size, weight, age and health condition of the patient, the disease or disorder to be treated, the location or site of administration, the duration of drug release, potency of the IA(s) as well as the specific IA employed.

The microparticles described herein can be stored. e.g., as a lyophilized powder in a sealed, dry container. Prior to injection, the particles can be mixed with an injection vehicle, and an aliquot of the resulting suspension can be collected for injection into the patient. In typical settings, this procedure can be done by drawing the suspension into a needle for TA injection. In one embodiment, a 1.5-inch or 1-inch 25-gauge needle with a 3-mL syringe for injection, together with 2% lidocaine for local anesthetic can be used, with or without image guidance. Other methods will be apparent to those skilled in the art of IA injections. See, e.g., Lockman. "Knee joint injections and aspirations." Can Fam Physician. 2006 Nov. 10; 52(11): 1403-1404, which is incorporated by reference as if fully set forth herein.

Dosages, Formulations and Routes of Administration

Pharmaceutical formulations containing the therapeutic agents described herein can be prepared by available procedures using available ingredients. The formulations can contain pharmaceutically acceptable carriers, vehicles, and adjuvants. For example, the therapeutic agents can be formulated with common excipients, diluents, or carriers, and formed into tablets, capsules, solutions, suspensions, powders, aerosols, and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone. Agents for retarding dissolution can also be included such as paraffin. Resorption accelerators such as quaternary ammonium compounds can also be included. Surface active agents such as cetyl alcohol and glycerol monostearate can be included. Adsorptive pharmaceutical carriers such as kaolin and bentonite can be added. Preservatives can also be added. The compositions of the invention can also contain thickening agents such as cellulose and/or cellulose derivatives. They can also contain gums such as xanthan, guar or carbo gum or gum arabic, or alternatively polyethylene glycols, bentones and montmorillonites, and the like.

It is possible, for example, to prepare solutions using one or more aqueous or organic solvent(s) that is/are acceptable from the physiological standpoint, chosen, in addition to water, from solvents such as acetone, ethanol, isopropyl alcohol, glycol ethers such as the products sold under the name "Dowanol," polyglycols and polyethylene glycols, $C_1$-$C_4$ alkyl esters of short-chain acids, ethyl or isopropyl lactate, fatty acid triglycerides such as the products marketed under the name "Miglyol," isopropyl myristate, animal, mineral and vegetable oils and polysiloxanes.

The immunomodulatory agents can be formulated for parenteral administration (e.g., by injection, for example, bolus injection or continuous infusion into the joint, a draining lymph node of the inflammatory arthritis-affected joint, a subcutaneous tissue in the vicinity of the inflammatory arthritis-affected joint, or a joint capsule of the inflammatory arthritis-affected joint) and can be presented in unit dose form in ampoules, pre-filled syringes, small volume infusion containers or in multi-dose containers.

A dose of the immunomodulatory agent administered into the inflammatory arthritis-affected joint can be an amount sufficient to stabilize a population of $T_{reg}$ cells within the inflammatory arthritis-affected joint and does not cause systemic immunosuppression of the patient. A dose of the immunomodulatory agent administered into the inflammatory arthritis-affected joint can be an amount sufficient to increase a ratio of $T_{reg}$ cells to dysfunctional $T_{reg}$ cells within the inflammatory arthritis-affected joint and does not cause systemic immunosuppression of the patient.

As noted above, preservatives can be added to help maintain the shelve life of the dosage form. The active agents and other ingredients can form suspensions, solutions, or emulsions in oily or aqueous vehicles, and can contain formulatory agents such as suspending, stabilizing and/or dispersing agents. Alternatively, the therapeutic agents and other ingredients can be in powder form, obtained by aseptic isolation of sterile solid or by lyophilization from solution, for constitution with a suitable vehicle, e.g., sterile, pyrogen-free water, before use.

The compositions can also include antioxidants, surfactants, preservatives, film-forming, keratolytic or comedolytic agents. Antioxidants such as t-butylhydroquinone, butylated hydroxyanisole, butylated hydroxytoluene and α-tocopherol and its derivatives can be added.

The compositions can include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the pharmaceutical carriers and/or diluents that are useful in the pharmaceutical formulations of the present invention include water and physiologically acceptable buffered saline solutions such as phosphate buffered saline solutions pH 7.0-8.0.

Furthermore, the active ingredients can also be used in combination with other therapeutic agents, for example, pam relievers, anti-inflammatory agents, anti-cancer agents and the like, whether for the conditions described or some other condition.

Kits

The present invention further pertains to a packaged pharmaceutical composition such as a kit or other container for detecting, controlling, preventing, or treating a disease. The kits of the invention can be designed for detecting, controlling, preventing, or treating immune responses, immune conditions, and autoimmune diseases such as those described herein (e.g., an inflammatory arthritis condition).

In one embodiment, the kit or container can hold the immunomodulatory agent at least partially encapsulated in a biodegradable material, such as ATRA-encapsulated PLGA MPs, as well as instructions for preparing a composition that includes the immunomodulatory agent.

In another embodiment, the kit or container can hold a therapeutically effective amount of a pharmaceutical composition for treating, preventing, or controlling a disease and instructions for using the pharmaceutical composition for control of the disease. The pharmaceutical composition can include at least one type of immunomodulatory agent, such as the $T_{reg}$-inducer, synovial fibroblast modulator, or antigen presenting cell modulator in a therapeutically effective amount such that the disease is controlled, prevented, or treated. Such a composition can be in liquid form, powder form or other form permitting ready administration to a patient.

The kits of the invention can also comprise containers with tools useful for administering the compositions of the invention. Such tools can include syringes, swabs, catheters, antiseptic solutions, and the like. Some kits can include all of the desired tools, solutions, compounds, including mixing vessels, utensils, and injection devices, to treat a patient according to any of the methods described herein. In one embodiment, a kit includes the immunomodulatory agent encapsulated MPs of the various embodiments described herein. The immunomodulatory agent encapsulated MPs can be sterile-packaged as a dry powder in a suitable container (e.g., a substantially water-impermeable) such as a syringe, vial (e.g., the vial can include a septum and/or a crimp seal; and the vial can optionally comprise an inert atmosphere, such as a nitrogen atmosphere or dry air) or pouch (e.g., a pouch comprising a moisture barrier; and the pouch can optionally comprise an inert atmosphere, such as a nitrogen atmosphere, or dry air). The vial containing the immunomodulatory agent encapsulated MPs can have an injection cap that does not require the use of a needle to withdraw the suspended solution can be used to avoid damaging the MPs or separating the particles from the solution under negative pressure. The kit can also include a desiccant. The desiccant can be included in the pouch or integrated into the layers of the pouch material. In some embodiments, the microspheres can be sterile-packaged in frozen vehicle. As mentioned previously, the vehicle can be any suitable vehicle, including flowable vehicles (e.g., a liquid vehicle) such as a flowable, bioresorbable polymer, saline, sterile water, Ringer's solutions, and isotonic sodium chloride solutions. Examples of vehicles include, but are not limited, to Sodium Chloride Injection USP (0.9%). Ringer's Injection USP, Lactated Ringer's Injection USP, Sodium Lactate Injection USP, Dextrose Injection USP (5% or 10%), Bacteriostatic Water for Injection USP and Sterile Water for Injection USP. In some examples, the microspheres can be suspended in water; pre-filled into a container, such as a syringe; and frozen.

The kit can include at least one static mixing element, such as a one that is attached to a syringe. In some embodiments, the user provides a static mixing element to deliver the microspheres.

The kit can also include beads that serve to, among other things, disaggregate any microsphere agglomeration that can occur when the microspheres of the various embodiments described herein are reconstituted with a vehicle. In some embodiments, the beads are sufficiently larger than the microspheres, so that the microspheres can be selectively delivered to the injection site, while the beads remain in the injection device (e.g., a syringe). For example, the beads can have at least one dimension that is about 1 mm. The beads can be of any suitable shape, including spherical and oval in shape. The beads can also have any suitable texture. For example, the beads can have a smooth texture and/or a rough texture. The beads can also be made of any suitable material, including glass, ceramic, metal (e.g. stainless steel), polymeric (e.g. ePTFE or polpropylene), and composite materials. The beads can be included in the kit in a separate container; in the same container as the microspheres of the various embodiments described herein; or the user can provide beads of suitable size, shape, texture, and/or materials at the point of care.

The kit can also include an injection vehicle described herein, such as sterile water or sterile saline (e.g., in the case where the target injection area is substantially hydrophobic or lipophilic) or other suitable vehicle, including a non-aqueous vehicle (e.g., a hydrophobic, liquid vehicle described herein). Prior to administration, the microspheres can be added to the injection vehicle to form a suspension and agitated (e.g., stirred, shaken or vortexed) to maximize homogeneity. In some embodiments, the microspheres can come in the kit, suspended in a vehicle, such as a non-aqueous vehicle (e.g., a hydrophobic, liquid vehicle described herein).

The kit can further include a hypodermic needle or other delivery device, such as a cannula, catheter, or other suitable tubing. The kit can further include instructions, dosage tables, and other pertinent information for a practitioner.

The kit can include one or more additional APIs (e.g., a local anesthetic) either in the same container as the microspheres of the various embodiments described herein or in a separate container, such that the API in a separate container can be combined with the microspheres and vehicle to provide a bolus of an API upon administration (e.g., injection) of the microspheres. In other embodiments, the user can provide one or more additional APIs that can be combined with the microspheres of the various embodiments described herein, at the point of care. In one specific example, a kit comprises a pre-filled syringe for IA knee injection comprising ATRA-encapsulated PLGA MPs in 2 ml 1% lidocaine. The ATRA-encapsulated PLGA MPs and lidocaine are, in some embodiments, lyophilized and reconstituted with a suitable vehicle (e.g., sterile saline or water) that suspends the PLGA MPs and dissolves the powder prior to IA injection.

The kits can include instructions or printed indicia, to provide for directions for reconstituting the contents of the multiple packages, and/or for the administration of the resulting composition (e.g., the injectable compositions). For example, instructions on printed indicia can instruct injection into biological tissue including at least one of fatty tissue, epidural tissue, and at or near a targeted nerve.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y." unless indicated otherwise. Likewise, the statement "about X, Y, or about Z" has the same meaning as "about X, about Y. or about Z," unless indicated otherwise.

In this document, the terms "a," "an." or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

EXAMPLES

Figure 1D:
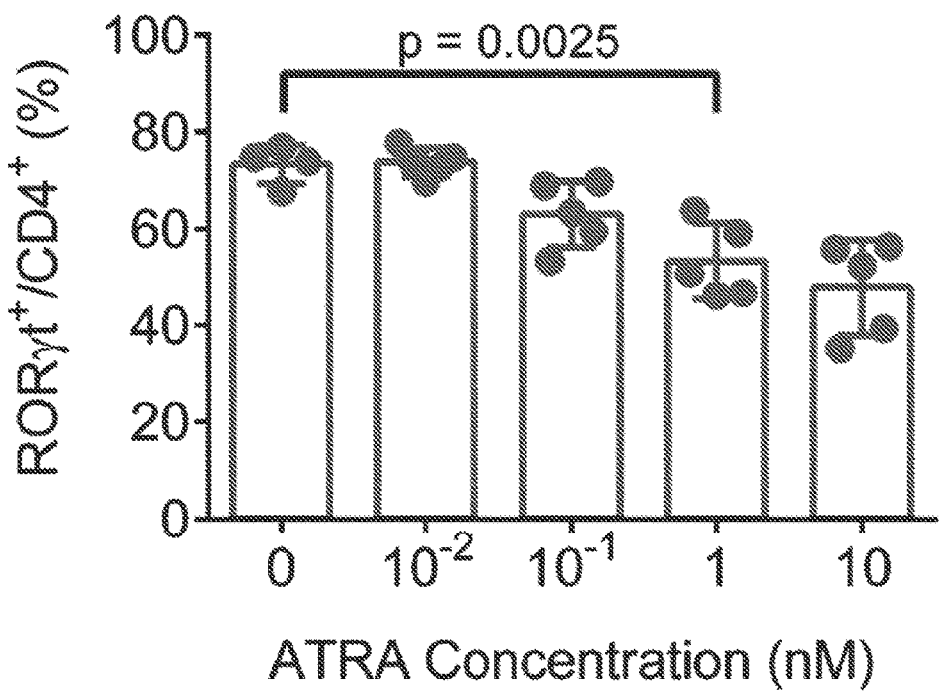

Example 1: ATRA Promotes $T_{reg}$ Differentiation and Stability in Mouse and Human T Cells Ex Vivo To test the effect of ATRA on enhancing $T_{reg}$ cells, an ex vivo differentiation and stabilization assay in Th17 inflammatory conditions using cytokine supplementation was performed (FIG. 1A). Naïve SKG CD4+ T cells were isolated to consistently obtain greater than 90% CD4+CD44−CD62L+ post-enrichment (data not shown). Subsequently, these cells were stimulated with anti-mouse CD3 ($\alpha$CD3) and CD28 ($\alpha$CD28) antibodies along with Th17 polarizing cytokines IL-6, TGF-$\beta$1, IL-1$\beta$, and IL-23, and immunophenotypes were analyzed after four days. In a subset of conditions, ATRA was added to the T cell culture medium, ranging from 10 pM to 10 nM. ATRA differentially upregulated FoxP3 and suppressed IL17A expression in a concentration-dependent manner (data not shown). Above 100 pM, ATRA consistently enhanced FoxP3 expression (40.0±3.4%), while below 100 pM, 11.2±2.3% of T cells expressed FoxP3 (FIG. 1B). The fraction of IL-17A-CD4+ T cells was comparable at 10 pM ATRA relative to control (9.5±1.7% vs 11.3±1.5%), while ATRA concentrations of 100 pM (7.2±1.5%), 1 nM (5.4±1.9%), and 10 nM (5.4±2.3%) reduced expression of IL-17A, with a peak effect at 1 nM (FIG. 1C). In addition to reduced expression of IL-17A, the fraction of ROR$\gamma$t+CD4+ T cells was reduced in 1 nM ATRA conditions (53.3±7.9%) relative to cells exposed 0 nM ATRA (73.3±3.9%) (FIG. 1D).

Next, the effect of ATRA on human T cells was assessed (data not shown). Naïve human CD4+ T cells were isolated from peripheral healthy human donor blood, consistently obtaining greater than 90% CD4+CD45ROCD62L+ post-enrichment. Subsequently, these cells were stimulated with anti-human CD3 and CD28 antibodies along with IL-6, TGF-$\beta$1. IL-1$\beta$, IL-23, and IL-21. In a subset of experimental conditions, ATRA was added to the human T cell expansion medium at concentrations ranging from 10 pM-10 nM, as above. To represent the differential effect of ATRA on Th17 and $T_{reg}$ induction in human T cells, we compared the ratio of IL-17A+ T cells to FoxP3+ T cells. At 1 nM ATRA, the ratio of IL-17+:FoxP3+ cells in one donor was 2.68:1±10.47, compared to 4.87:1±0.02 and 4.02:1±0.99 in no ATRA and 10 pM ATRA, respectively (data not shown).

Figure 1G:
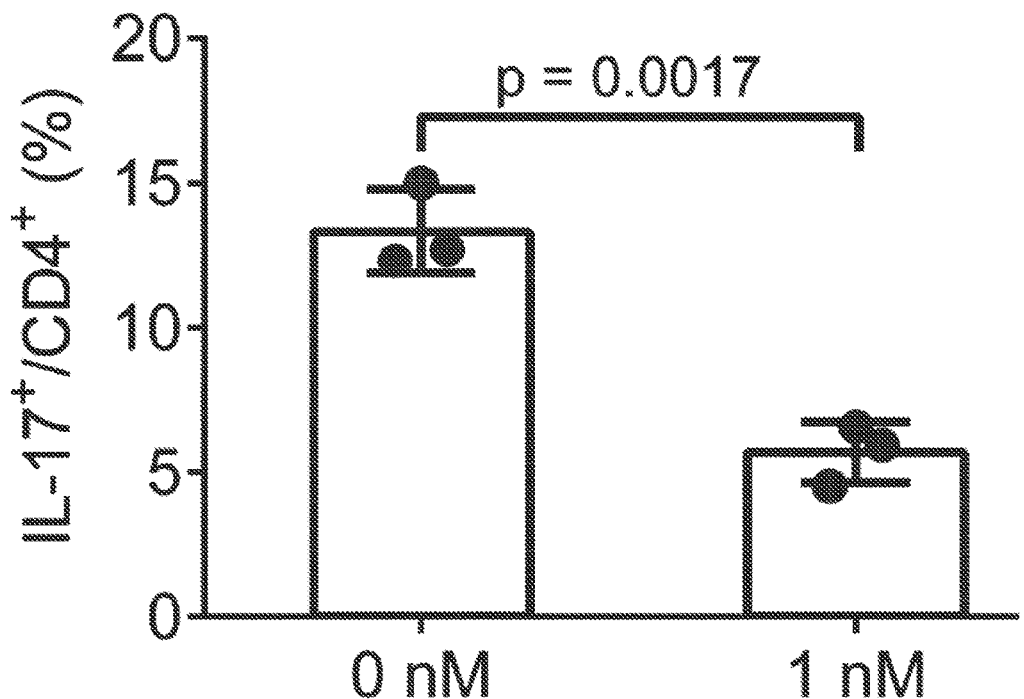
Figure 1H:
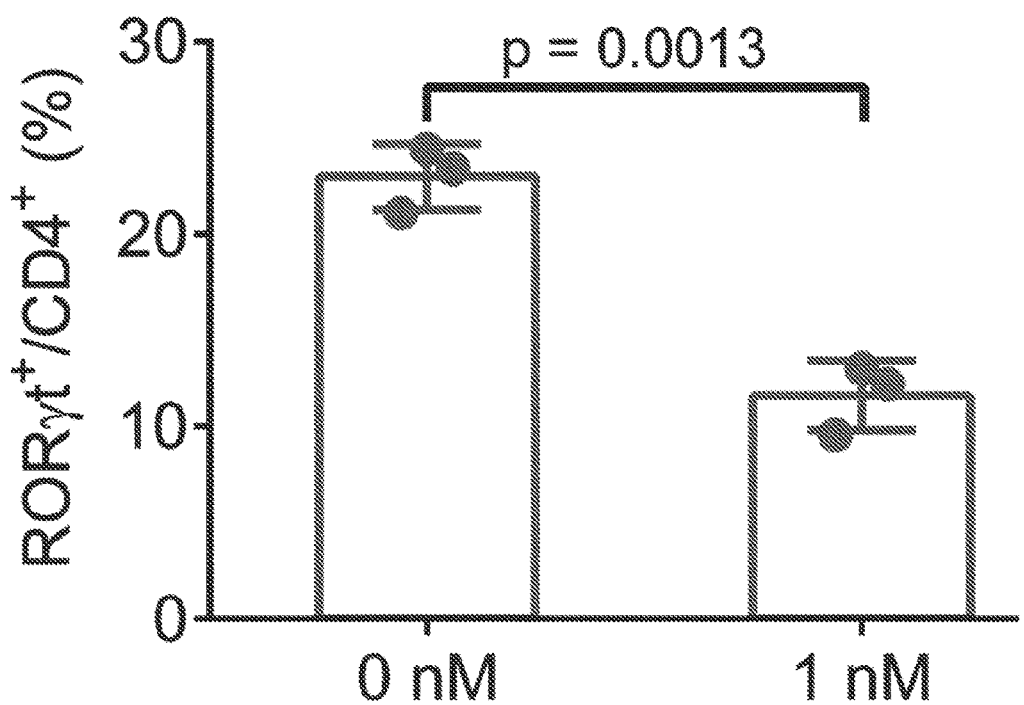

The effect of ATRA on maintaining ex vivo stability of $T_{reg}$ was quantified following a previously established $T_{reg}$ cell stability assay SKG FoxP3eGFP $T_{reg}$ cells were sorted by flow cytometry (TCR-β+CD4+eGFP+) and stimulated with αCD3 and αCD28 in the presence of IL6 with or without 1 nM ATRA for 72 hours (FIG. 1E) The addition of ATRA to the cell culture medium enhanced $T_{reg}$ cell stability, with 71.6±5.5% of cells retaining FoxP3eGFP expression, significantly greater than 56.4±2.2% cells retaining FoxP3eGFP expression in the absence of ATRA in the cell culture medium (FIG. 1F). The loss of FoxP3 expression correlated with $T_{reg}$ cell transitioning to a Th17-like $exT_{reg}$ cell phenotype, with 23.0±1.7% and 13.3±1.5% of cells without ATRA expressing RORγt and IL-17, respectively, compared to 11.6±1.8% and 5.7±1.1% of cells cultured with 1 nM ATRA (FIGS. 1G and H).

Figure 2A:
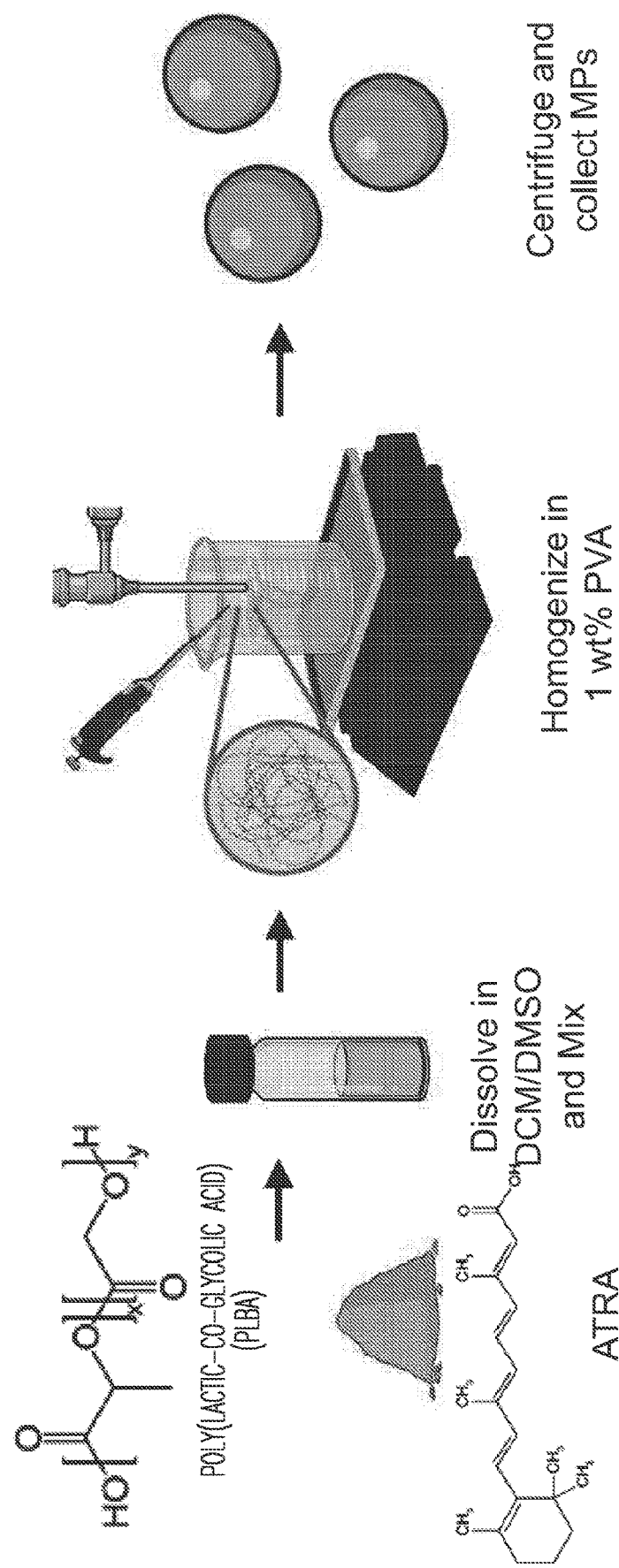
FIGS. 2A-K illustrate the encapsulation of ATRA in poly-(lactic-co-glycolic) acid (PLGA) microparticles (MPs) that provide sustained or extended release of bioactive ATRA.
Figure 2B:
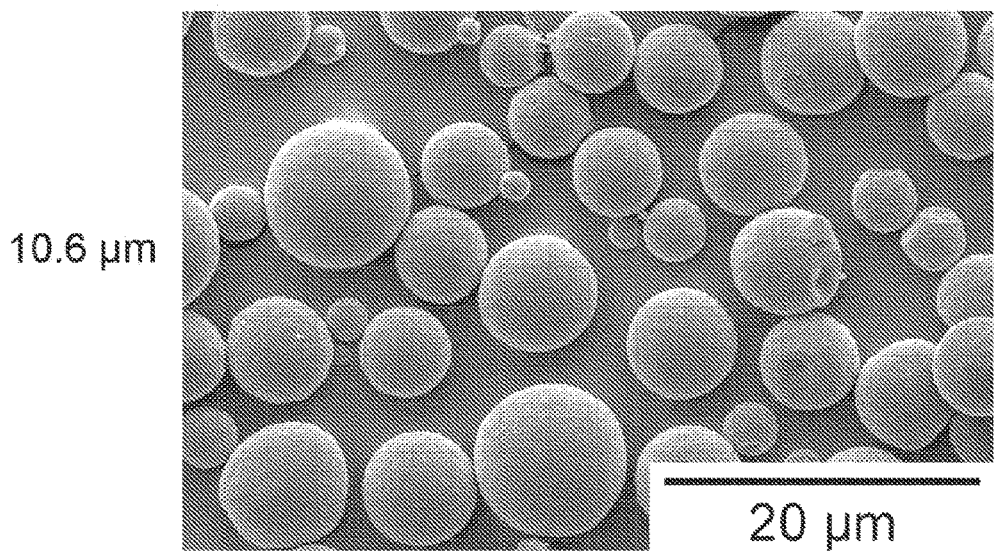
Figure 2C:
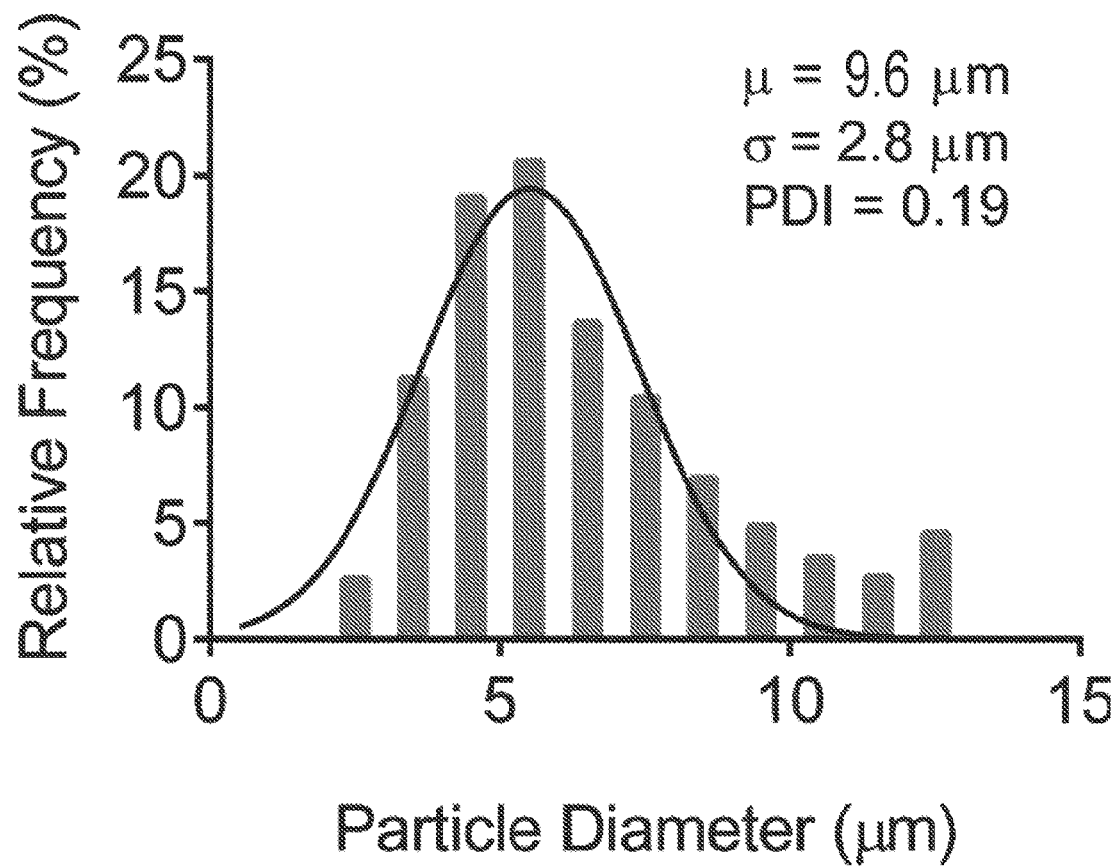
Figure 2D:
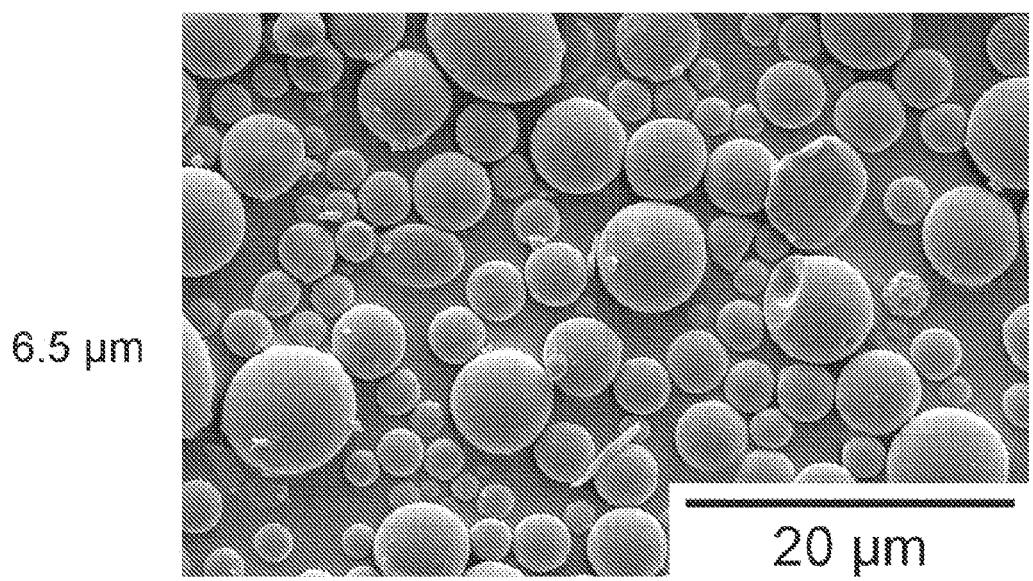
Figure 2E:
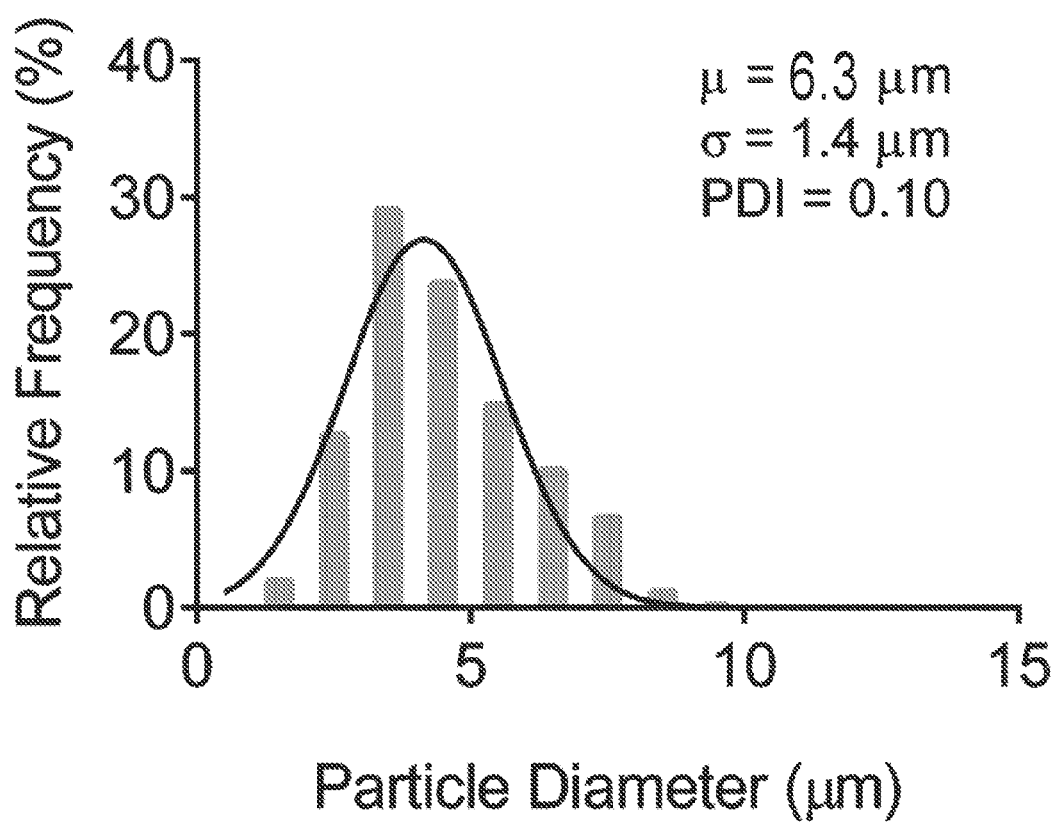
Figure 2F:
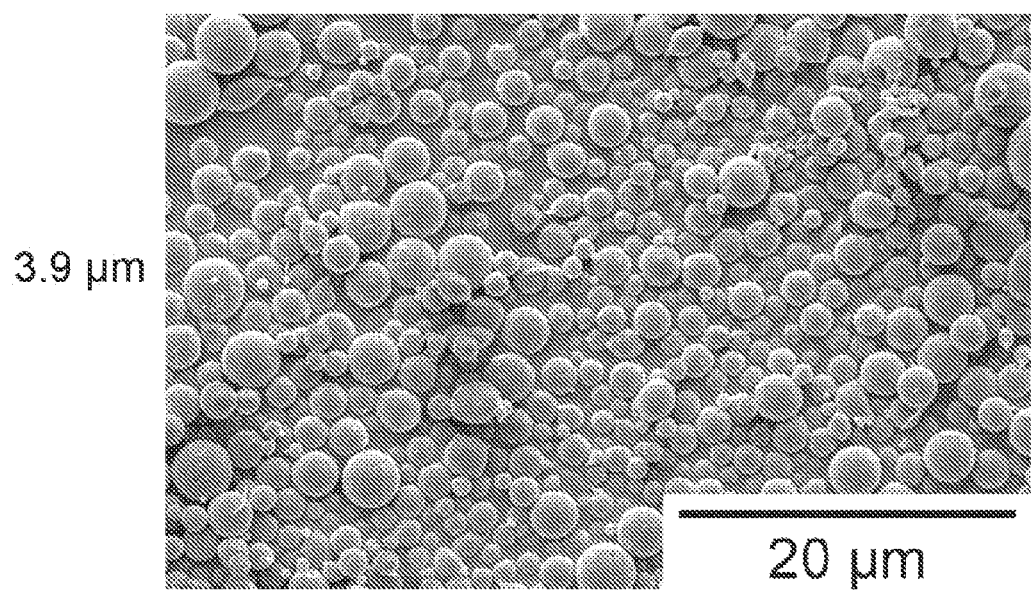
Figure 2G:
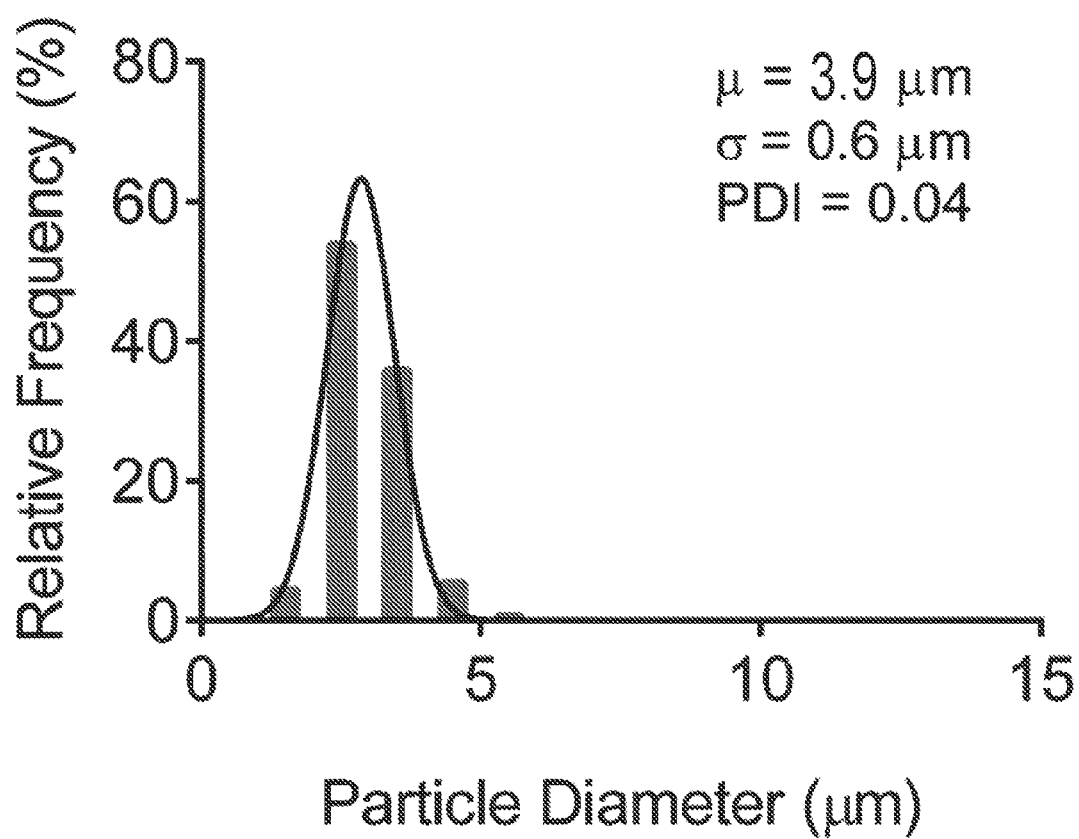
Figure 2H:
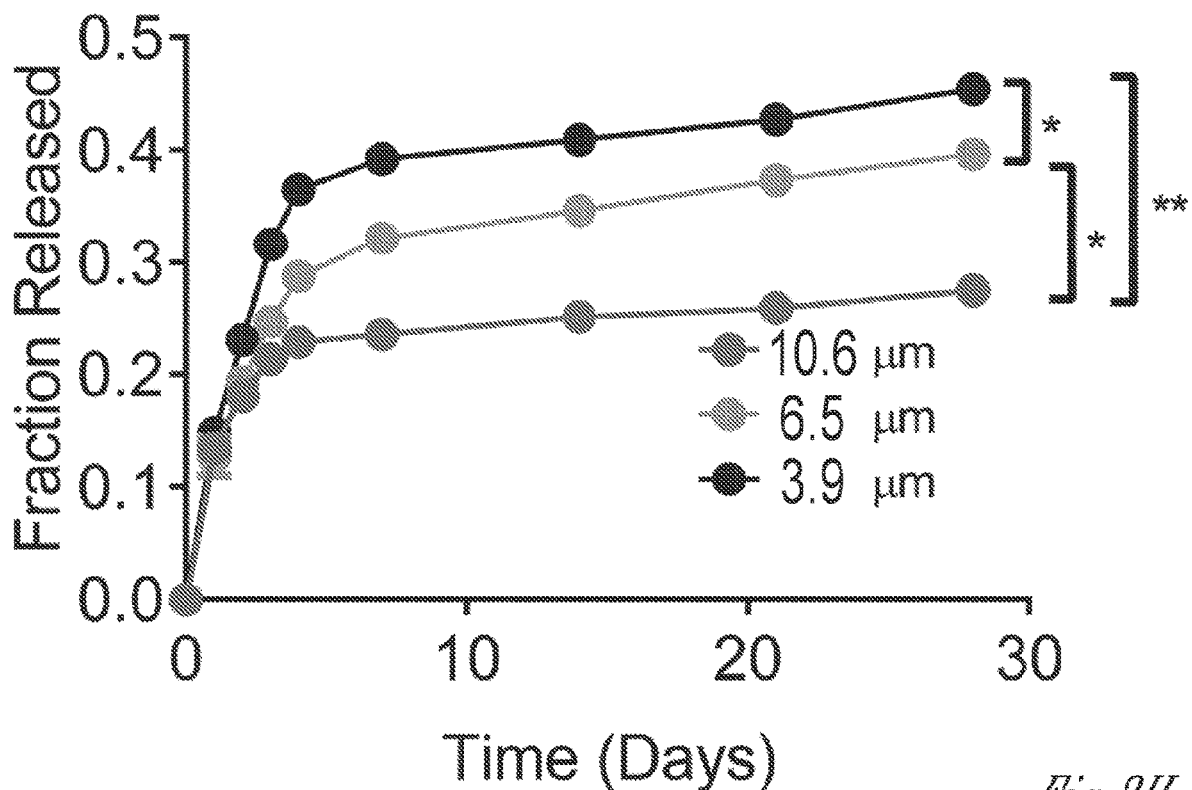

Example 2: Poly-(Lactic-Co-Glycolic) Acid Microparticles Sustain Bioactive ATRA Release To formulate sustained release ATRA for intra-articular (IA) drug delivery in the inflamed joint, IA injectable microparticles (MPs) were produced from poly-(lactic-co-glycolic) acid (PLGA) using a single emulsion method to generate ATRA-encapsulated PLGA MPs (FIG. 2A). Scanning electron microscopy of lyophilized ATRA-encapsulated PLGA MPs was used to characterize the surface morphology. In general, the surface of pristine ATRA-encapsulated PLGA MPs was uniformly textured (FIGS. 2B, 2D, and 2F). By controlling the homogenization rate, we generated particles and quantified their sizes and distributions which were 10.6±0.7 μm, 6.5±0.4 μm and 3.9±0.4 μm volume averaged diameters across three batches, and a polydispersity index £ 0.30 within each batch in all conditions (FIGS. 2C, 2E, and 2G, respectively). ATRA-encapsulated PLGA MPshave a loading efficiency of 62.4±3.2% which resulted in a composition of approximately 1.2 wt % ATRA. To quantify ATRA release in vitro, 10 mg ATRA-encapsulated PLGA MPs were suspended in 1 ml of 0.1% BSA in PBS and incubated at 37° C., and release supernatant was collected over 28 days at pre-determined timepoints. Approximately 13% of ATRA was released within the first 24 hours (FIG. 2D). From 24-96 hours, 10±0.6%, 15±0.2%, and 22±1.3% of the original ATRA content was released from the 10.6 μm, 6.5 μm and 3.9 μm average diameter ATRA-encapsulated PLGA MPs, respectively. Subsequently, ATRA release was sustained from all ATRA-encapsulated PLGA MPs for the next 24 days at a rate of ~0.4% of the initial loaded ATRA per day, corresponding to a release of ~0.52 ng ATRA per mg of particles per day. To characterize changes in particle morphology during in vitro degradation, the ATRA-encapsulated PLGA MPs were periodically collected, washed, and imaged. Particles initially swelled before undergoing degradation until the bulk erosion resulted in structural collapse (data not shown). By day 21, the majority of 10.6 μm particles retained their morphology, while the majority of 6.5 μm particles had commenced eroding, and most 3.9 μm particles had collapsed.

To estimate in vivo concentrations of ATRA in the synovial fluid, spleen, and peripheral blood after IA injection, a two-compartment pharmacokinetic model was developed based on the in vitro release profile (data not shown). The biodistribution of ATRA was approximated using first order rate equations and previously reported experimentally measured kinetic parameters for ATRA half-life in the serum and synovium permeability data (data not shown). The model showed that after an initial spike, concentrations in the joint would be maintained at greater than 6 nM for at least 28 days with 6.5 μm ATRA-encapsulated PLGA MPs. The concentration of ATRA in the peripheral blood was below physiologically relevant values (<20 pM) (data not shown) Based on the model and degradation profile, the 6.5 μm ATRA-encapsulated PLGA MPs was selected for further evaluation.

Figure 2I:
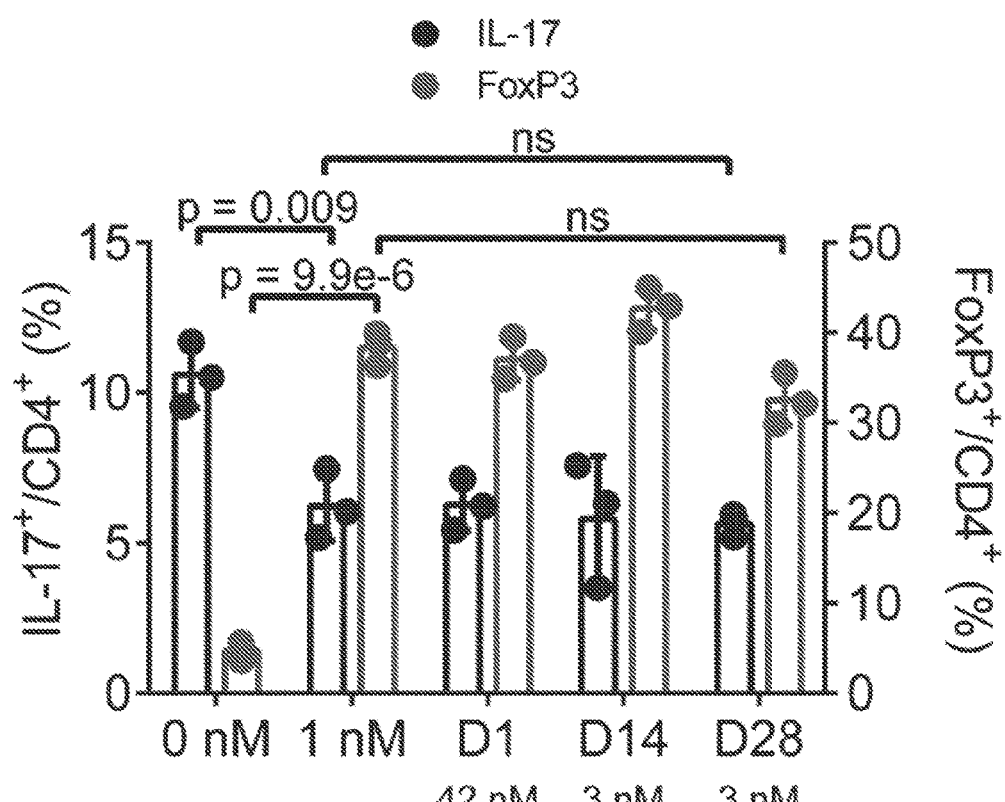
Figure 2J:
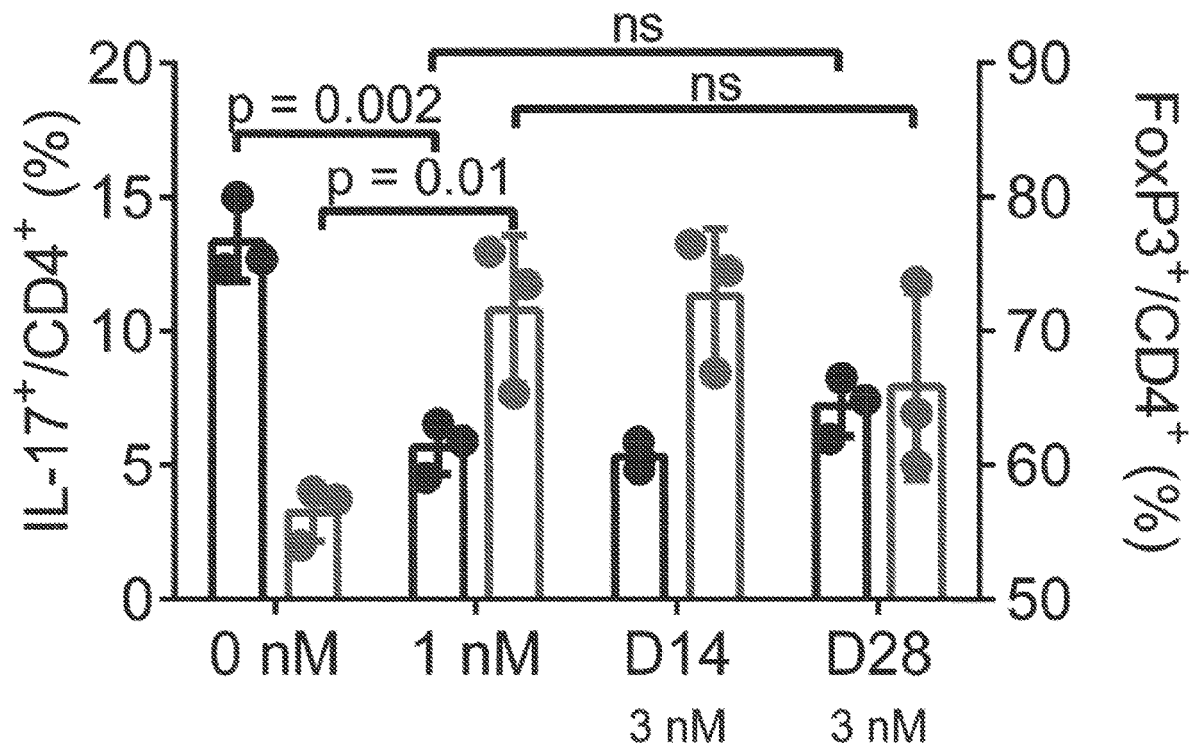
Figure 2K:
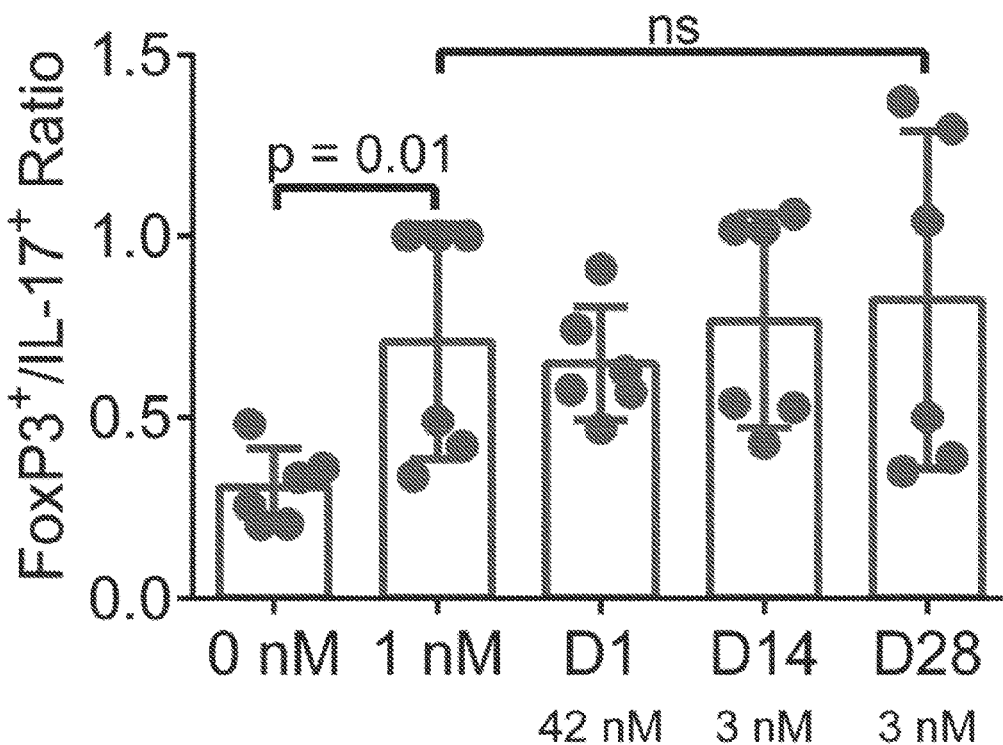

The bioactivity of released ATRA was assessed following the experimental schematic outlined in FIG. 1A with supernatant collected at day 1, 14 and 28 and replicates diluted to the expected joint concentration based on delivery of 2 μg ATRA-encapsulated PLGA MPs injected in ~20 μL of synovial fluid. The bioactivity of ATRA collected at all three timepoints was comparable to freshly prepared 1 nM ATRA, comparable to the results from the murine Th17 9 differentiation assay increasing FoxP3 expression and reducing IL-17 expression (FIG. 2I). Released ATRA also stabilized $T_{reg}$ cells comparable to 1 nM ATRA, improving FoxP3 expression while suppressing IL-17 expression (FIG. 2I). In the human Th17 differentiation assay, released ATRA also retained bioactivity comparable to 1 nM ATRA (FIG. 2K).

Figure 3A:
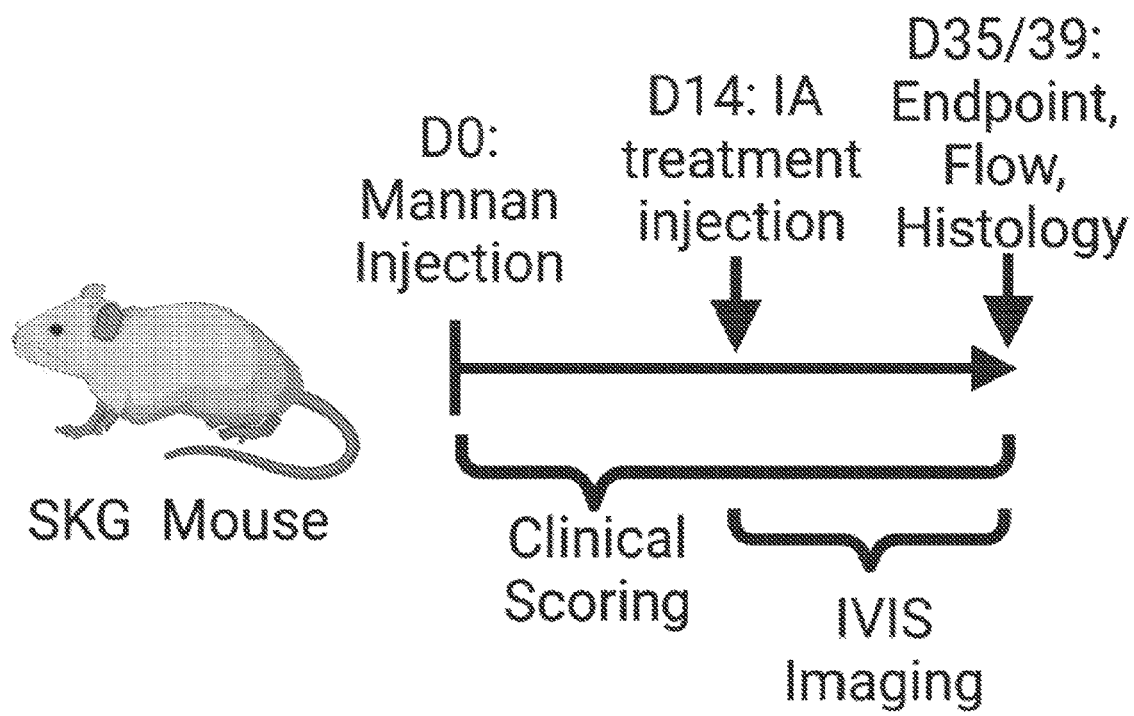
FIGS. 3A-J illustrates how ATRA-encapsulated PLGA MPs ameliorate autoimmune arthritis in SKG mice.
Figure 3B:
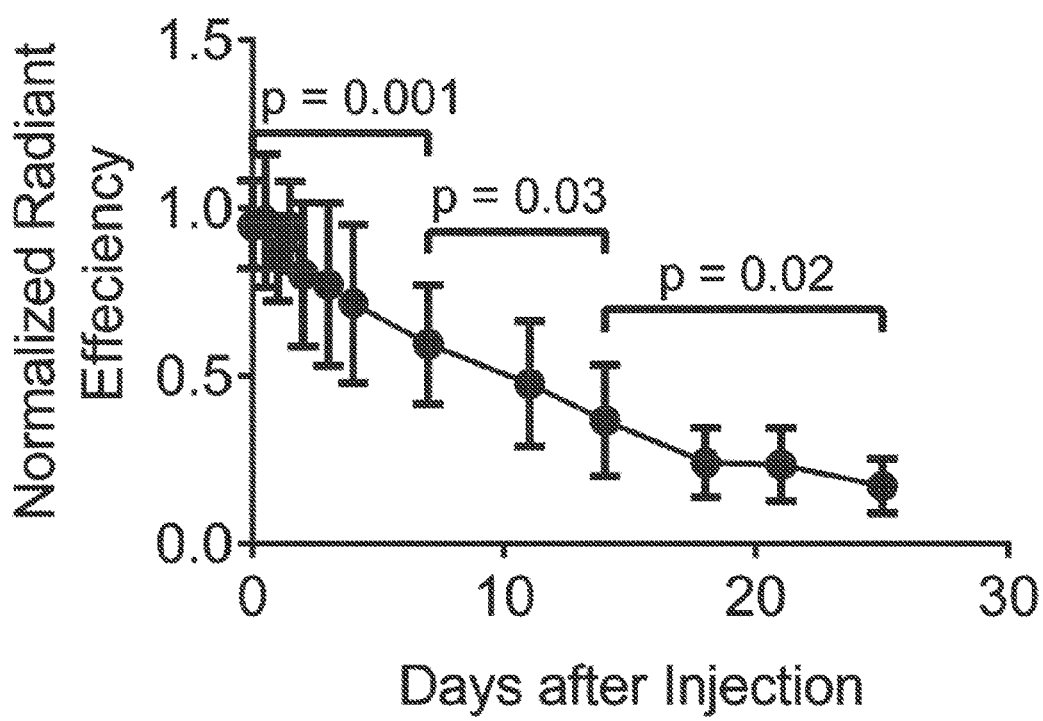
Figure 3C:
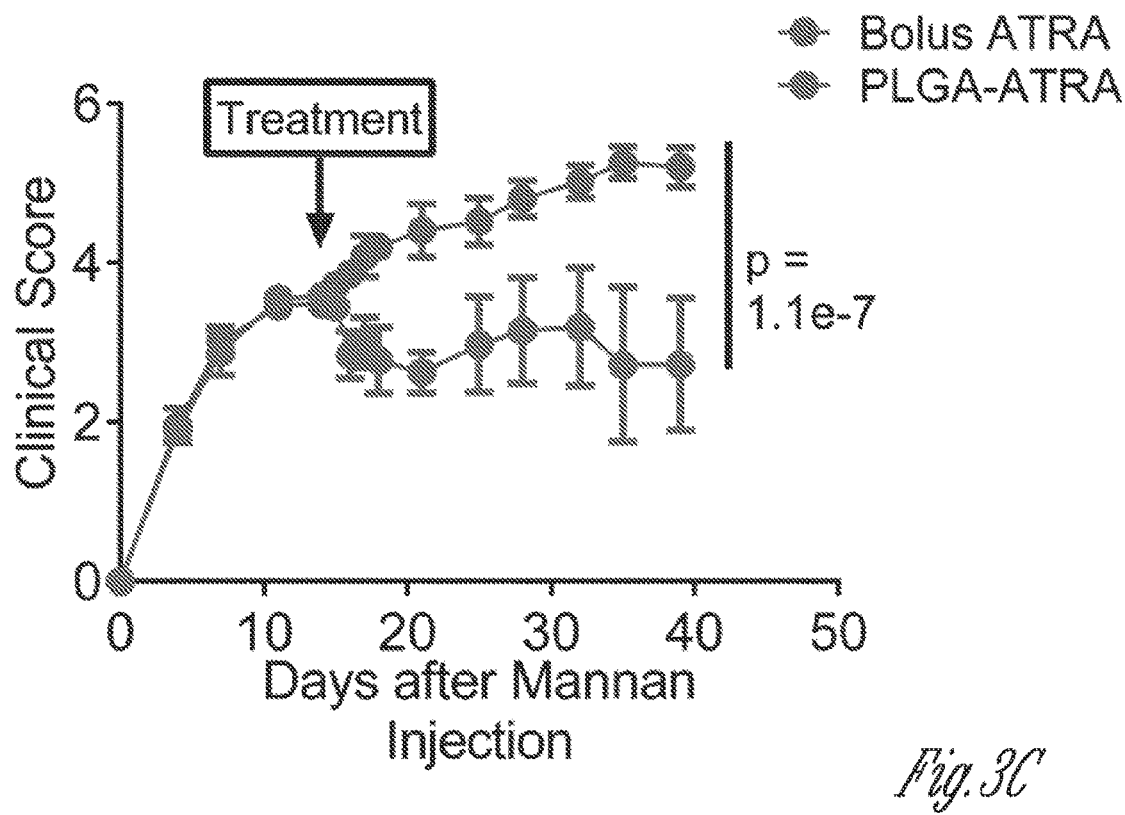
Figure 3D:
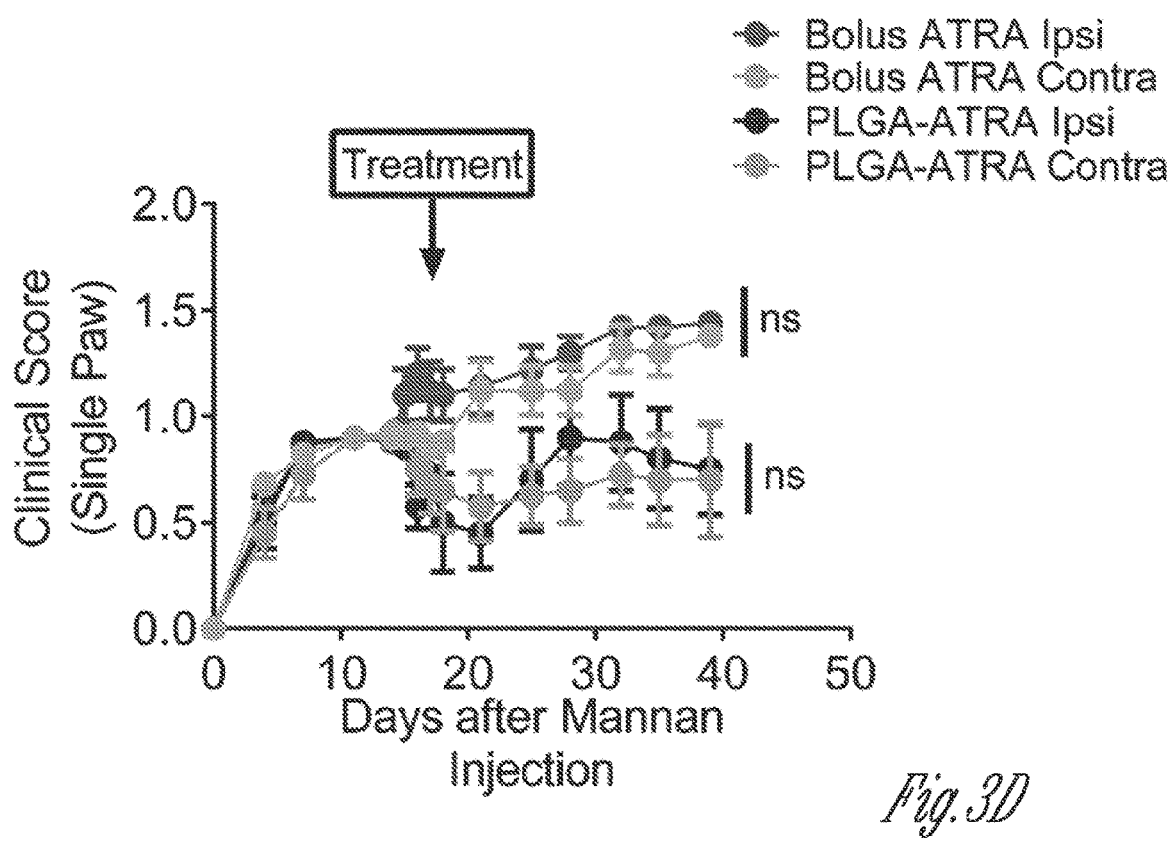
Figure 3E:
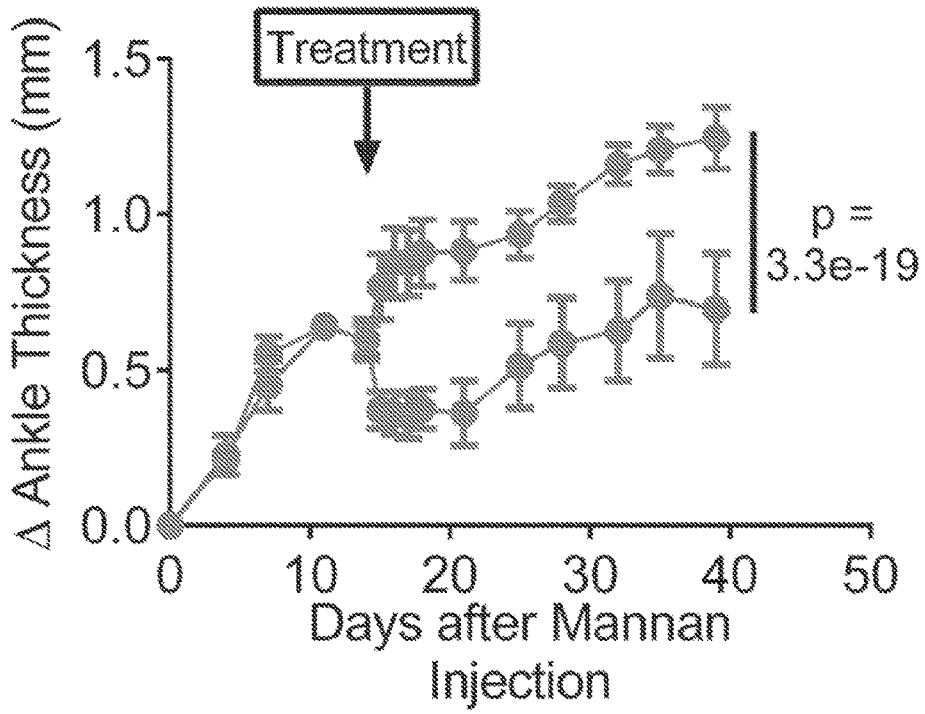
Figure 3F:
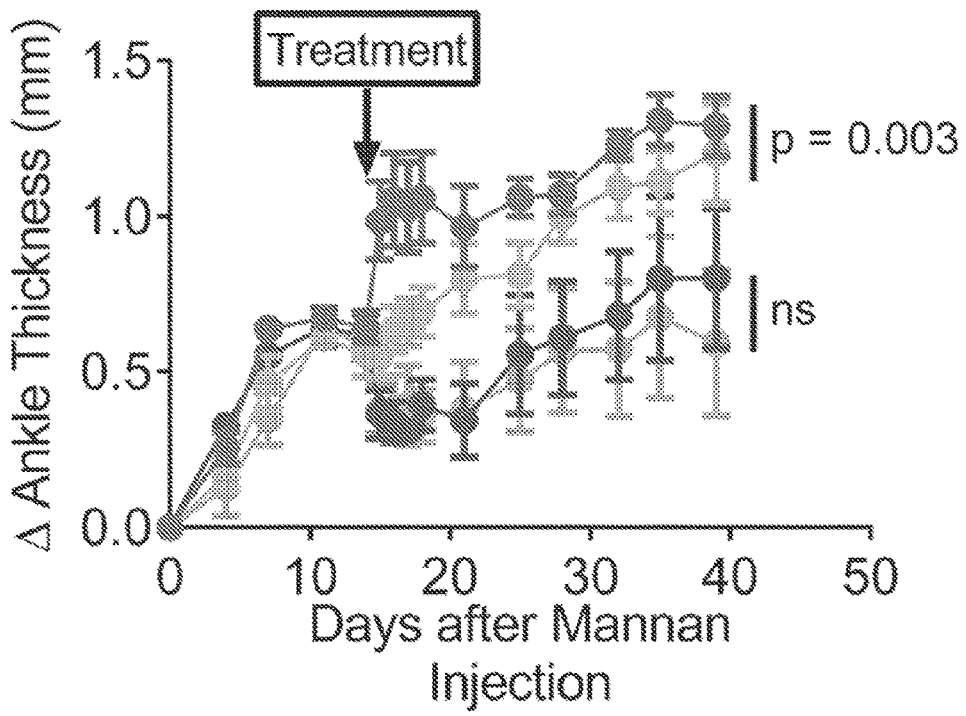
Figure 3G:
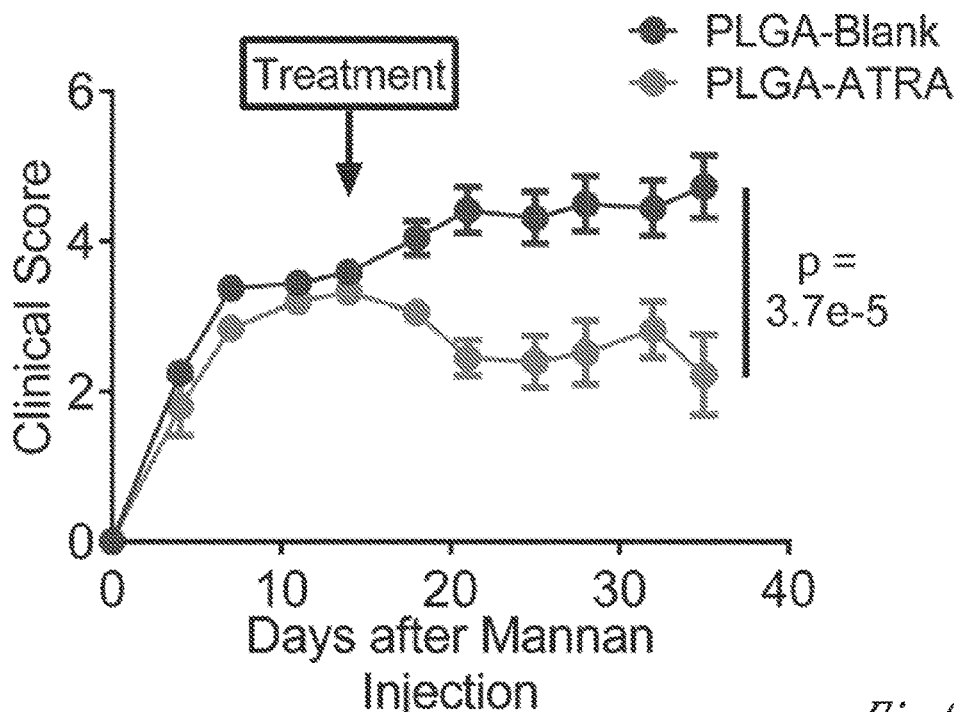
Figure 3H:
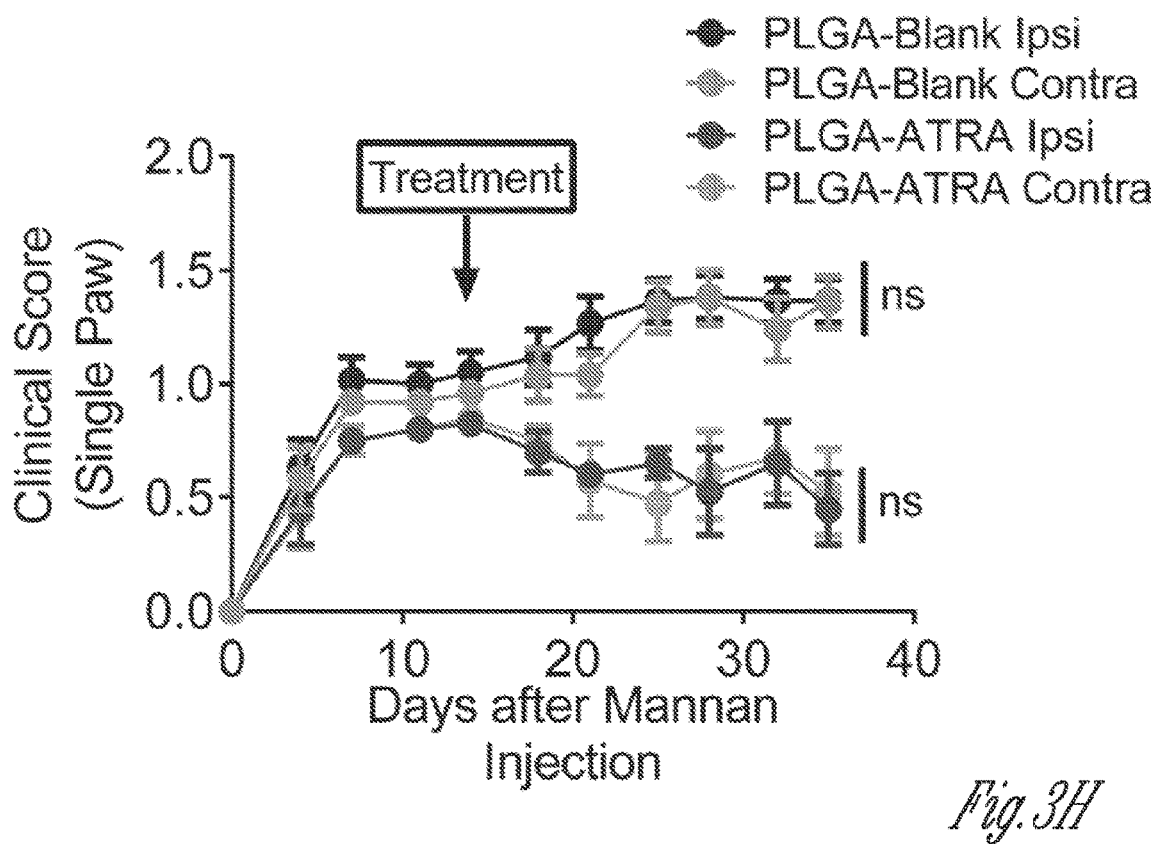
Figure 3I:
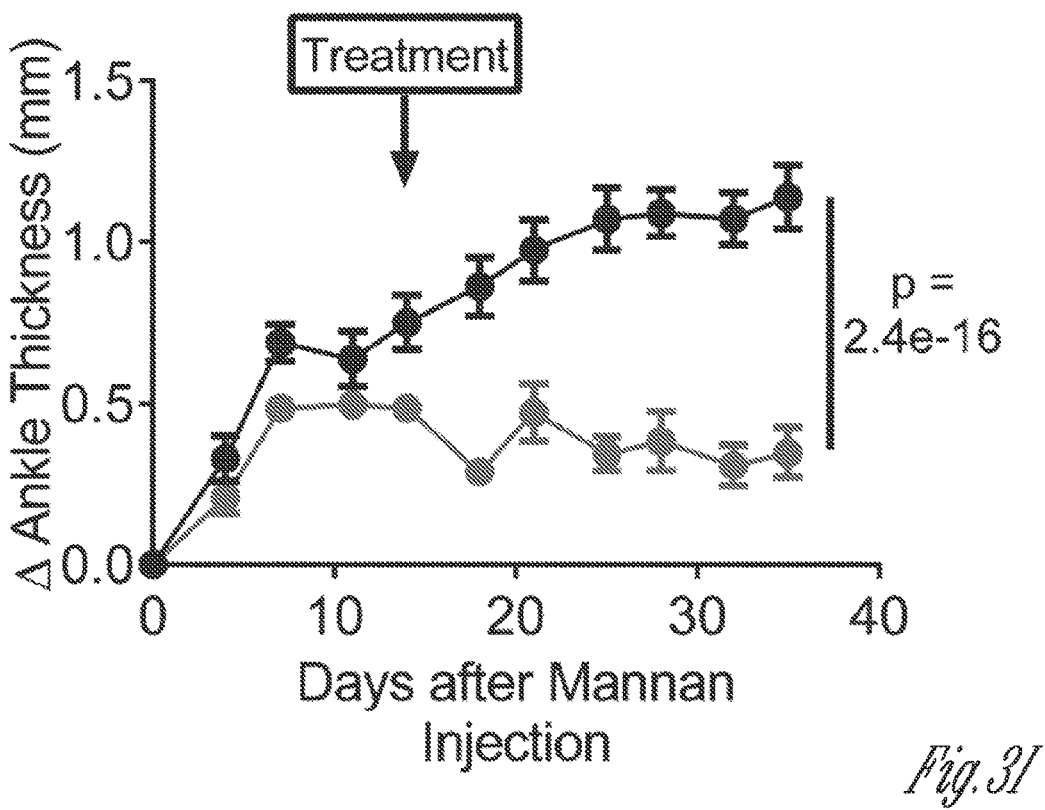
Figure 3J:
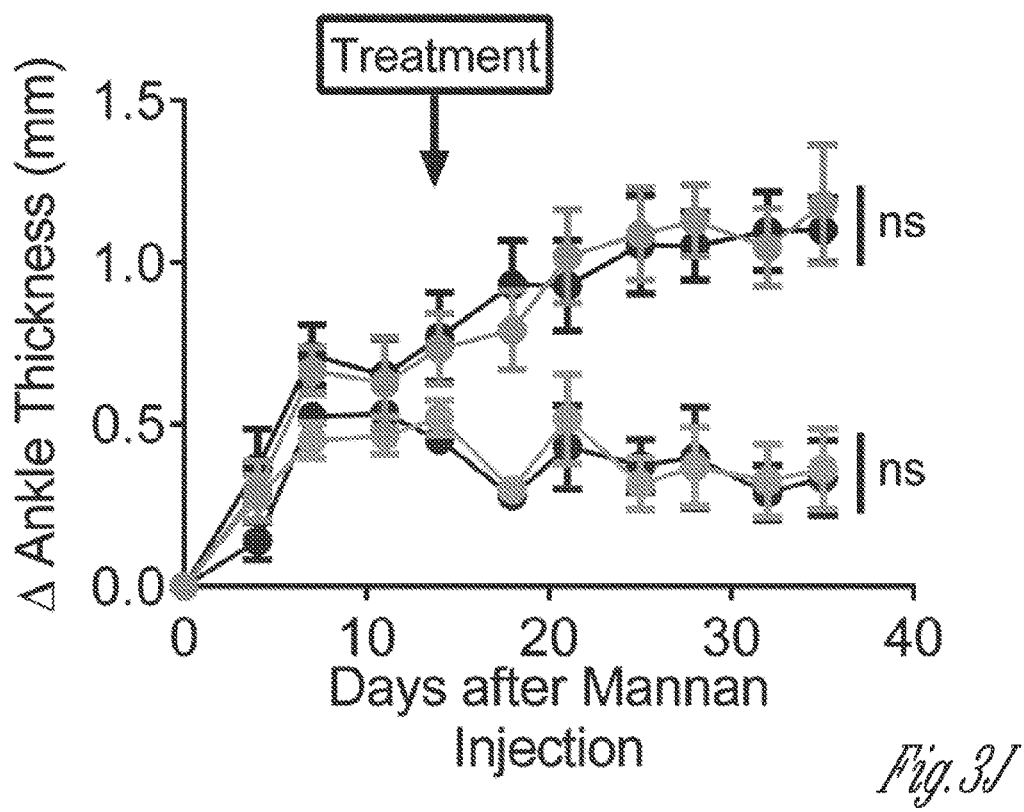
Figure 6A:
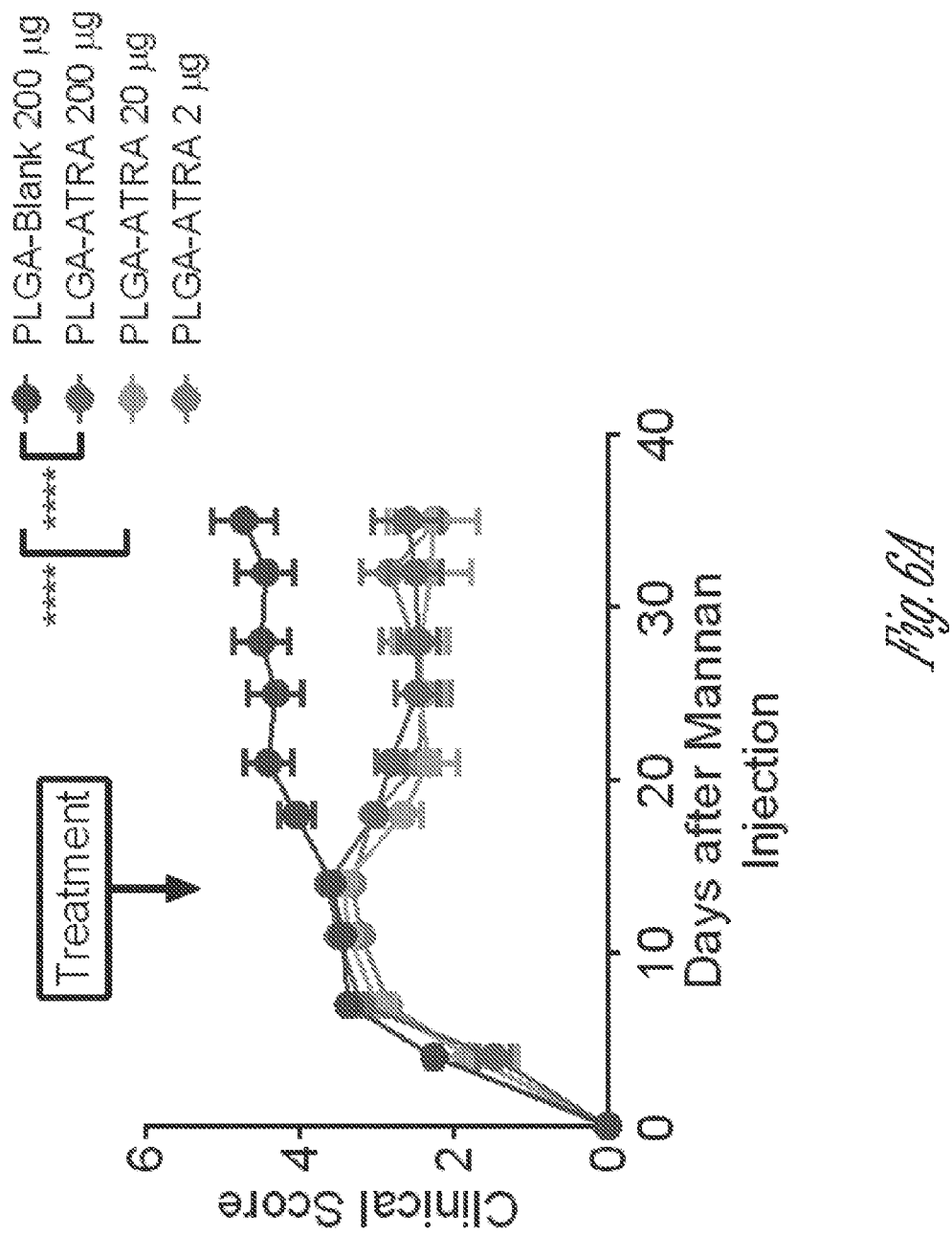
FIG. 6A-C depicts an extended characterization of ATRA-mediated improvement in arthritis outcomes in SKG mice.
Figure 6B:
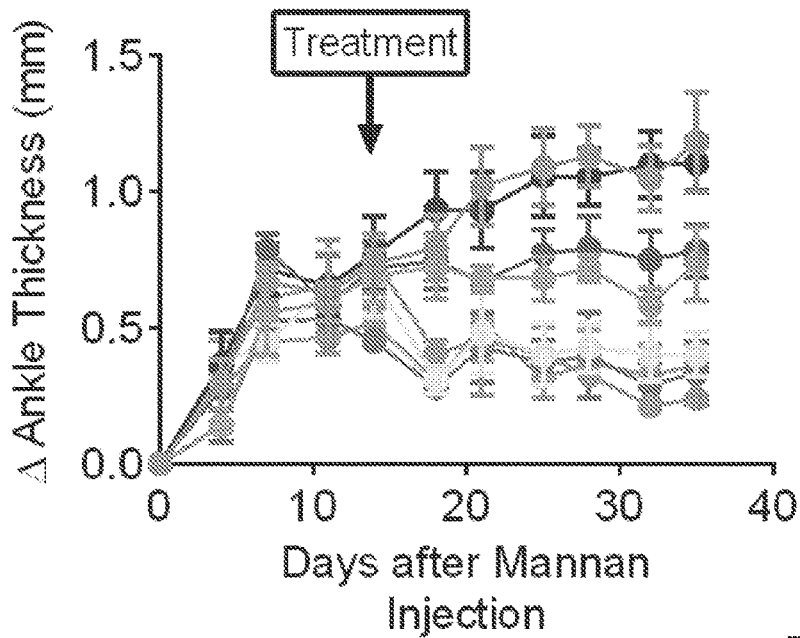
Figure 6C:
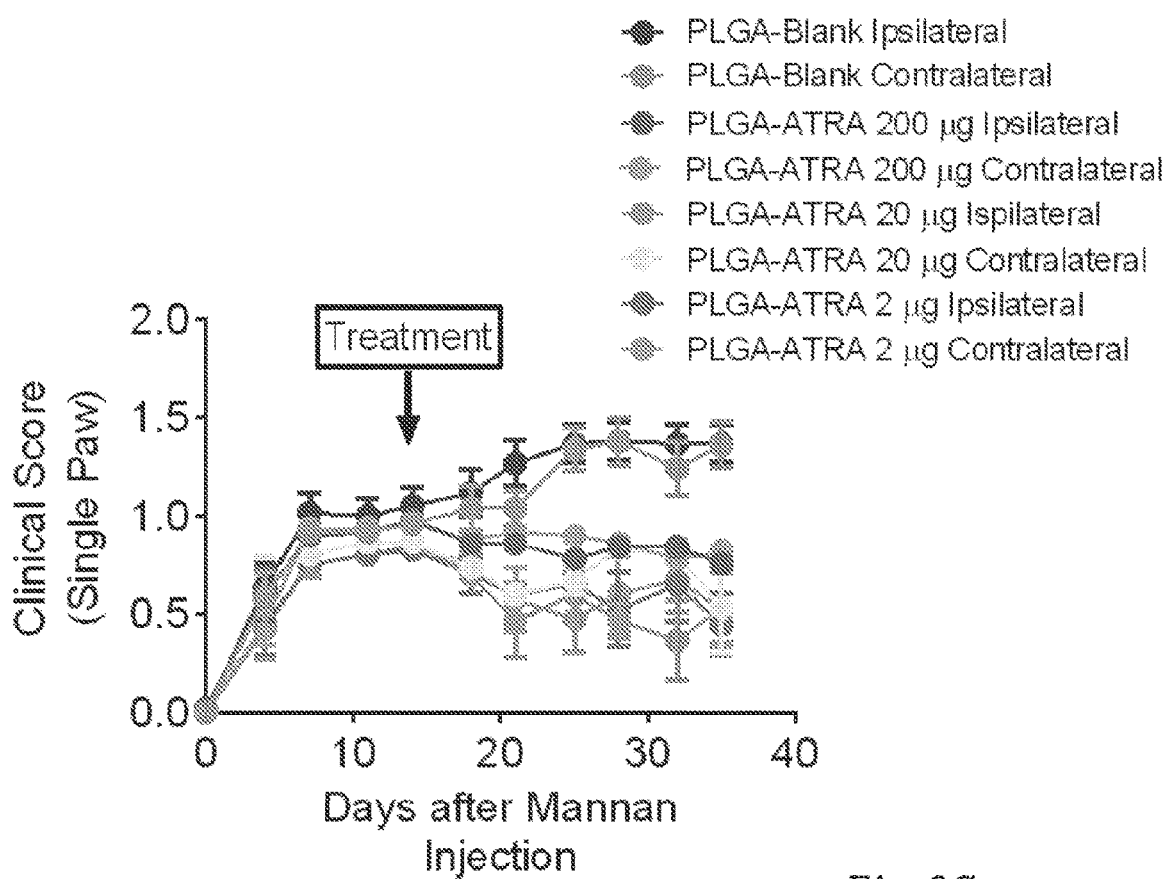

Example 3. ATRA-Encapsulated PLGA MPs Suppress Joint Inflammation in SKG Arthritis To assess the feasibility of modulating established SKG arthritis. ATRA-encapsulated PLGA MPs were injected into the tibial/tarsal ankle joint of ten SKG mice with middle stage arthritis, prior to the development of severe symptoms. PLGA-Blank MPs were injected into the tibial/tarsal ankle joint of eleven SKG mice with middle stage arthritis. Arthritis onset was synchronized using inter-peritoneal (IP) mannan injection. ATRA-encapsulated PLGA MPs treatment was administered after 14 days, corresponding to established SKG arthritis (FIG. 3A). To track MP degradation in vivo, cyanine-5 (Cy5) conjugated PLGA was incorporated to generate fluorescently labeled Cy5 PLGA MPs and PLGA MPs without ATRA (PLGA-Blank MPs). The PLGA-Blank MPs were imaged using a live animal. In Vivo Imaging System (IVIS). To determine the role of sustained ATRA release in suppressing SKG arthritis, IA injected ATRA-encapsulated PLGA MPs was compared to a dose-matched IA injection of bolus ATRA in solution. Mice received 2 μg ATRA-encapsulated PLGA MPs suspended in 20 μL of sterile phosphate buffered saline PBS in a single ankle joint (ipsilateral ankle) via IA injection. The contralateral hind ankle joint (contralateral ankle) was injected with Cy5 PLGA-Blank MP in 20 μL of sterile PBS in a similar fashion. Dose matched bolus ATRA suspended in 20 μL of sterile corn oil was injected in the ipsilateral ankle of control mice. The contralateral hind ankle joint (contralateral ankle) was injected with Cy5 PLGA-Blank MP in 20 μL of sterile PBS in a similar fashion. Based on fluorescence attenuation, MPs remained localized in the joint after injection and steadily degraded over the course of the study (FIG. 3B). Arthritis progression was quantified using bi-weekly clinical scoring between the treatment groups. Pre-treatment clinical scores of mice were comparable between the groups, which increased rapidly from an initial score of 0 to an average score of 3.5 on day 14 prior to treatment with mild swelling observed in both wrist and ankle joints. The majority of the digits were swollen in all the groups (FIG. 3C-F). The severity of arthritis was suppressed in IA ATRA-encapsulated PLGA MP treated mice. In contrast, mice treated with a dose-matched IA bolus ATRA demonstrated no clinical benefit. To establish the effect of ATRA on suppressing arthritis. IA ATRA-encapsulated PLGA MP was compared with IA injection of PLGA MPs without ATRA (PLGA-Blank MPs) in SKG mice. Both groups had an average score of 3.5 on day 14 prior to treatment, similar to the results reported above (FIG. 3G). Clinical scores decreased in mice following treatment with a single IA-injection of 2 µg ATRA-encapsulated PLGA MPs, four days (D18: 3.1±0.3) and one week (D21: 2.5±0.4) post-treatment and remained stable until the study endpoint (D35: 2.2±0.9). The scores were significantly lower than those in PLGA-Blank MP treated mice measured at the same timepoints (D18: 4.0±0.5, D21: 4.4±0.8. D35: 4.7±1.0). In contrast to the ATRA-encapsulated PLGA MP-treated mice, the clinical scores for the PLGA-blank MP-treated mice continued to increase over the duration of the study. To assess if there was a dose dependent effect of ATRA in vivo a subset of mice received a higher dose, either 20 µg or 200 µg of ATRA-encapsulated PLGA MPs. Clinical scoring of all groups treated with ATRA-encapsulated PLGA MPs was comparable (FIG. 6A). The improvement in clinical score and ankle thickness measurements were quantified in both the ipsilateral and contralateral joints in the above described studies (FIG. 3H-J, FIGS. 6B and C). Ankle thickness of the hind paws in 2 µg ATRA-encapsulated PLGA MPs-treated mice remained stable or decreased following treatment. In contrast, clinical scores increased comparably in both the ipsilateral and contralateral ankles of the IA bolus ATRA and PLGA-Blank MPs-treated mice.

Figure 4A:
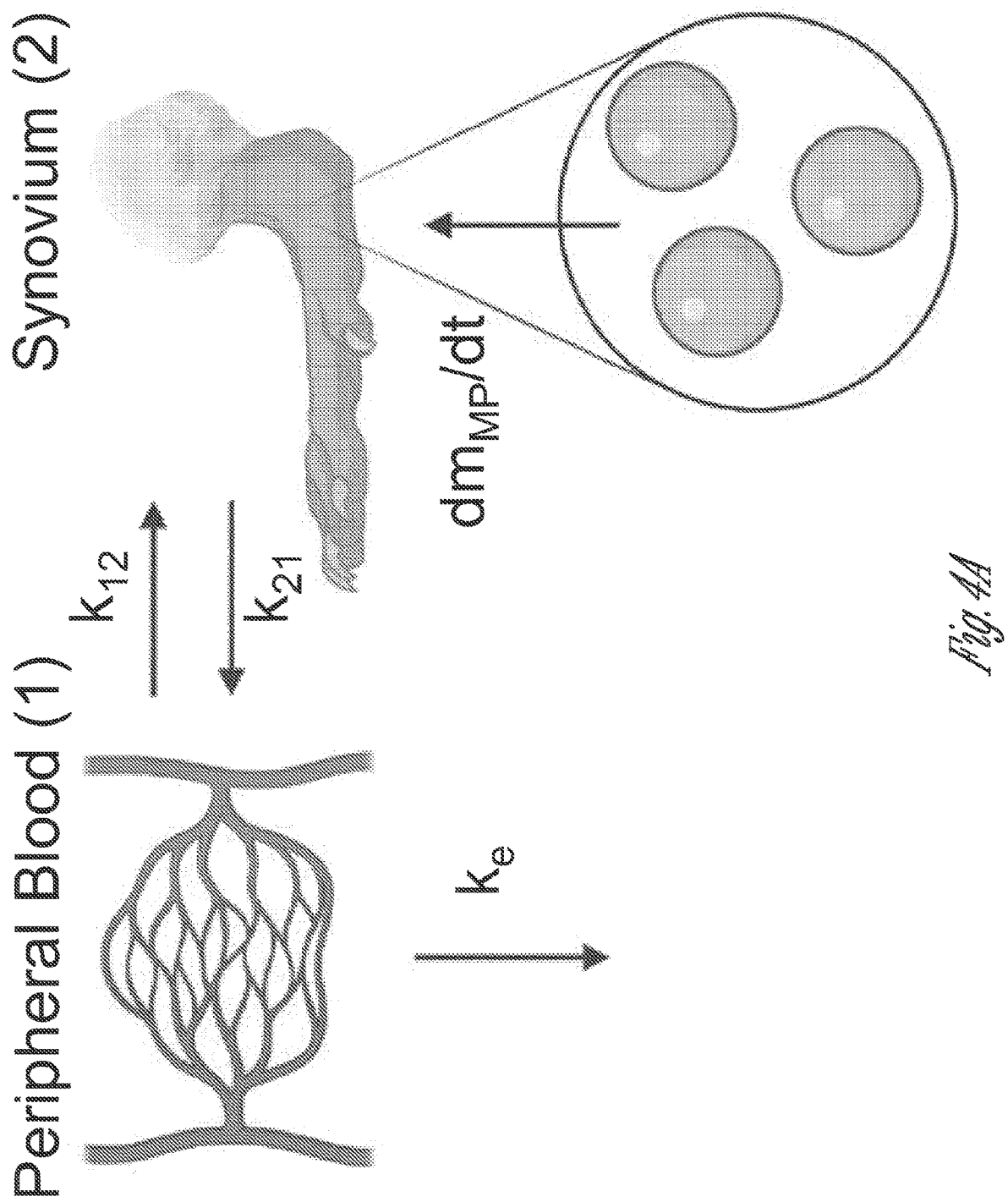
Figure 4C:
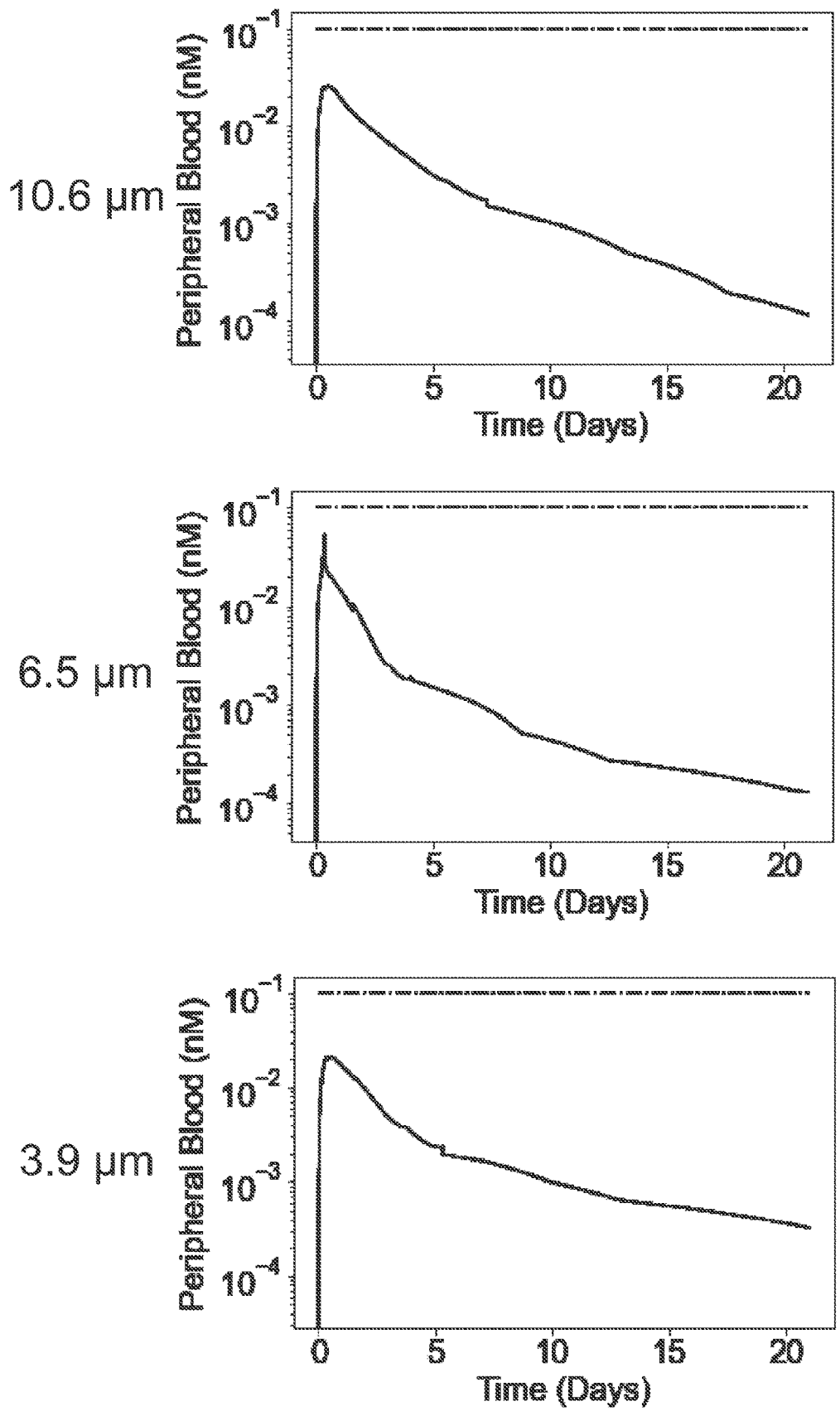
Figure 4D:
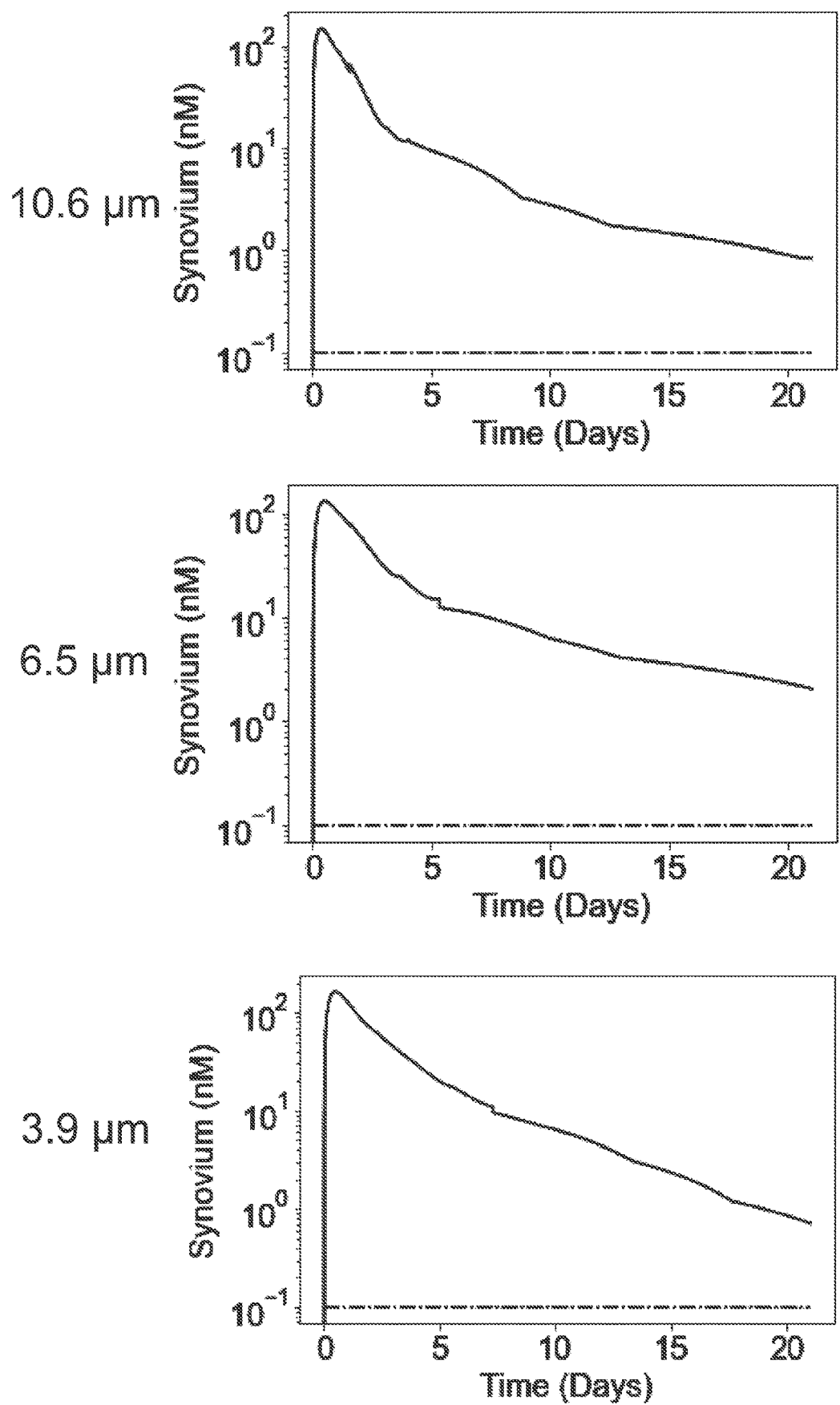
Figure 5A:
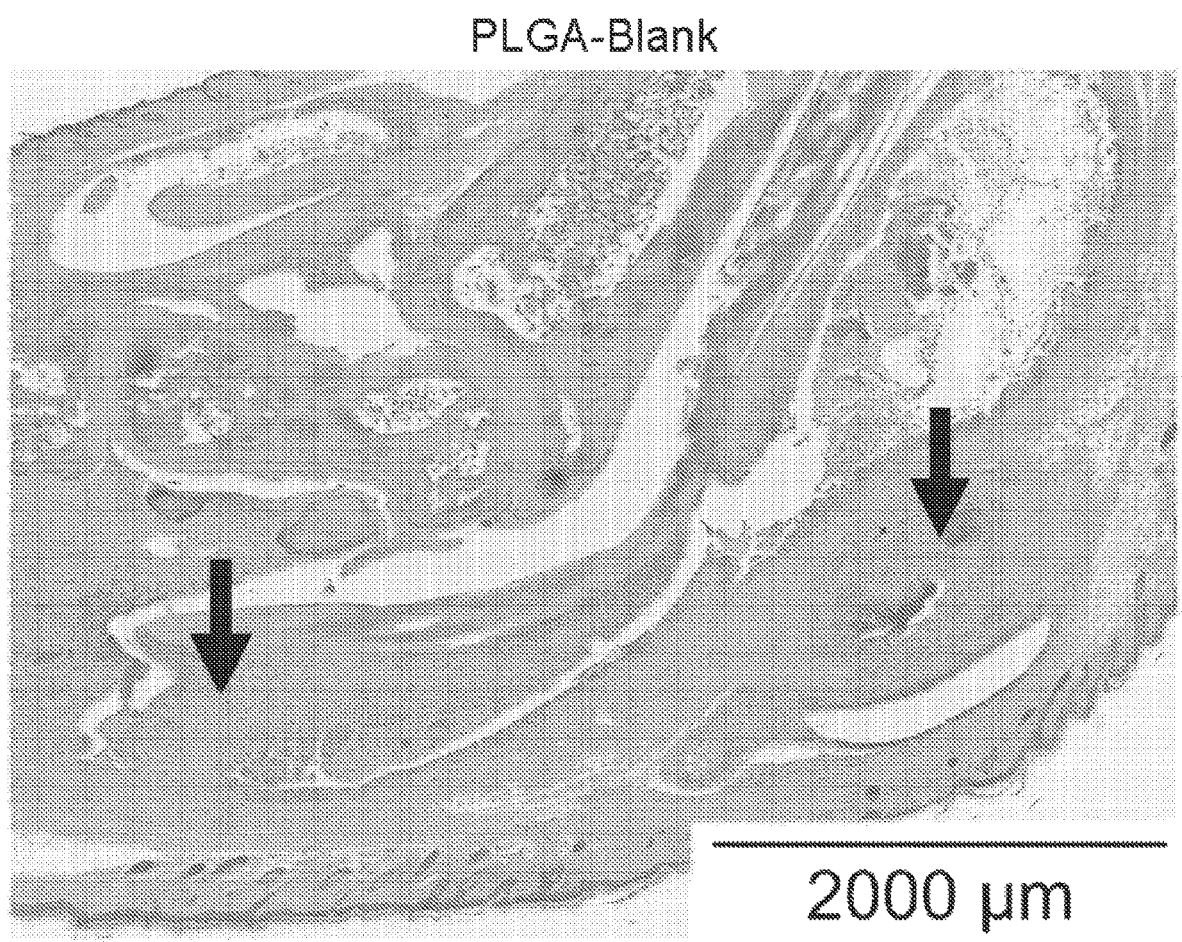
FIG. 5A-i illustrates an enhanced chondroprotection and reduced immune cell infiltration in ATRA-encapsulated PLGA MPs treated mice.
Figure 5B:
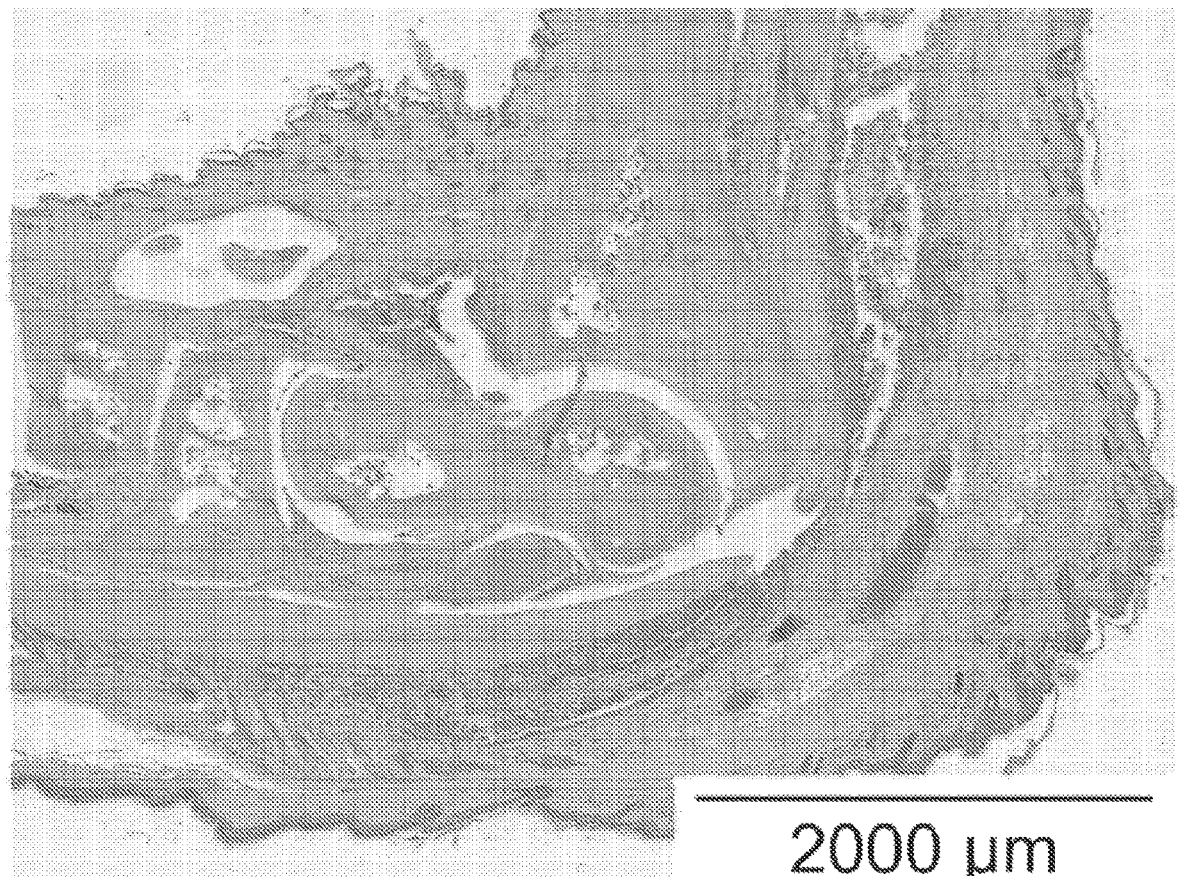
Figure 5C:
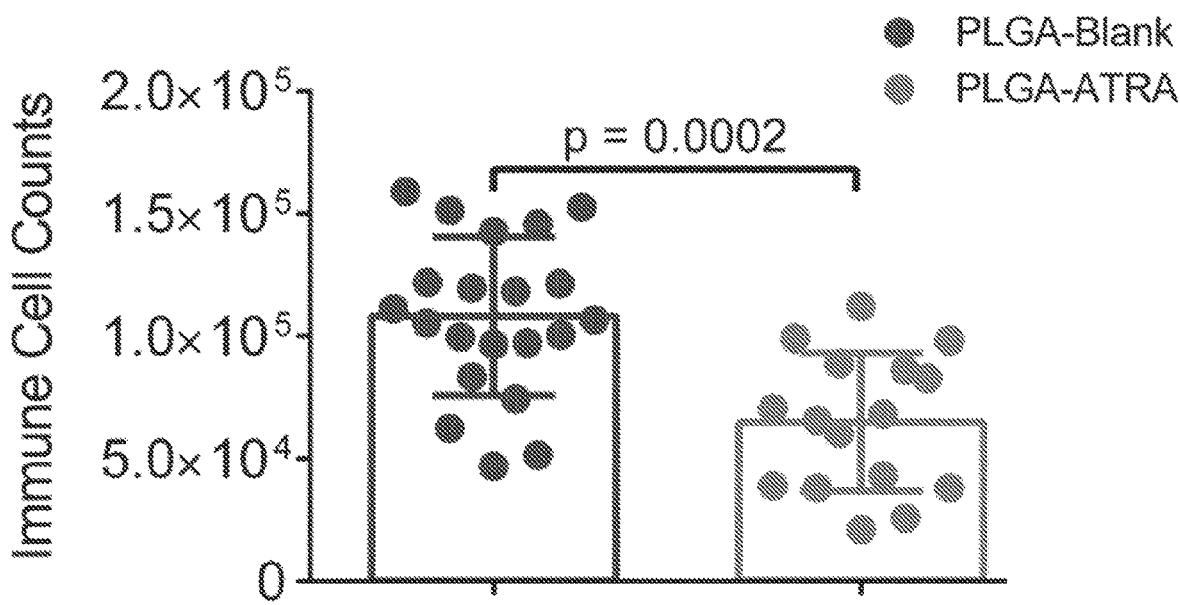
Figure 5D:
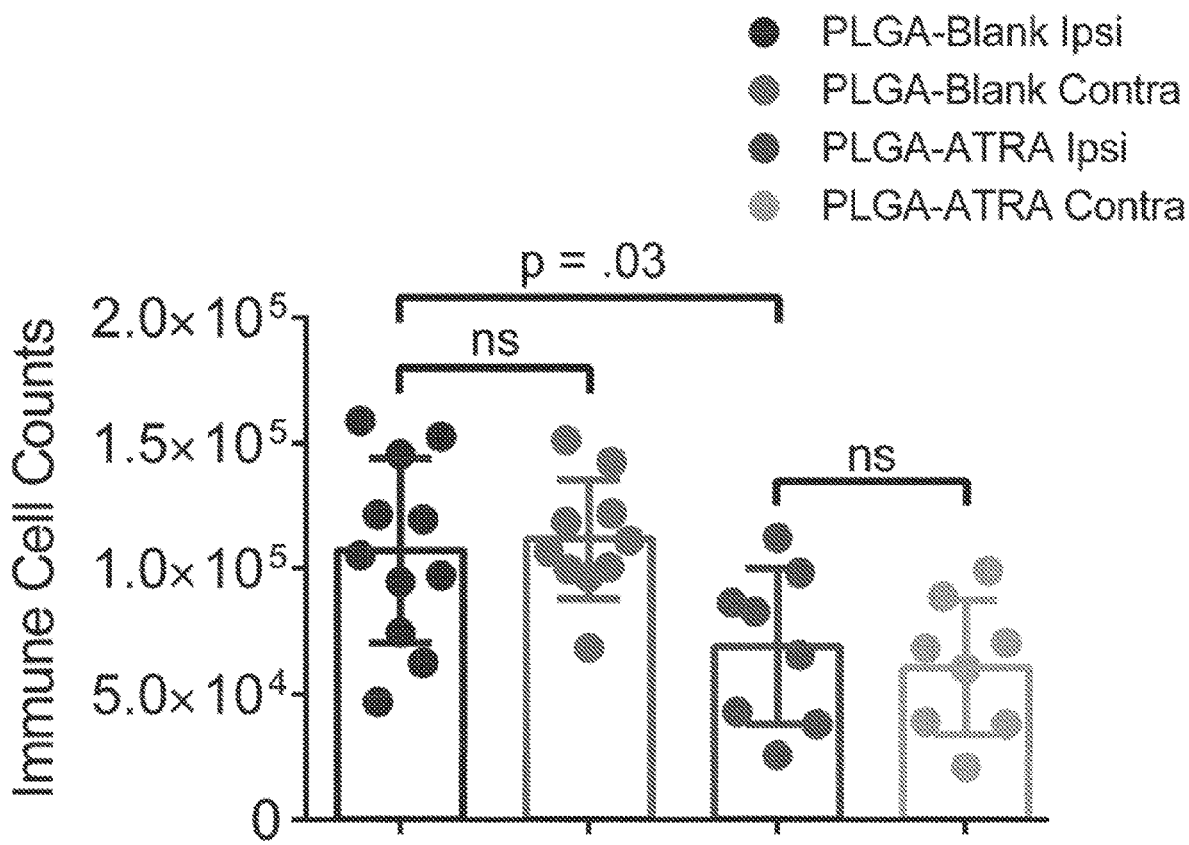
Figure 5F:
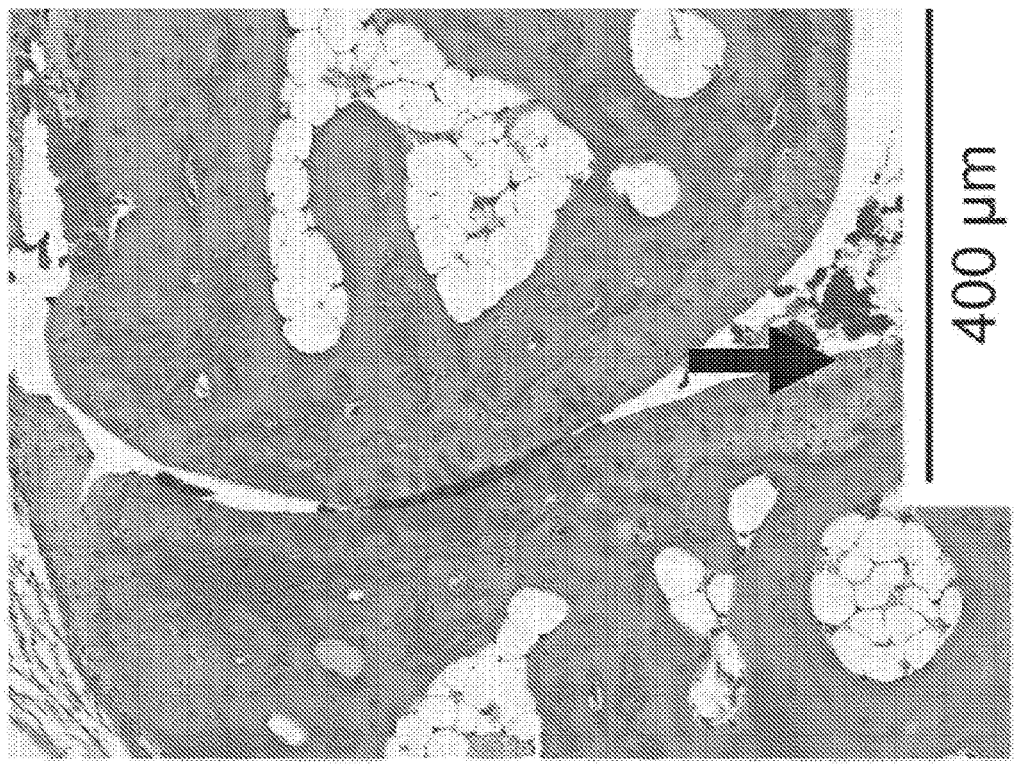
Figure 5E:
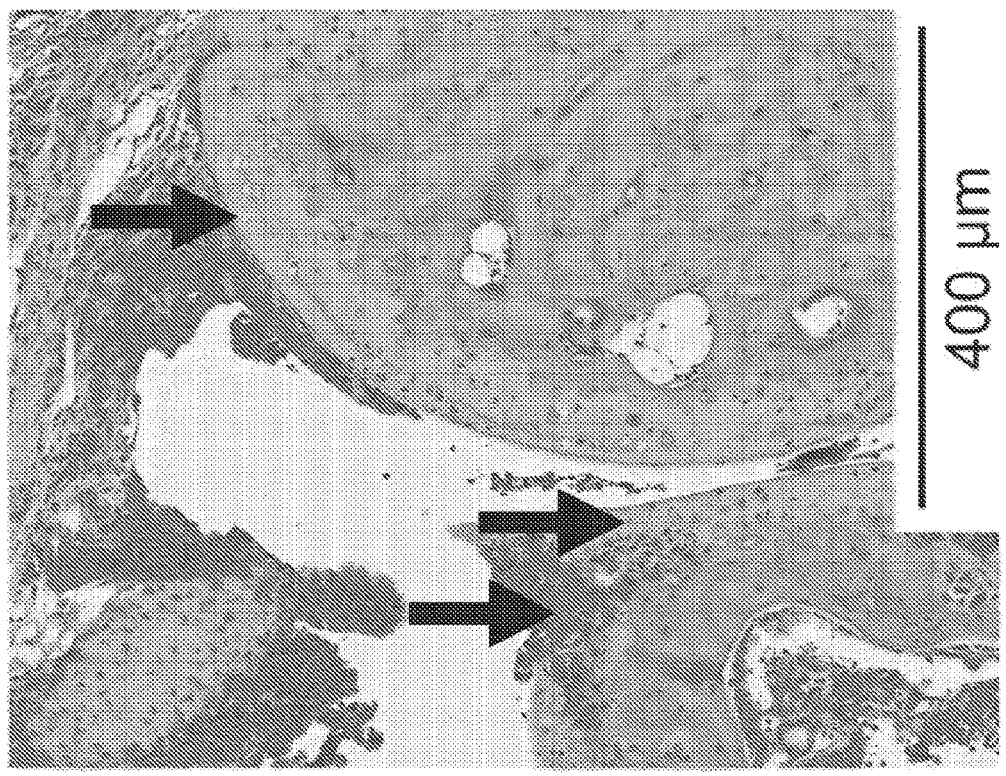
Figure 5G:
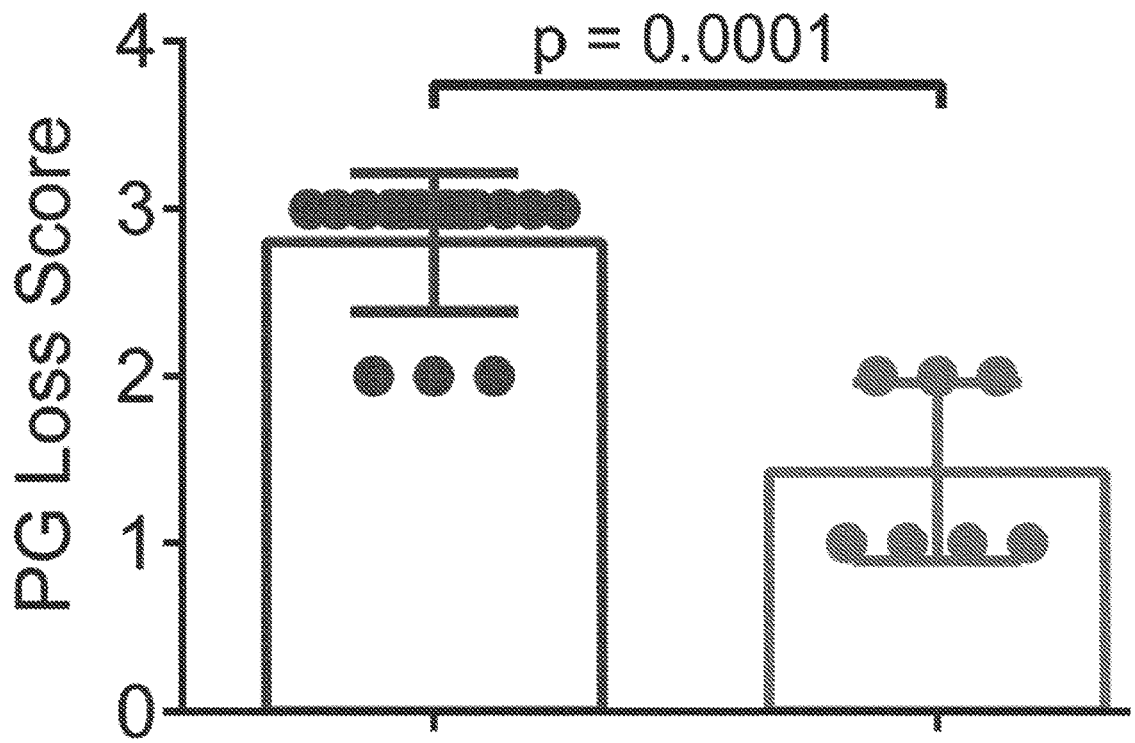
Figure 5H:
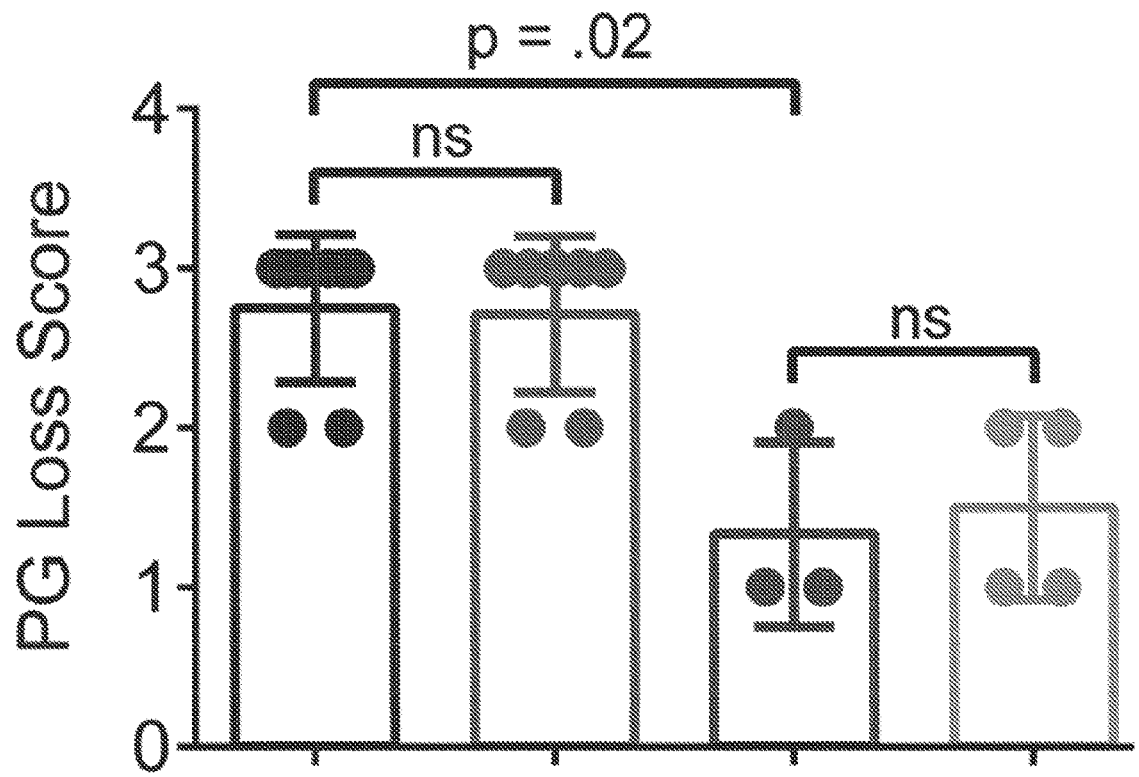
Figure 5I:
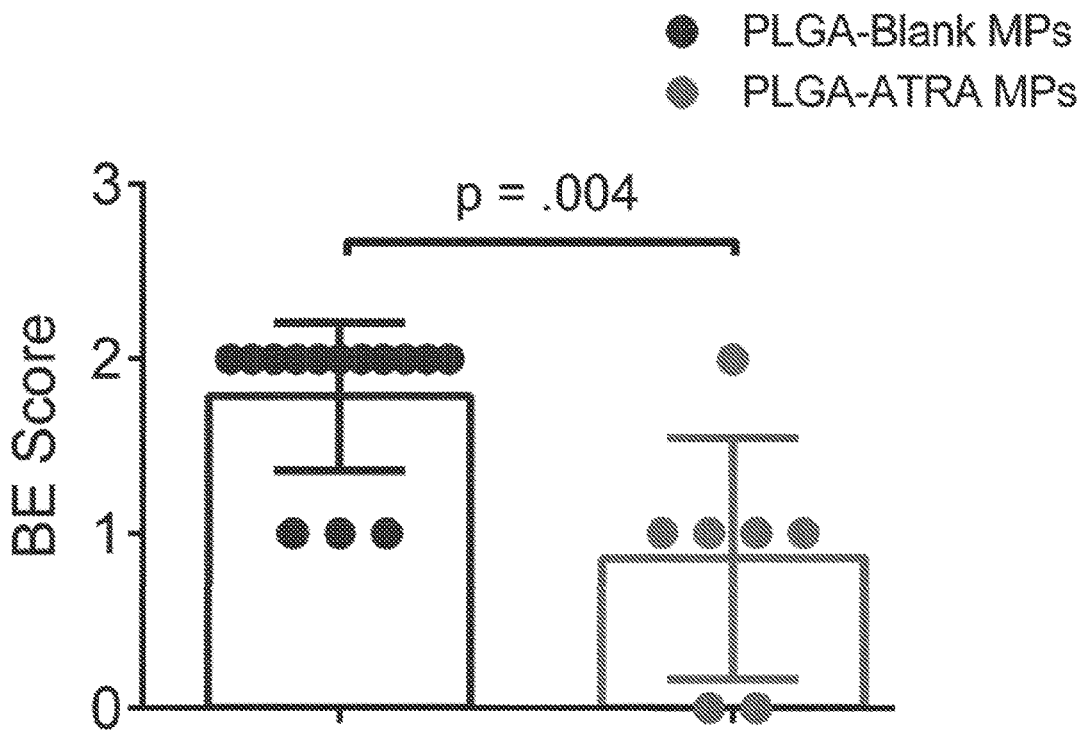
Figure 5J:
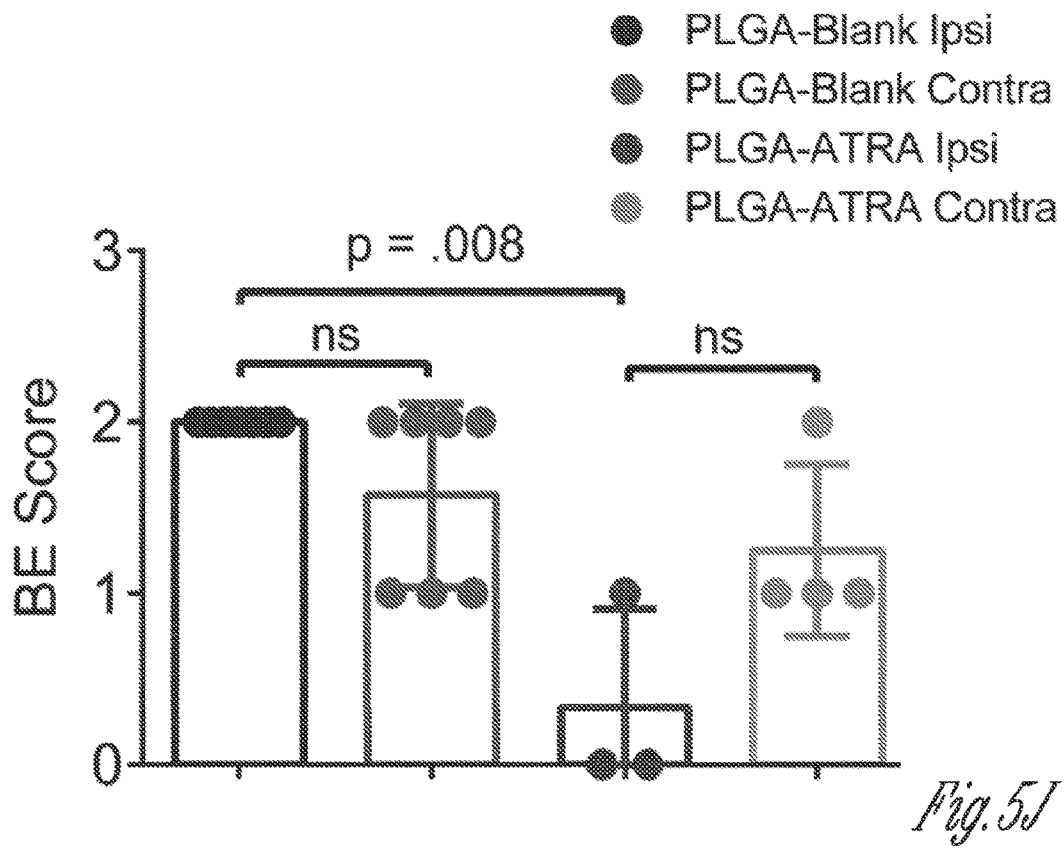

Example 4. ATRA-Encapsulated PLGA MPs Decrease Synovial Infiltrates, Cartilage Damage and Bone Erosion To assess bone and tissue erosion in arthritic SKG joints, the ipsilateral ankles of mice were treated with either PLGA-Blank or ATRA-encapsulated PLGA MPs. Contralateral ankles of the mice received a sham injection of phosphate buffered saline in both treatment groups. Mice were processed for histology after sacrifice on day 35. Hematoxylin and eosin (H&E) staining of arthritic ankle sections showed that the cellularity in the joints of ATRA-encapsulated PLGA MPs-treated mice was reduced compared to joints from PLGA-Blank MPs-treated mice (FIG. 5A). Inspired by the guidelines recently published for Standardized Microscopic Arthritis Scoring of Histological sections ("SMASH") scoring of mouse collagen-induced arthritis ("CIA"), computer-aided algorithms were generated in the QuPath software, using default settings for tissue thresholding and cell detection/classification, to facilitate quantification of cell infiltrates. Cartilage proteoglycan (PG) loss and bone erosion (BE) scoring was performed on SMASH-recommended oriented ankle joint sections. Ankles from mice that treated with ATRA-encapsulated PLGA MPs had significantly reduced numbers of immune cells relative to mice that received PLGA-Blank MPs (FIG. 5B). The degree of synovial inflammation and infiltration were comparable between the contralateral and ipsilateral hind joints of the same treatment groups (FIG. 5C). Safranin-O staining of ankle sections from PLGA-Blank MP-treated mice was used to score proteoglycan (PG) loss and bone erosion (BE), which were 2.8±0.4 and 1.8±0.4, respectively (FIGS. 4D and E). The PG and BE scores for the 2 µg ATRA-encapsulated PLGA MPs treated mice were 1.4±0.5 and 1.0 f 0.8, respectively. The PG and BE scores for the 20 and 200 µg ATRA-encapsulated PLGA MPs treated mice were comparable to the scores of the 2 µg ATRA-encapsulated PLGA MPs-treated mice (data not shown). These results confirmed the ATRA-encapsulated PLGA MPs conferred protections against BE and PG loss in both ipsilateral and sham-injected contralateral ankles in treated mice.

Example 5. ATRA-Encapsulated PLGA MPs Promote $T_{reg}$ Cell Stability In Vitro

Figure 7A:
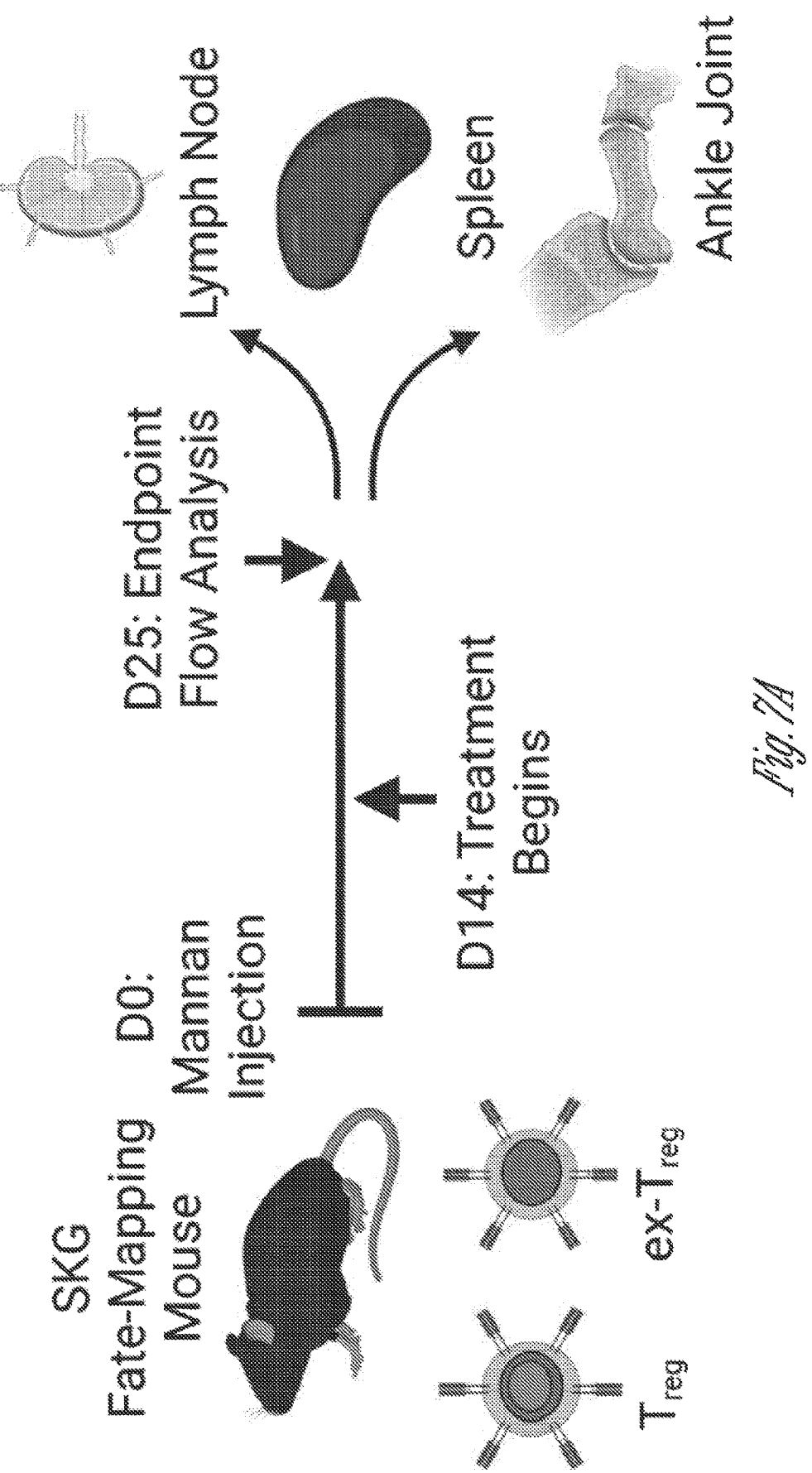
FIGS. 7A-D depict the induction of arthritis in fate-mapping mice.
Figure 7B:
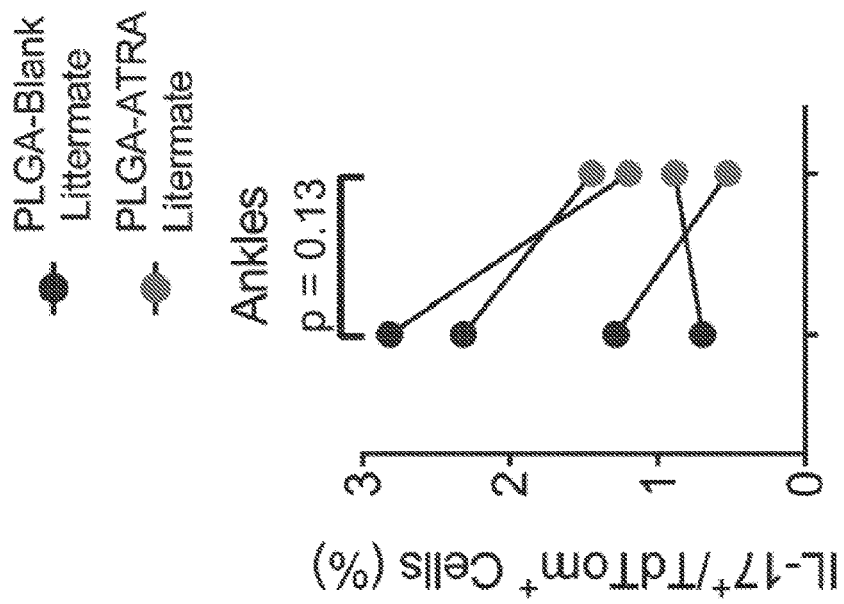
Figure 7C:
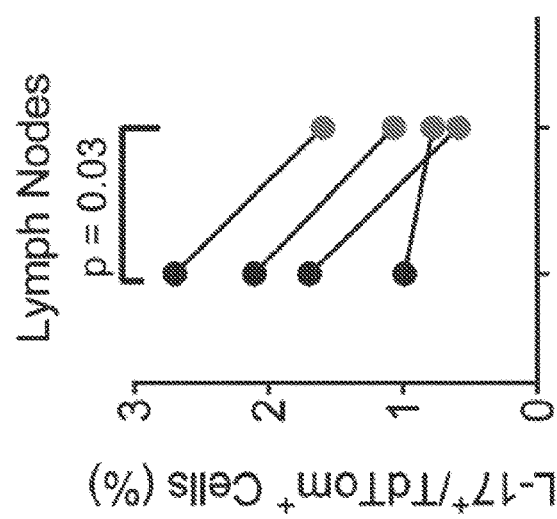
Figure 7D:
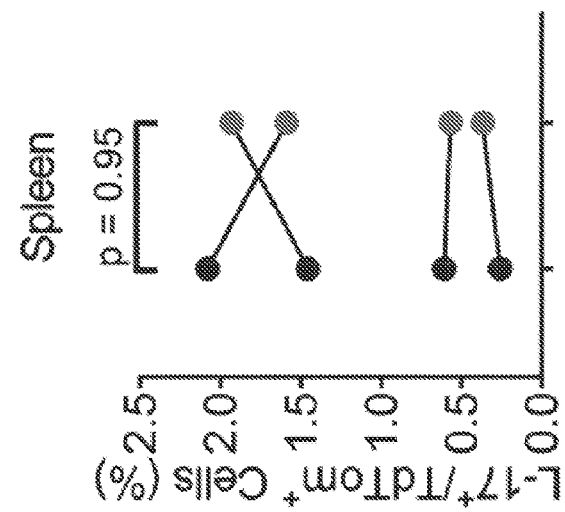

A schematic is shown illustrating the induction of arthritis in fate-mapping mice and subsequent treatment and endpoint (FIG. 7A) Fate-mapping mice where we feed the tamoxifen which induces expression of a TdTomato fluorescent protein in any organs that contain $T_{reg}$ cells at the time of tamoxifen feeding. These cells continue to express the TdTomato fluorescent protein until they die and thus show all organs with $T_{reg}$ cells even if the cells are destabilized into an ex-$T_{reg}$ (loses FoxP3 expression and gains IL-17 expression), i.e., "mapping" the fate of the $T_{reg}$ cells. IL-17 expression was quantified by tdTomato+ CD4+ T cells isolated from the spleen (shown in FIG. 7B), draining lymph nodes (shown in FIG. 7C), or ankles (shown in FIG. 7D) of fate-mapping mice. Paired points represent littermates, wherein one littermate was treated IA with PLGA-Blank MPs, and the other littermate was treated IA with ATRA-encapsulated PLGA MPs. Mice treated with ATRA-encapsulated PLGA MPs contain less $T_{reg}$ cells that have destabilized into IL-17 expressing cells in ATRA-encapsulated PLGA MPS treated ankles and draining lymph nodes, but not the spleen.

Figure 8A:
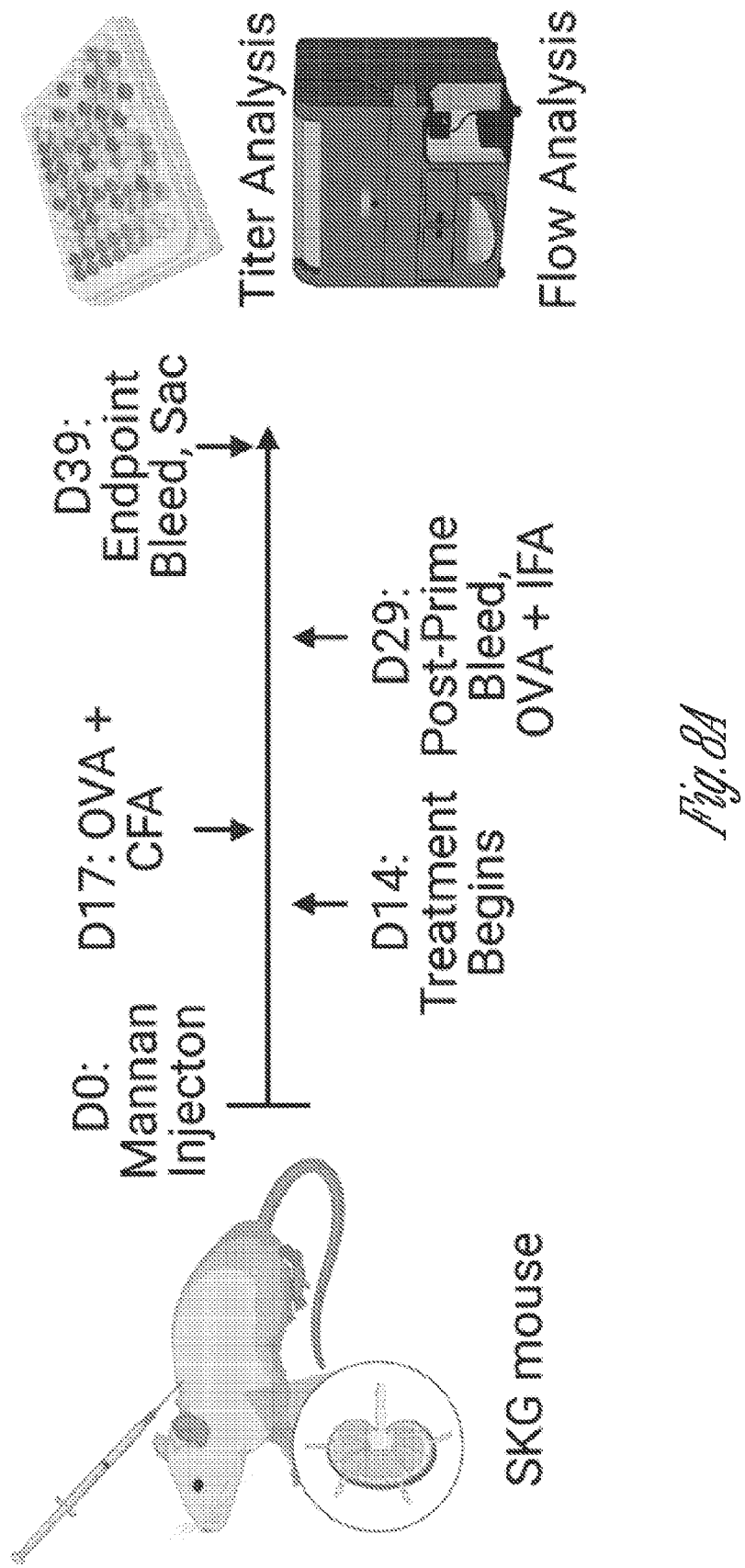
FIGS. 8A-F illustrate that ATRA-encapsulated PLGA MPs does not impair systemic immune response against an arthritis-irrelevant antigen. FIG. MA is a schematic depicting an ovalbumin (OVA) vaccination assay in arthritic SKG mice using an initial immunization (prime) with complete Freund's adjuvant (CFA) and a subsequent booster immunization (boost) with incomplete Freund's adjuvant (IFA) 10 days later.
Figure 8B:
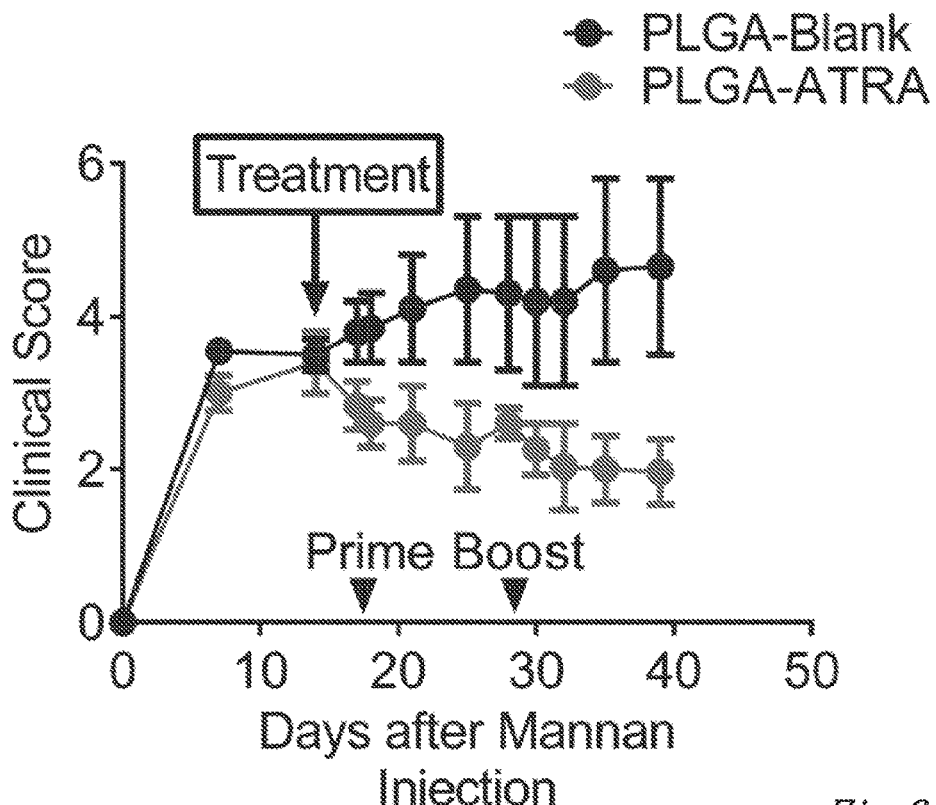
Figure 8C:
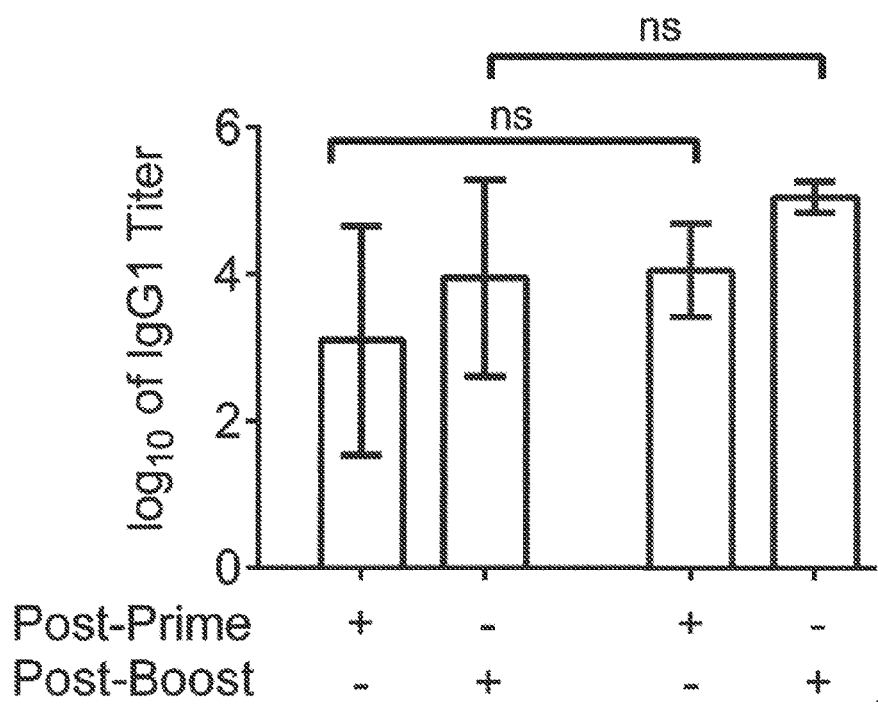
Figure 8D:
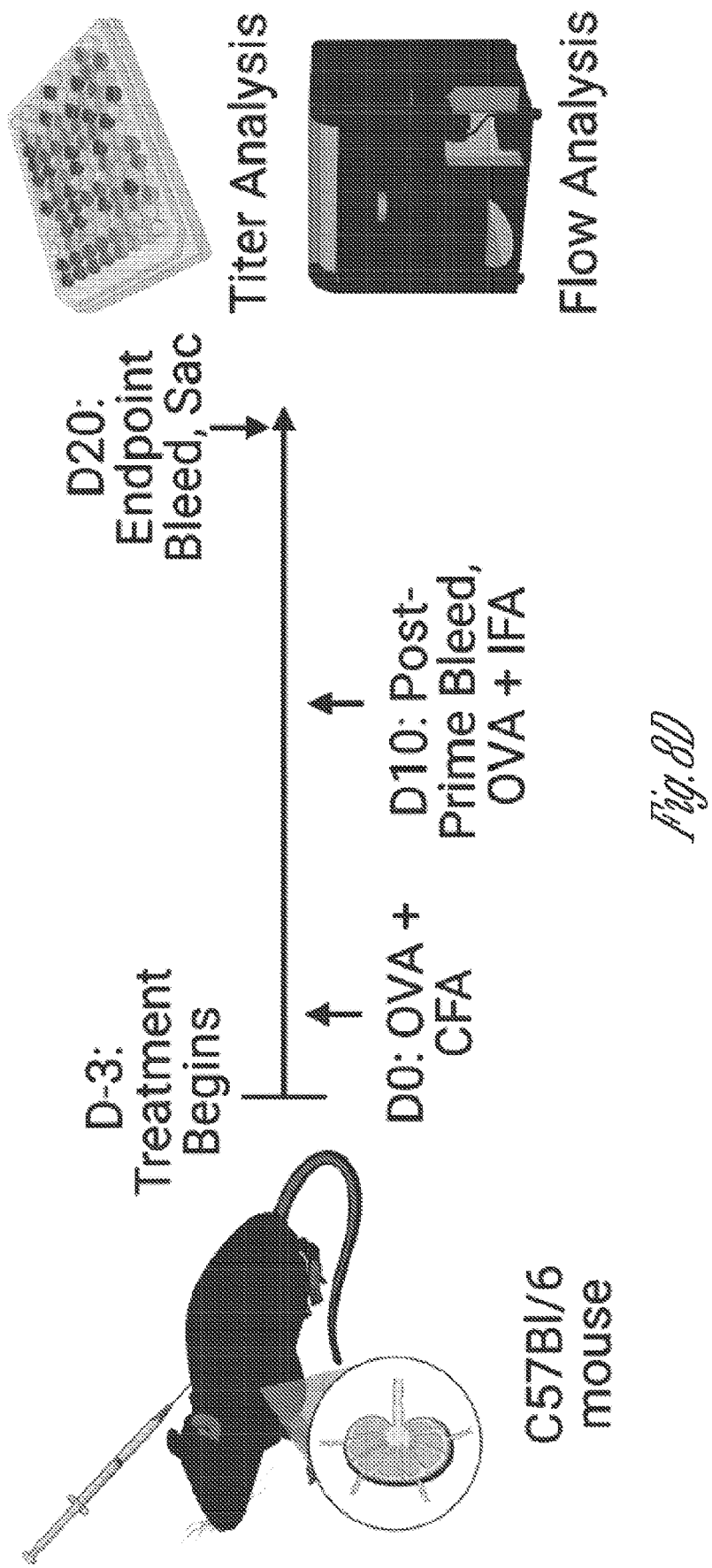

Example 6. ATRA-Encapsulated PLGA MPs Treatment is Effective without Generalized Immunosuppression To assess if the local $T_{reg}$ cell enhancement induced by IA ATRA-encapsulated PLGA MPs results in systemic inhibition of T cell-mediated responses, the response of arthritic SKG mice treated with either 2 µg PLGA-Blank MPs or 2 µg ATRA-encapsulated PLGA MPs to immunization with a T cell dependent antigen was measured. The primary immunization consisted of subcutaneous injection of an emulsion of ovalbumin (OVA), an SKG arthritis-irrelevant antigen, in complete Freund's adjuvant three days post-1A injection, followed by a booster immunization ten days later consisting of OVA in incomplete Freund's adjuvant (FIG. 6A) As this route of OVA immunization is known to produce a strong anti-OVA IgG1 antibody response, we quantified the post-priming and post-booster anti-OVA IgG1 antibody concentration in the peripheral blood. Healthy non-immunized SKG mice without arthritis were used to quantify the baseline immune response. Arthritis progression, as assessed by clinical scoring, was not affected by either the prime or boost immunization in both PLGA-Blank MPs and ATRA-encapsulated PLGA MPs mice and was similar to non-immunized mice (FIG. 8B). Plasma anti-OVA IgG1 antibody titers were comparable between PLGA-Blank MP and ATRA-encapsulated PLGA MPS-treated mice, and both groups produced high antibody titers, whereas those in non-immunized mice were below the limit of detection (FIG. 8C). Flow cytometry of the spleen and draining lymph nodes confirmed that the total number and fraction of Th1 (Live+CD4+IFNγ+) and Th2 (Live+CD4+IL-4+) cells was comparable between the PLGA-Blank MPs- and ATRA-encapsulated PLGA MPs-treated groups (data not shown).

To quantify the effect of IA ATRA-encapsulated PLGA MPs on arthritis-irrelevant T cell suppression we leveraged OVA-specific tetramers available for quantifying T cells in H2b-background mice and conducted the aforementioned immunization study in healthy C57BL/6J (B6) mice (FIG.

Figure 8E:
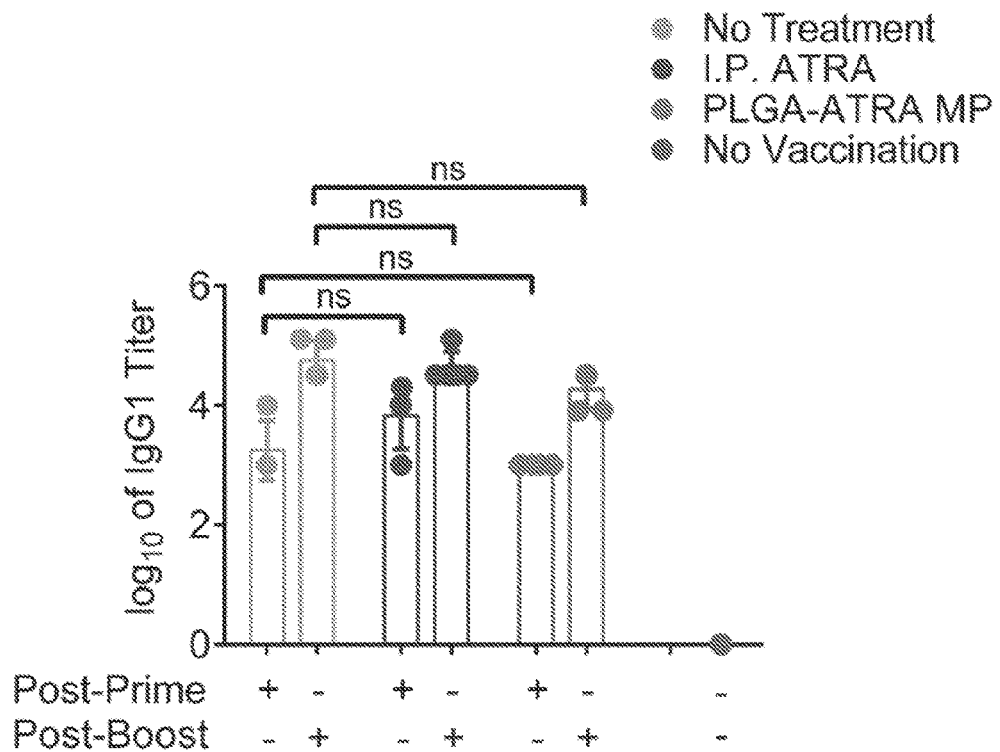
Figure 8F:
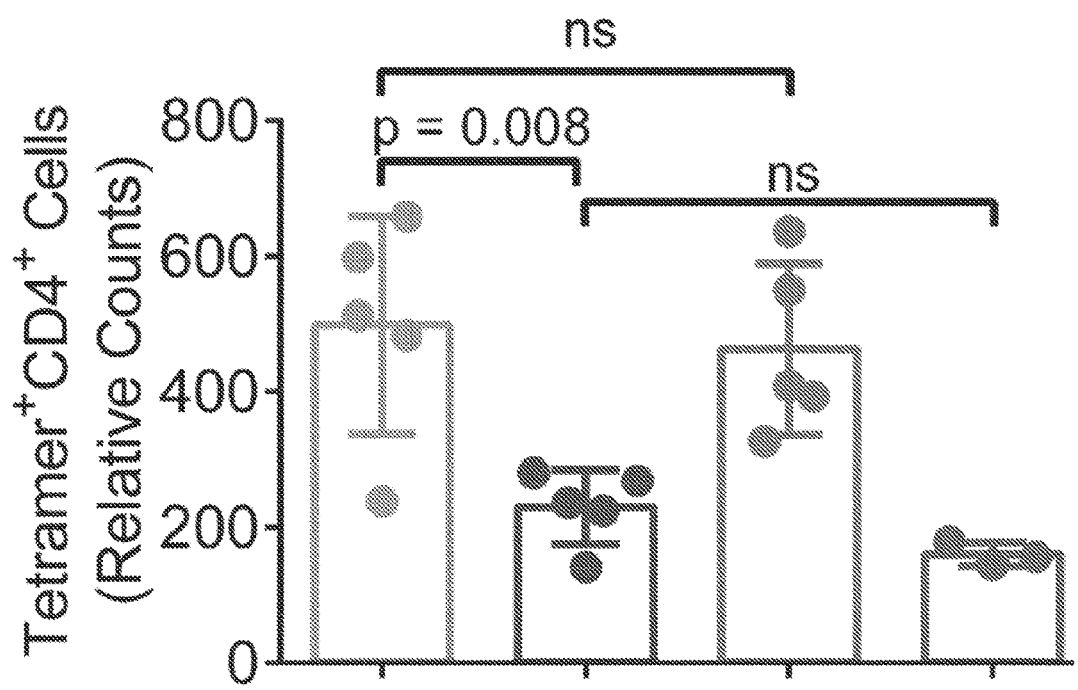

8D). Systemically administered ATRA was delivered as a daily intraperitoneal (i.p.) injection to assess the effect of systemic exposure. The anti-OVA IgG1 response in IA PLGAATRA MPs treated mice was comparable in titer to the response in immunized mice that received no treatment and in mice receiving daily ATRA injections (FIG. 8E). OVA-specific CD4+ T cells, as quantified by I-A(b) QAVHAAHAEIN tetramer staining (NIH Tetramer Core Facility), were significantly lower after daily i.p. administration of ATRA in the spleen, while a single dose of IA injected ATRA-encapsulated PLGA MPs did not impair the antigen specific CD4+ T cell response relative to untreated immunized mice (FIG. 8F).

Figure 9A:
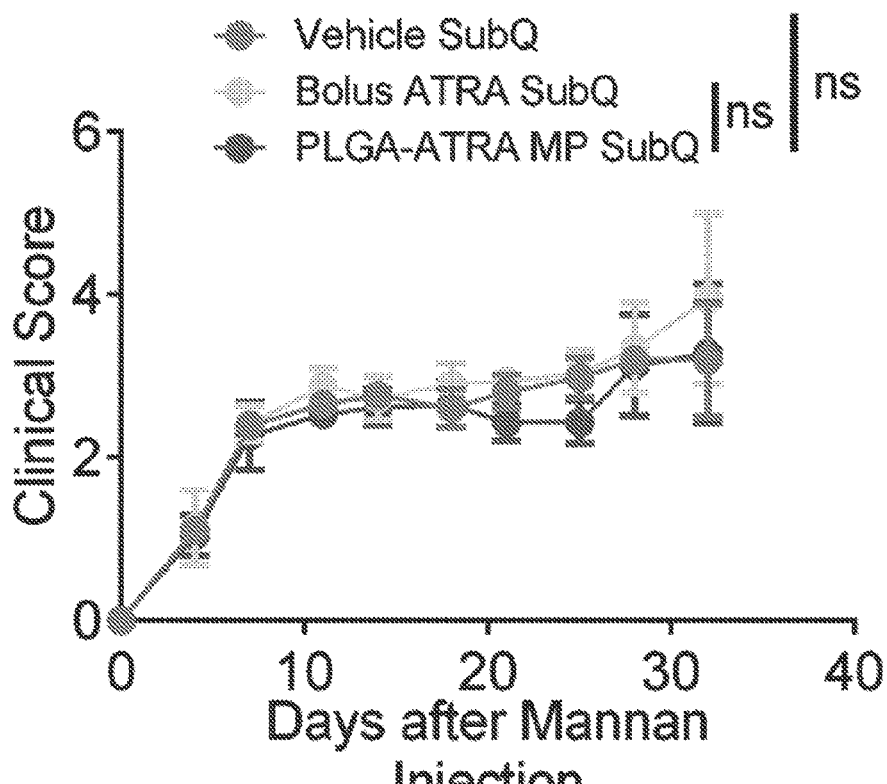
FIGS. 9A-B depict the efficacy of ATRA-encapsulated PLGA MPs via subcutaneous delivery.
Figure 9B:
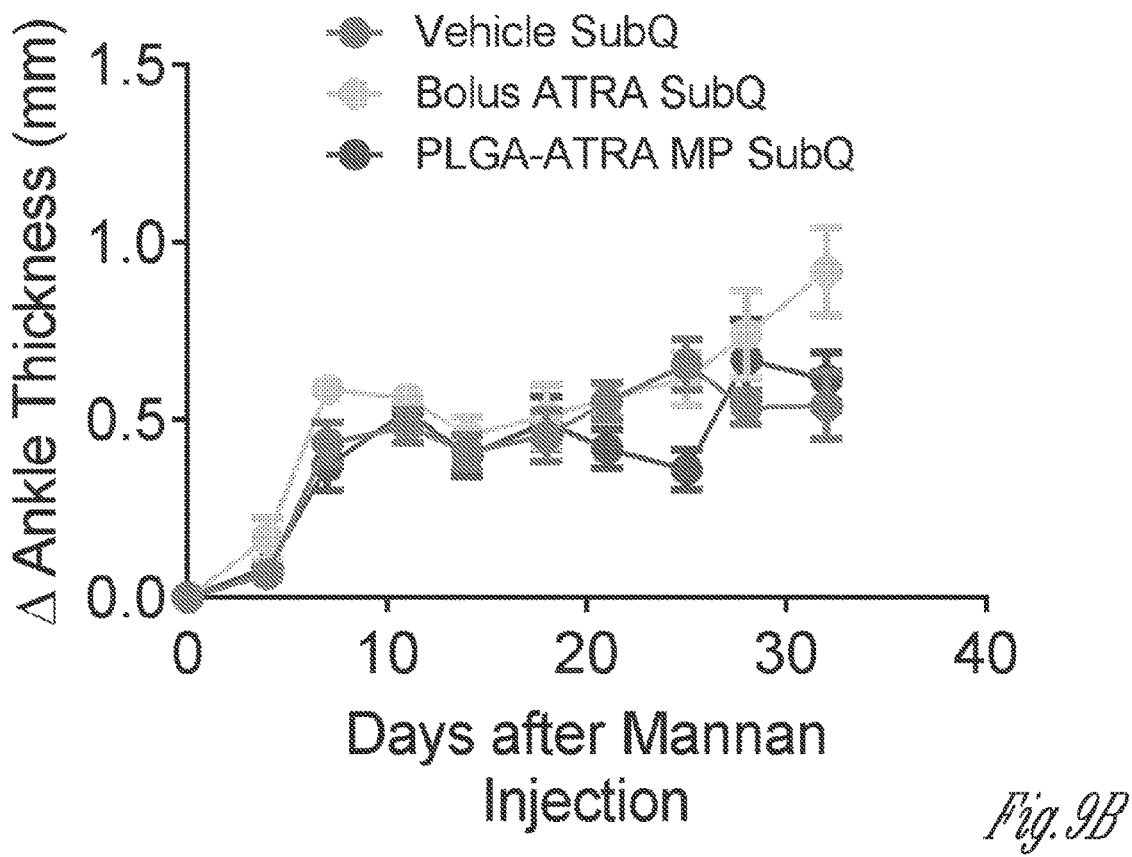

Example 7. ATRA-Encapsulated PLGA MPs and Bolus ATRA do not Improve Clinical Score when Administered Subcutaneously The efficacy of subcutaneously administered ATRA-encapsulated PLGA MPS in treating SKG mice was assessed to determine whether ATRA-encapsulated PLGA MPS act via systemic release, in which case subcutaneous ATRA-encapsulated PLGA MPS treatment would improve disease scores, or if ATRA-encapsulated PLGA MPS treatment acts locally, in which case its delivery to the intra-articular space would improve disease scores. ATRA-encapsulated PLGA MPS, dose-matched Bolus ATRA in corn oil, and vehicle (corn oil) were administered to arthritic SKG subcutaneously between the scapula of SKG mice (FIGS. 9A-B). Neither bolus ATRA nor ATRA-encapsulated PLGA MPs provided improvement in clinical score (FIG. 9A) or ankle swelling (FIG. 9B).

Figure 10A:
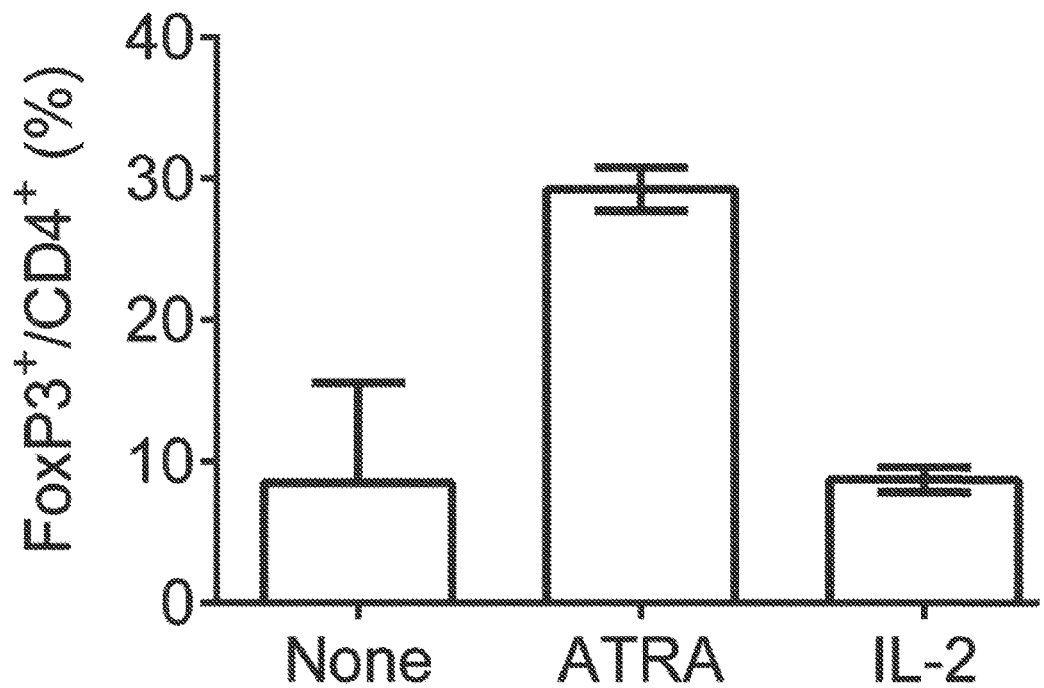
FIGS. 10A-B depict the quantification of FoxP3 or IL-17 expression in CD4+ T cells after a 24-hour pretreatment.
Figure 10B:
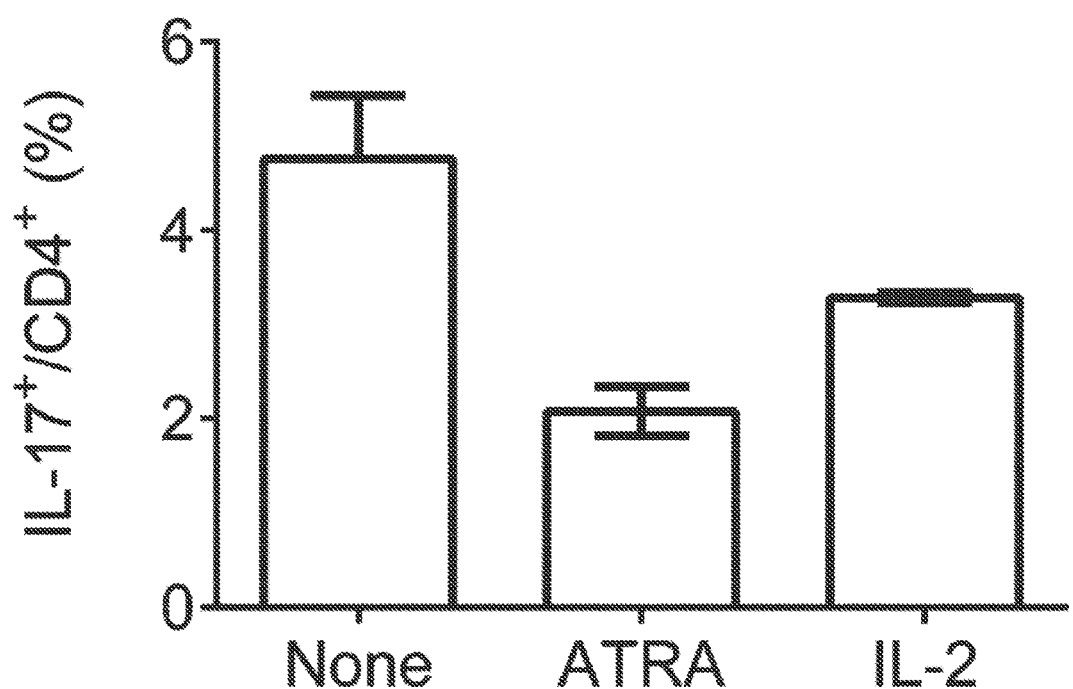

Example 8. Pre-Treatment of CD4+ T Cells with ATRA Increases FOXP3 Expression and Reduces IL-17 Expression after Exposure to Th17 Inducing Conditions FIG. 10A depicts the quantification of FOXP3 expression in CD4+ T cells after 24-hour pretreatment with either nothing (None), 1 nM ATRA (ATRA), or IL-2, followed by removal and washing of the cells, and transfer to Th17 inducing conditions. FIG. 10B depicts quantification of IL-17 expression in CD4+ T cells after a 24-hour pretreatment with either nothing (None), 1 nM ATRA (ATRA), or IL-2, followed by removal and washing of the cells, and transfer to Th17 inducing conditions. Pre-treatment of the CD4+ T cells with ATRA increases FOXP3 expression and reduces IL-17 expression after exposure to Th17 inducing conditions. The example demonstrates that pre-exposure to ATRA at a functional concentration influences CD4+ T cell fate and promotes a $T_{reg}$ phenotype even if ATRA is no longer directly present at a functional concentration.

Figure 11A:
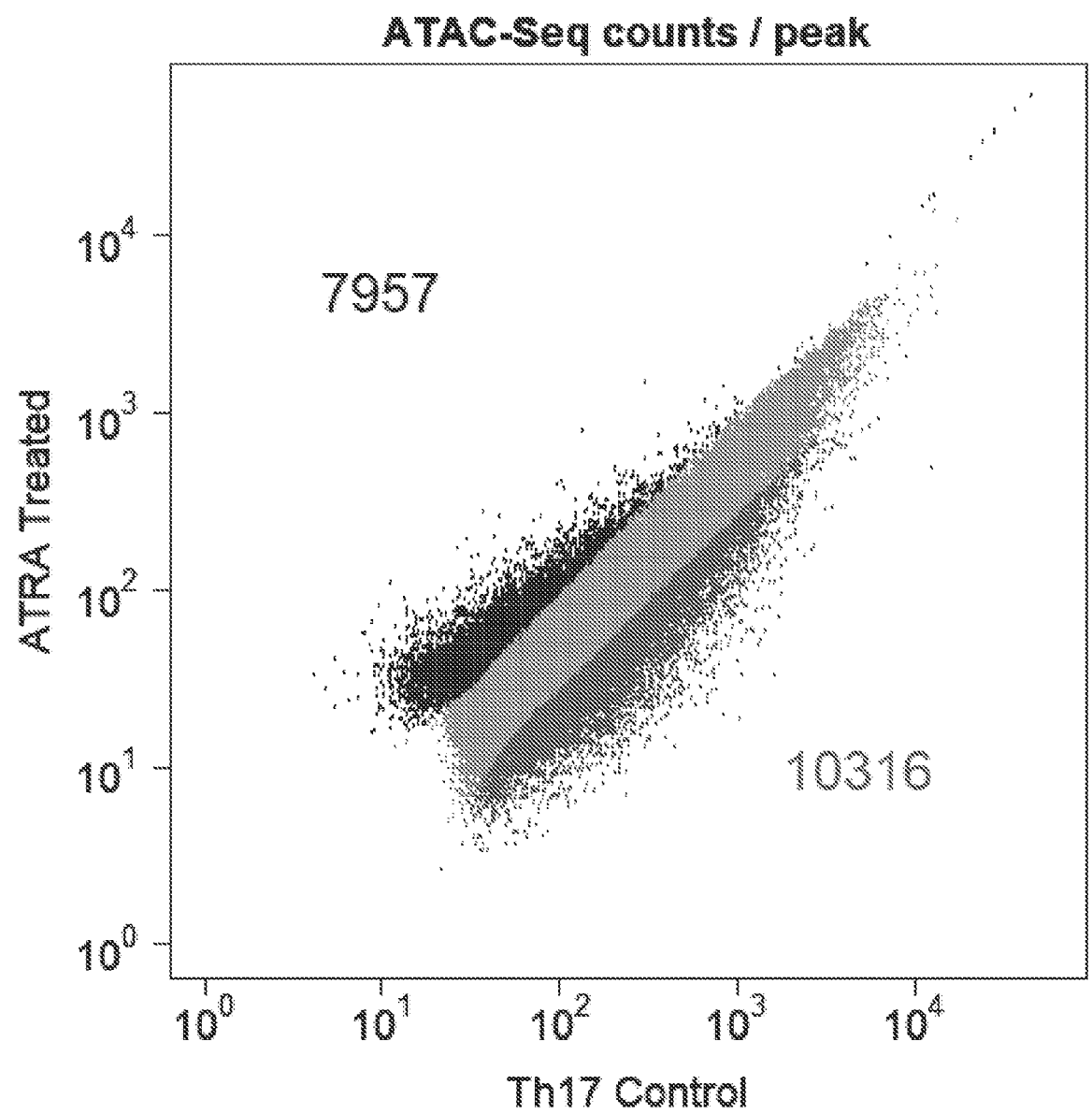
FIGS. 11A-D depict data from an Assay for Transposase Accessible Chromatin (ATAC) sequencing for determining whether ATRA makes epigenetic modifications to cellular DNA.
Figure 11B:
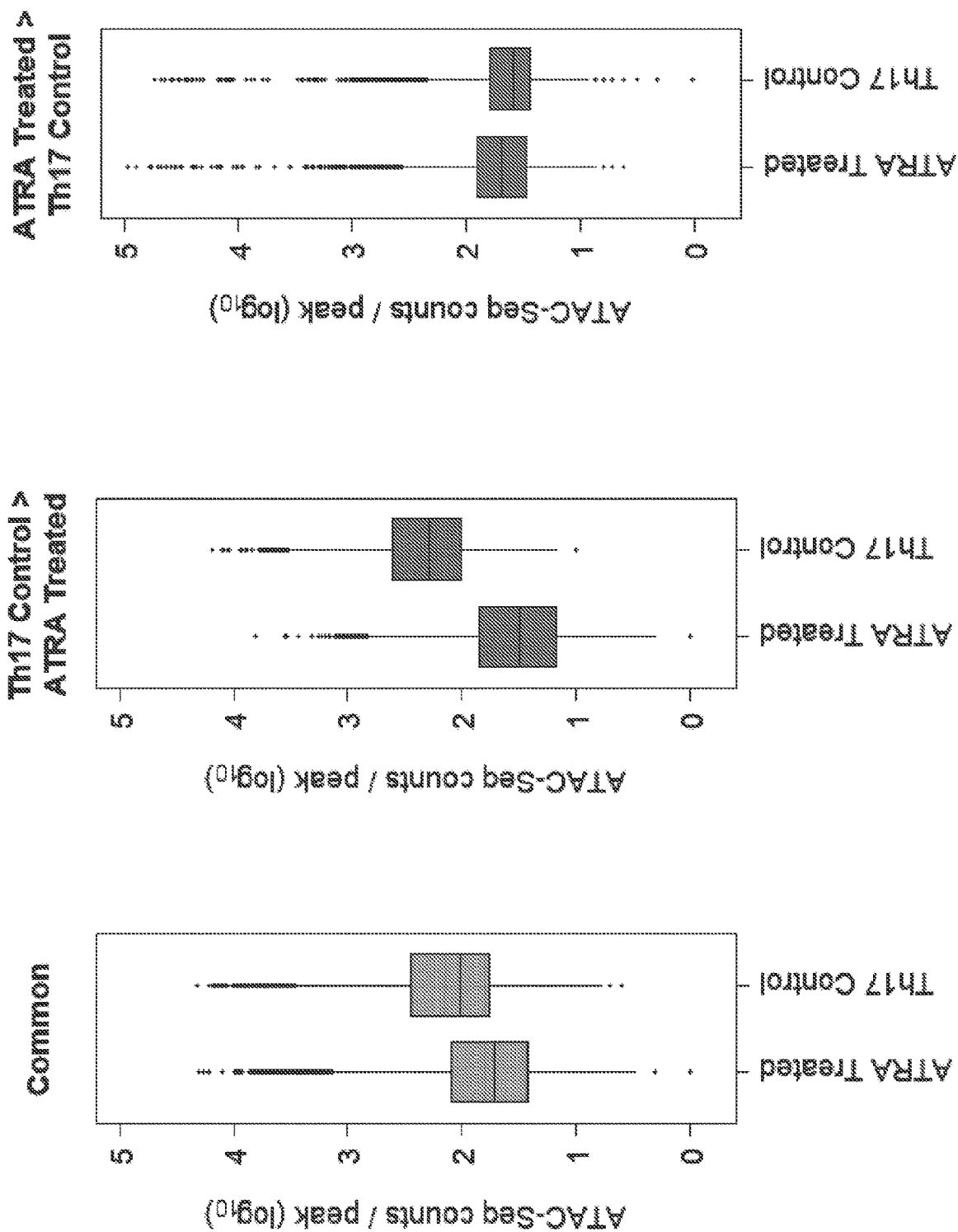

Example 9. ATRA Modulates the Accessibility of Chromatin at $T_{reg}$ and Th17 Relevant Loci Assay for Transposase Accessible Chromatin (ATAC) sequencing assay uses a hyperactive protein to bind and snip DNA in open chromatin regions to probe for the parts of DNA are accessible for transcription. The ATAC assay was performed to determine whether ATRA causes epigenetic modifications to cellular DNA to influence the accessibly of DNA for transcription and, in turn, modulating what a cell's "default" state/programs are. Quantification of differentially accessible regions (DARs) is shown by counts per peak between cells cultured in Th17 inducing conditions with (ATRA Treated) or without (Th17 Control) 1 nM ATRA. (FIG. 11A). Quantification of "differentially accessible" DNA shows that there are 10316 regions in the DNA that are more open in the Th17 control and 7957 regions in the DNA that are more open in the ATRA treated cells. Quantification of the counts per peak of the three groupings of DARs (Common, Th17 Control>ATRA Treated, ATRA Treated>Th17 Control) shows the spread in the differences in counts per peak of the different regions (FIG. 11B).

Figure 11C:
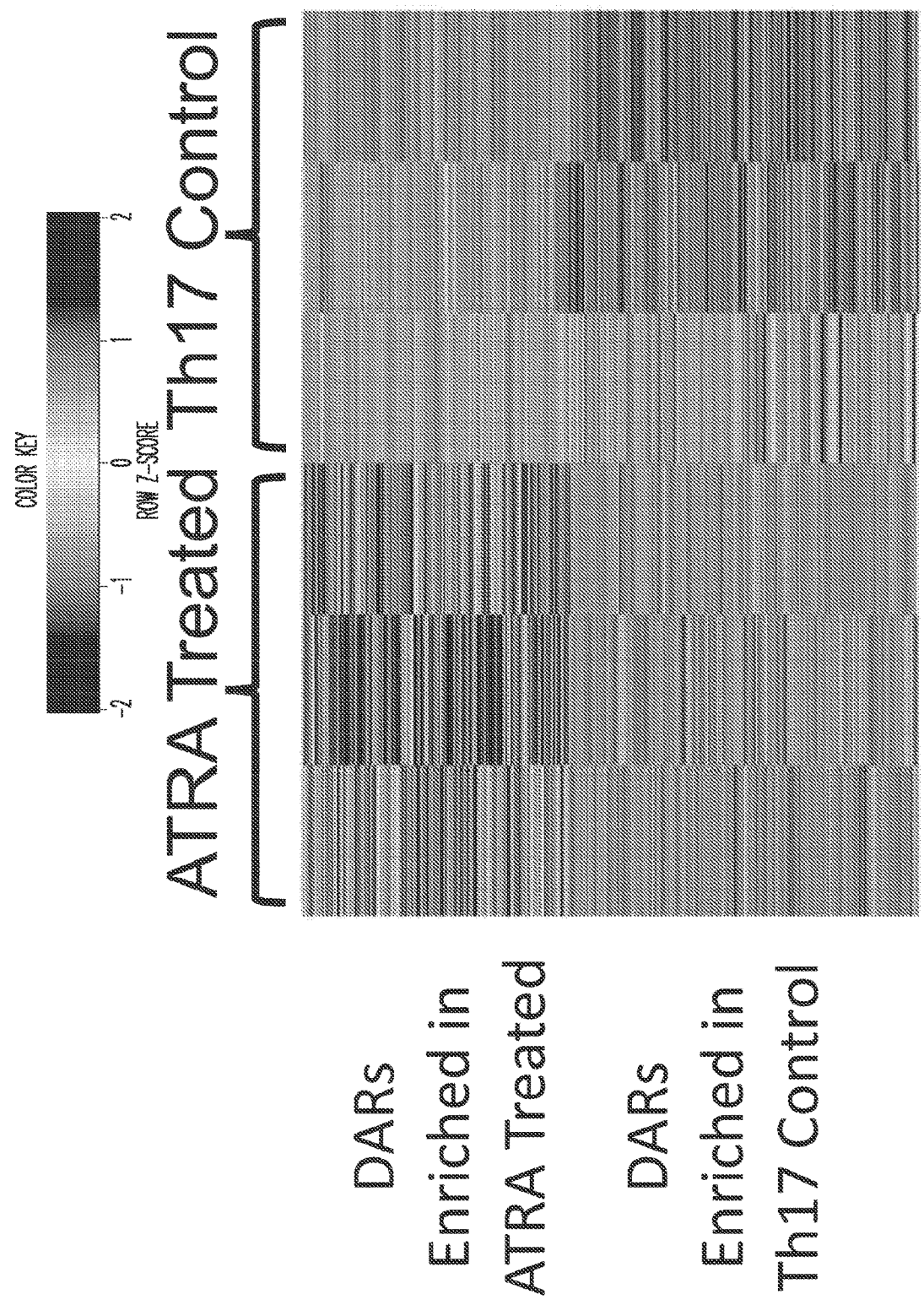
Figure 11D:
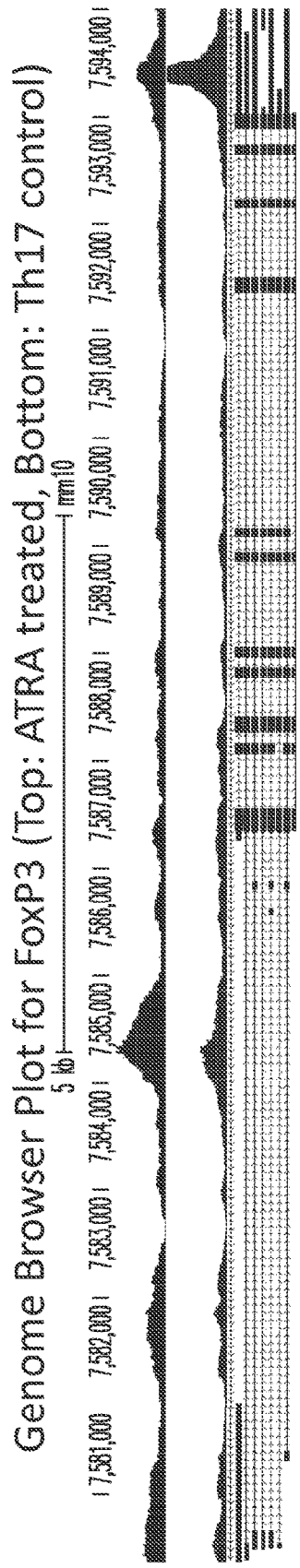
Figure 11D:
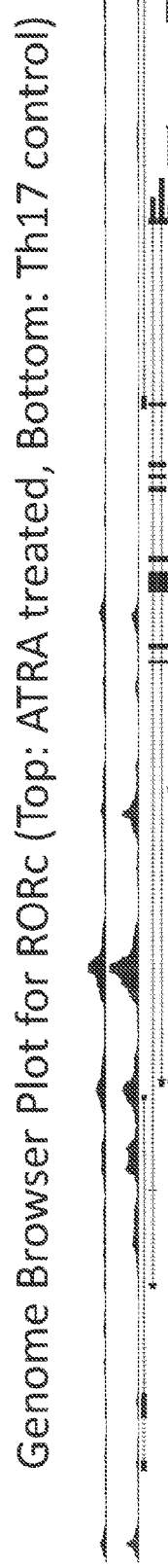
Figure 11D:
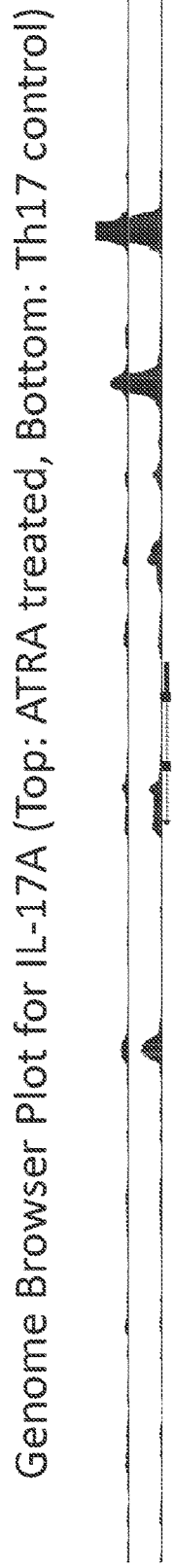
Figure 11D:
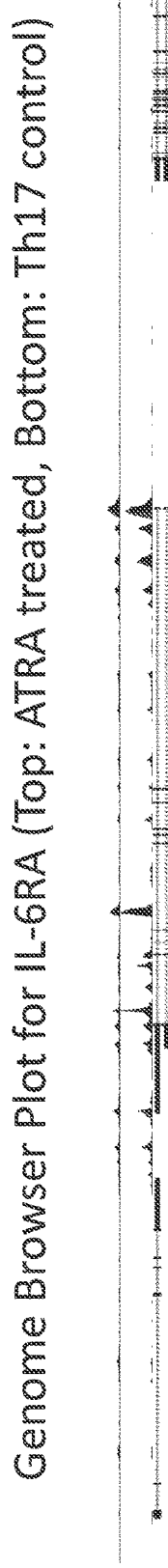

FIG. 11C is a heatmap of all DARs grouped in rows by those enriched in the ATRA treated group or those enriched in the Tb17 Control group. Heatmapping was performed by determining the z-score of the DAR in a given sample as compared to the row. A Genome browser plot for Th17 and $T_{reg}$ associated genes is shown (FIG. 11D). The size of the peaks corresponds to the number of reads, so the bigger the peaks are the more accessible that region of DNA is. Four plots are shown, corresponding to highly relevant genes (FoxP3, RORc, IL-17A, and IL-6RA), and the average peaks for both the ATRA Treated cells and Th17 Control cells are visualized (FIG. 11D. You can see in the FoxP3 that the blue peaks are larger, indicating that ATRA promotes accessibility of FoxP3. In the next three (RORc IL-17A, and TL-6RA), if you zoom in you can see the green peaks are much larger (some are so large they get cut off), indicating that those sites, corresponding to pro-inflammatory gene regions, are much more accessible.

REFERENCES

1. Hinze C, Gohar F, Foell D. Management of juvenile idiopathic arthritis: hitting the target. *Nature Reviews Rheumatology* 2015; 11(5):290.
2. Aletaha D, Smolen J S. Diagnosis and management of rheumatoid arthritis: a review. *Jama.* 2018; 320(13):1360-72.
3. Taylor P C, Moore A, Vasilescu R, Alvir J, Tarallo M. A structured literature review of the burden of illness and unmet needs in patients with rheumatoid arthritis: a current perspective. *Rheumatology International.* 2016; 36(5):685-95. doi: 10.1007/s00296-015-3415-x. PubMed PMID: WOS:000374567500010.
4. Allen R, Chizari S, Ma J A, Raychaudhuri S, Lewis J S, Combinatorial, Microparticle Based Delivery of Immune Modulators Reprograms the Dendritic Cell Phenotype and Promotes Remission of Collagen-Induced Arthritis in Mice. *ACS Applied Bio Materials.* 2019; 2(6):2388-404.
5. Benham H, Ncl H J, Law S C, Mehdi A M, Street S, Ramnoruth N, Pahau H, Lee B T, Ng J. Brunck M E. Citrullinated peptide dendritic cell immunotherapy in HLA risk genotype-positive rheumatoid arthritis patients. *Science translational medicine.* 2015; 7(290):290ra87-ra87.
6. Raffin C, Zhou Y, Piccoli L, Lanzavecchia A, Sadelain M, Bluestone J A. Development of citrullinated-vimentin-specific CAR for targeting Tregs to treat autoimmune rheumatoid arthritis. *Am Assoc Immnol;* 2016.
7. Yuba E, Budina E, Katsumata K, Ishihara A, Mansurov A, Alpar A T, Watkins E A, Hosseinchi P, Reda J W, Lauterbach A L. Enhanced lymph node trafficking of 39 engineered IL-10 suppresses rheumatoid arthritis in murine models. *Arthritis & Rheumatology,* 2020.
8. Hughes C. Sette A. Seed M, D'Acquisto F, Manzo A. Vincent T L, Lim N H, Nissim A. Targeting of viral interleukin-10 with an antibody fragment specific to damaged arthritic cartilage improves its therapeutic potency. *Arthritis research & therapy.* 2014; 16(4):1-11.

9. Katsumata K, Ishihara J, Mansurov A. Ishihara A, Raczy M M, Yuba E, Hubbell J A. Targeting inflammatory sites through collagen affinity enhances the therapeutic efficacy of anti-inflammatory antibodies. *Science advances.* 2019; 5(11):eaay 1971.

10. Katsumata K, Ishihara J, Fukunaga K, Ishihara A, Yuba E, Budina E, Hubbell J A. Conferring extracellular matrix affinity enhances local therapeutic efficacy of anti-40 TNF-α antibody in a murine model of rheumatoid arthritis. *Arthritis research & therapy,* 2019; 21(1):1-10.

11. Cope A, Schulze-Koops H, Aringer M. The central role of T cells in rheumatoid arthritis. *Clinical and experimental rheumatology.* 2007; 25(5):S4.

12. Noack M, Miossec P. Th17 and regulatory T cell balance in autoimmune and inflammatory diseases. *Autoimmunity reviews.* 2014; 13(6):668-77.

13. Pandiyan P, Zhu J. Origin and functions of pro-inflammatory cytokine producing Foxp3+ regulatory T cells. *Cytokine.* 2015; 76(1):13-24.

14. Kimura A, Kishimoto T. IL-6: regulator of Treg/Th17 balance *European journal of immnnology.* 2010; 40(7): 1830-5.

15. Firestein G S. Rheumatoid arthritis in a mouse? *Nature Clinical Practice Rheumatology.* 2009; 5(1):1-.

16. Sakaguchi S. Takahashi T, Hata H, Nomura T, Sakaguchi N. SKG mice, a new genetic model of rheumatoid arthritis. *Arthritis Res Ther.* 2003; 5(3):1-54.

17. Sakaguchi S, Takahashi T, Hata H, Yoshitomi H, Tanaka S, Hirota K, Nomura T, Sakaguchi N. SKG mice, a monogenic model of autoimmune arthritis due to altered signal transduction in T-cells. *The Hereditary Basis of Rheumatic Diseases: Springer.* 2006. p. 147-59.

18. Sakaguchi N, Takahashi T, Hata H, Nomura T, Tagami T, Yamazaki S, Sakihama T, Matsutani T, Negishi I, Nakatsuru S. Altered thymic T-cell selection due to a mutation of the ZAP-70 gene causes autoimmune arthritis in mice. *Nature.* 2003; 426(6965):454-60.

19. Sakaguchi N, Takahashi T, Hata H, Nomura T, Tagami T, Yamazaki S, Sakihama T, Matsurtani T, Negishi 1, Nakatsuru S, Sakaguchi S, Altered thymic T-cell selection 41 due to a mutation of the ZAP-70 gene causes autoimmune arthritis in mice. *Nature.* 2003; 426(6%5):454-60. doi: 10.1038/nature02119. PubMed PMID: WOS: 000186800800041.

20. Henderson L A, Hoyt K J, Lee P Y, Rao D A, Jonsson A H, Nguyen J P, Rutherford K, Julé A M, Charbonnier L-M, Case S. Th17 reprogramming of T cells in systemic juvenile idiopathic arthritis. *JCI insight.* 2020; 5(6).

21. Svensson M N. Doody K M, Schmiedel B J, Bhattacharyya S, Panwar B, Wiede F, Yang S, Santelli E. Wu D J. Sacchetti C. Reduced expression of phosphatase PTPN2 promotes pathogenic conversion of Tregs in autoimmunity. *The Journal of clinical investigation.* 2019; 129(3): 1193-210.

22. Hsieh W-C, Svensson M N, Zoccheddu M. Tremblay M L, Sakaguchi S, Stanford S M. Bottini N. PTPN2 links colonic and joint inflammation in experimental autoimmune arthritis. *JCI insight.* 2020; 5(20)

23. Sprouse M L. Bates N A, Felix K M, Wu H J J. Impact of gut microbiota on gut-distal autoimmunity: a focus on T cells. *Immunology.* 2019; 156(4):305-18.

24. Zaiss M M., Wu H-J J, Mauro D, Schett G, Ciccia F. The gut joint axis in rheumatoid arthritis. *Nature Reviews Rheumatology.* 2021; 17(4):224-37.

25. Nozaki Y, Yamagata T, Sugiyama M, Ikoma S, Kinoshita K, Funauchi M. Antiinflammatory effect of all-trans-retinoic acid in inflammatory arthritis. *Clinical Immunology.* 2006; 119(3):272-9.

26. Elias K M, Laurence A. Davidson T S, Stephens G, Kanno Y, Shevach E M, O'Shea J J. Retinoic acid inhibits Th17 polarization and enhances FoxP3 expression through a 42 Stat-3/Stat-5 independent signaling pathway. *Blood, The Journal of the American Society of Hematology.* 2008; 111(3):1013-20.

27. Kwok S-K. Park M-K, Cho M-L, Oh H-J, Park E-M, Lee D-G, Lee J, Kim H-Y, Park S-H. Retinoic acid attenuates rheumatoid inflammation in mice. *The Journal of Immunology.* 2012; 189(2):1062-71.

28. Hurtig M, Zaghoul I, Sheardown H, Schmidt T A, Liu L, Zhang L, Elsaid K A, Jay G D. Two compartment pharmacokinetic model describes the intra-articular delivery and retention of rhprg4 following ACL transection in the Yucatan mini pig. *Journal of Orthopaedic Research®.* 2019; 37(2):386-96.

29. Jing J, Nelson C, Paik J, Shirasaka Y, Amory J K, Isoherranen N, Physiologically based pharmacokinetic model of all-trans-retinoic acid with application to cancer populations and drug interactions. *Journal of Pharmacology and Experimental Therapeutics.* 2017; 361(2):246-58.

30. Hayer S, Vervoordeldonk M J, Denis M C. Armaka M, Hoffmann M. Bäcklund J, Nandakumar K S, Niederreiter B, Geka C, Fischer A. 'SMASH' recommendations for standardised microscopic arthritis scoring of histological sections from inflammatory arthritis animal models. *Annals of the Rheumatic Diseases.* 2021; 80(6):714-26.

31. Mucida D, Park Y, Kim G, Turovskaya O, Scott I, Kronenberg M, Cheroutre H. Reciprocal TH17 and regulatory T cell differentiation mediated by retinoic acid. *Science.* 2007; 317(5835):256-60.

32. Xiao S, Jin H, Kom T, Liu S M, Oukka M, Lim B, Kuchroo V K, Retinoic acid increases Foxp3+ regulatory T cells and inhibits development of Th17 cells by 43 enhancing TGF-β-driven Smad3 signaling and inhibiting IL-6 and IL-23 receptor expression. *The Journal of Immunology.* 2008; 181(4):2277-84.

33. Bai A, Lu N, Guo Y, Liu Z, Chen J, Peng Z. All-trans retinoic acid down-regulates inflammatory responses by shifting the Treg/Th17 profile m human ulcerative and murine colitis. *Journal of leukocyte biology.* 2009; 86(4): 959-69.

34. Bird H, Moll J, Rushton A. *Therapeutics in rheumatology: Springer;* 2013.

35. Hata H, Sakaguchi N, Yoshitomi H, Iwakura Y, Sekikawa K, Azuma Y, Kanai C, Moriizumi E, Nomura T, Nakamura T. Distinct contribution of IL-6, TNF-α, IL-1, and IL-10 to T cell-mediated spontaneous autoimmune arthritis in mice. *The Journal of Clinical Investigation.* 2004; 114(4):582-8.

36. Lu L, Lan Q, Li Z, Zhou X, Gu J, Li Q, Wang J, Chen M, Liu Y, Shen Y. Critical role of all-trans retinoic acid in stabilizing human natural regulatory T cells under inflammatory conditions. *Proceedings of the National Academy of Sciences.* 2014; 111(33):E3432-E40.

37. Nagate T, Kawai J, Nakayama J. Therapeutic and preventive effects of methotrexate on zymosan-induced arthritis in SKG mice. *Journal of Veterinary Medical Science.* 2009; 71(6):713-7.

38. Kim W U, Lee W K, Ryoo J W, Kim S H, Kim J, Youn J, Min S Y, Bae E Y, Hwang S Y, Park S H. Suppression of collagen-induced arthritis by single administration of poly (lactic-co-glycolic acid) nanoparticles entrapping type II collagen: a novel treatment 44 strategy for induction of oral tolerance. *Arthritis & Rheumatism: Official Journal of the American College of Rheumatology.* 2002; 46(4):1109-20.
39. Bassin E J, Buckley A R, Piganelli J D, Little S R. TRI microparticles prevent inflammatory arthritis in a collagen-induced arthritis model. *PloS one.* 2020; 15(9): e0239396.
40. Jhunjhunwala S, Balmert S C, Raimondi G, Dons E, Nichols E E, Thomson A W, Little S R. Controlled release formulations of IL-2, TGF-β1 and rapamycin for the induction of regulatory T cells. *J Control Release.* 2012; 159(1):78-84.
41. Liang D, Zuo A, Shao H, Born W K, O'Brien R L, Kaplan H I, Sun D. Retinoic acid inhibits CD25+ dendritic cell expansion and γδ T-cell activation in experimental autoimmune uveitis. *Investigative ophthalmology & visual science,* 2013; 54(5):3493-503.
42. Abtahi Froushani S M, Delirezh N, Hobbenaghi R, Mosayebi G. Synergistic effects of atorvastatin and all-trans retinoic acid in ameliorating animal model of multiple sclerosis. *Immunological investigations.* 2014; 43(1):54-68.
43. Kurtz P J, Emmerling D C, Donofrio D J. Subchronic toxicity of all-trans-retinoic acid and retinyhdene dimedone in Sprague-Dawley rats. *Toxicology.* 1984; 30(2): 115-24.
44. Snyder J M, Zhong G, Hogarth C, Huang W, Topping T, LaFrance J, Palau L, Czuba L C, Griswold M, Ghiaur G. Knockout of Cyp26a1 and Cyp26b1 during postnatal life 45 causes reduced lifespan, dermatitis, splenomegaly, and systemic inflammation in mice. *The FASEB Journal.* 2020; 34(12):15788-804.
45. Choi Y, Lee C, Park K, Kim S Y, Kim S H, Han S, Kim S H, Byun Y. Subacute toxicity of all-trans-retinoic acid loaded biodegradable microspheres in rats. *Drug development research.* 2003; 59(3):326-32.
46. Zhu L, Chanalaris A, Lympany S, Vincent T. Cartilage injury regulates inflammatory gene expression in part by suppressing cellular retinoic acid signaling. *Osteoarthritis and Cartilage.* 2017; 25:S168.
47. Kanneganti K, Simon L. Two-compartment pharmacokinetic models for chemical engineers. *Chemical Engineering Education.* 2011; 45(2):101-5.
48. van Beuningen H M, van der Kraan P M, Amtz O J, van den Berg W B. Transforming growth factor-beta 1 stimulates articular chondrocyte proteoglycan synthesis and induces osteophyte formation in the murine knee joint. *Lab Invest.* 1994 August:71(2):279-90
49. Cooper W O, Fava R A, Gates C A, Cremer M A, Townes A S. Acceleration of onset of collagen-induced arthritis by intra-articular injection of tumour necrosis factor or transforming growth factor-beta. *Clin Exp Immunol.* 1992; 89(2):244-250.
50. Huber, Samuel, and Christoph Schramm. "TGF-beta and CD4+CD25+ regulatory T cells." *Front Biosci.* 11.1 (2006): 1014-1023.
51. Aarts, et. al., Local inhibition of TGF-β1 signaling improves Th17/Treg balance but not joint pathology during experimental arthritis. *Scientific Reports.* 2022 February; 12: 3182.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements are intended to describe and summarize various embodiments of the invention according to the foregoing description in the specification.

Statements:

1. A method for treating inflammatory arthritis in a patient, comprising: administering directly into an inflammatory arthritis-affected joint or a draining lymph node of the arthritis-affected joint of the patient a composition comprising:
   a regulatory T cell ($T_{reg}$)-inducer at least partially encapsulated in a biodegradable microparticle, wherein the biodegradable microparticle does not comprise TGF-β.
2. The method of statement 1, wherein the joint is not actively inflamed by the inflammatory arthritis.
3. The method of statement 1, wherein the patient is in remission for the inflammatory arthritis.
4. The method of statement 1, wherein the patient is in a pre-symptomatic phase of the inflammatory arthritis
5. The method of statement 1, wherein the biodegradable microparticle comprises a biodegradable polymer.
6. The method of statement 5, wherein the polymer is poly (D,L-lactide-co-glycolide).
7. The method of statement 1, wherein the $T_{reg}$-inducer induces FOXP3 expression in naïve CD4+ T cells.
8. The method of statement 7, wherein the $T_{reg}$-inducer is a retinoic acid receptor (RAR) agonist.
9. The method of statement 8, wherein the RAR agonist is all trans retinoic acid (ATRA).
10. The method of statement 1, wherein the $T_{reg}$-inducer induces IL-10 expression in naïve CD4+ T cells.
11. The method of statement 1, wherein the composition further comprises a disease modifying anti-rheumatic drug (DMARD), wherein the DMARD is encapsulated within the microparticle.
12. The method of statement 1, further comprising administering a disease modifying anti-rheumatic drug (DMARD) to the patient.
13. The method of statement 12, wherein the DMARD is administered orally, subcutaneously, or intravenously to the patient.
14. The method of statement 9, wherein the microparticles comprise about 1 weight percent to about 5 weight percent ATRA.
15. The method of statement 1, wherein the biodegradable microparticles are approximately 5 µm up to approximately 20 µm in diameter.
16. The method of statement 1, wherein the biodegradable microparticles are approximately 20 µm up to approximately 50 µm in diameter.
17. The method of statements 11 or 12, wherein the combination of the $T_{reg}$-inducer and DMARD synergistically reduce inflammation or bone loss in the inflammatory arthritis-affected joint.
18. The method of statement 1, wherein the composition stabilizes a population of $T_{reg}$ cells within the inflammatory arthritis-affected joint and at least one other inflamed joint when the composition is administered into at least one of the inflammatory arthritis-affected joint directly by intra-articular injection, the draining lymph node of the inflammatory arthritis-affected joint, a subcutaneous tissue in the vicinity of the inflammatory arthritis-affected joint, or a joint capsule of the inflammatory arthritis-affected joint of the patient.

19. The method of statement 1 wherein the composition enhances systemic production of anti-inflammatory cytokines in the patient.

20. The method of statement 1, wherein the composition increases a ratio of $T_{reg}$ cells to dysfunctional $T_{reg}$ cells within the inflammatory arthritis-affected joint when the composition is administered directly into the inflammatory arthritis-affected joint by intra-articular injection or into the draining lymph node associated with the inflammatory arthritis-affected joint.

21. The method of statement 20, wherein the dysfunctional $T_{reg}$ cells comprise pro-inflammatory $T_{reg}$ phenotype T cells.

22. The method of statement 20, wherein the dysfunctional $T_{reg}$ cells comprise Th17-like ex$T_{reg}$ phenotype T cells.

23. The method of statement 56, wherein the dysfunctional $T_{reg}$ cells comprise Th1-like ex$T_{reg}$ phenotype T cells.

24. The method of statements 9 and 14, wherein approximately 2 μg to approximately 20 μg of the composition is administered directly into the inflammatory arthritis-affected joint or the draining lymph node associated with the inflammatory arthritis-affected joint.

25. The method of statements 9 and 14, wherein approximately 2 μg up to approximately 200 μg of the composition is administered directly into the inflammatory arthritis-affected joint or the draining lymph node associated with the inflammatory arthritis-affected joint.

26. The method of statements 9 and 14, wherein a dose of the composition administered is sufficient to stabilize a population of $T_{reg}$ cells within the inflammatory arthritis-affected joint and does not cause systemic immunosuppression of the patient.

27. The method of statements 9 and 14, wherein a dose of the composition administered is sufficient to increase a ratio of $T_{reg}$ cells to dysfunctional $T_{reg}$ cells within the inflammatory arthritis-affected joint and does not cause systemic immunosuppression of the patient.

28. The method of statement 1, wherein the composition reduces a severity of inflammation or bone loss in at least one other inflammatory arthritis-affected joint of the patient into which the composition was not directly administered.

29. The method of statement 1, wherein the composition does not cause systemic immunosuppression of the patient.

30. The method of statement 1, wherein the biodegradable microparticle provides for sustained or extended release of the $T_{reg}$-inducer for a time sufficient to reduce inflammation or bone loss in the inflammatory arthritis-affected joint and at least one other inflammatory arthritis-affected joint of the patient into which the composition was not directly administered.

31. The method of statement 30, wherein the biodegradable microparticle sustains a continuous release of the $T_{reg}$-inducer in the inflammatory arthritis-affected joint of the patient for at least 21 days.

32. The method of statement 30, wherein the biodegradable microparticle sustains a continuous release of the $T_{reg}$-inducer in the inflammatory arthritis-affected joint of the patient for approximately three months.

33. The method of statements 1 or 30, wherein the biodegradable microparticle is resistant to phagocytosis by macrophages or escape from the inflammatory arthritis-affected joint or the draining lymph node that the biodegradable microparticle was directly administered into.

34. The method of statement 1, wherein the $T_{reg}$-inducer induces differentiation of naïve T cells into $T_{reg}$ cells.

35. The method of statement 1, wherein the biodegradable microparticle does not have TGF-β adsorbed onto the surface of the microparticle.

36. A method for treating an inflammatory arthritic condition in a patient, comprising:
    locally administering into at least one of an inflammatory arthritis-affected joint, a draining lymph node of the inflammatory arthritis-affected joint, a subcutaneous tissue in the vicinity of the inflammatory arthritis-affected joint, or a joint capsule of the inflammatory arthritis-affected joint of the patient a composition comprising:
        an immunomodulatory agent that modifies the microenvironment in the inflammatory arthritis-affected joint and systemically affects at least one other inflamed joint.

37. The method of statement 36, wherein the immunomodulatory agent comprises a regulatory T-cell ($T_{reg}$)-inducer at least partially encapsulated in a biodegradable material, wherein the biodegradable microparticle does not comprise TGF-β.

38. The method of statement 36, wherein the immunomodulatory agent comprises a synovial fibroblast modulator at least partially encapsulated in a biodegradable material, and wherein the agent does not comprise TGF-β.

39. The method of statement 36, wherein the immunomodulatory agent comprises an antigen presenting cell modulator at least partially encapsulated in a biodegradable material, and wherein the agent does not comprise TGF-β.

40. The method of statement 36, wherein the patient is in remission for the inflammatory arthritis.

41. The method of statement 36, wherein the patient is in a pre-symptomatic phase of the inflammatory arthritis 42. The method of statements 37, 38, or 39, wherein the biodegradable material comprises a biodegradable polymer.

43. The method of statement 42, wherein the biodegradable polymer is poly (D,L-lactide-co-glycolide).

44. The method of statement 37, wherein the $T_{reg}$-inducer induces FOXP3 expression in naïve CD4+ T cells.

45. The method of statement 36, wherein the $T_{reg}$-inducer induces IL-10 expression in naïve CD4+ T cells.

46. The method of statement 44, wherein the $T_{reg}$-inducer is a retinoic acid receptor (RAR) agonist 47. The method of statement 46, wherein the RAR agonist is all trans retinoic acid (ATRA).

48. The method of statements 37, 38, or 39, wherein the composition further comprises a disease modifying anti-rheumatic drug (DMARD), wherein the DMARD is encapsulated within the microparticle.

49. The method of statements 37, 38, or 39, further comprising administering a disease modifying anti-rheumatic drug (DMARD) to the patient.

50. The method of statement 49, wherein the DMARD is administered orally, subcutaneously, or intravenously to the patient.

51. The method of statement 47, wherein the microparticles comprise about 1 weight percent to about 5 weight percent ATRA.

52. The method of statements 37, 38, or 39, wherein the microparticles are approximately 5 μm up to approximately 20 μm in diameter.
53. The method of statements 37, 38, or 39, wherein the biodegradable microparticles are approximately 20 μm up to approximately 50 μm in diameter.
54. The method of statements 48 or 49, wherein the combination of the $T_{reg}$-inducer and DMARD synergistically reduce inflammation or bone loss in the inflammatory arthritis-affected joint.
55. The method of statement 36, wherein the immunomodulatory agent stabilizes a population of $T_{reg}$ cells within the inflammatory arthritis-affected joint and at least one other inflamed joint.
56. The method of statement 36, wherein the immunomodulatory agent enhances systemic production of anti-inflammatory cytokines in the patient.
57. The method of statement 36, wherein the immunomodulatory agent increases a ratio of $T_{reg}$ cells to dysfunctional $T_{reg}$ cells within the inflammatory arthritis-affected joint.
58. The method of statement 57, wherein the dysfunctional $T_{reg}$ cells comprise pro-inflammatory $T_{reg}$ phenotype T cells
59. The method of statement 57, wherein the dysfunctional $T_{reg}$ cells comprise Th17-like ex$T_{reg}$ phenotype T cells.
60. The method of statement 57, wherein the dysfunctional $T_{reg}$ cells comprise Th1-like ex$T_{reg}$ phenotype T cells.
61. The method of statements 47 or 51, wherein approximately 2 μg to approximately 20 μg of the immunomodulatory agent is locally administered.
62. The method of statements 47 or 51, wherein approximately 2 μg up to approximately 200 μg of the immunomodulatory agent is locally administered.
63. The method of statements 47 or 51, wherein a dose of the immunomodulatory agent administered to the patient is sufficient to stabilize a population of $T_{reg}$ cells within the inflammatory arthritis-affected joint and does not cause systemic immunosuppression of the patient.
64. The method of statements 47 or 51, wherein a dose of the immunomodulatory agent administered to the patient is sufficient to increase a ratio of $T_{reg}$ cells to dysfunctional $T_{reg}$ cells within the inflammatory arthritis-affected joint and does not cause systemic immunosuppression of the patient.
65. The method of statement 36, wherein the immunomodulatory agent reduces a severity of inflammation or bone loss in at least one other inflammatory arthritis-affected joint of the patient into which the immunomodulatory agent was not directly administered.
66. The method of statement 36, wherein the composition does not cause systemic immunosuppression of the patient.
67. The method of statement 37, wherein the biodegradable microparticle provides for sustained or extended release of the $T_{reg}$-inducer for a time sufficient to reduce inflammation or bone loss in the inflammatory arthritis-affected joint and at least one other inflammatory arthritis-affected joint of the patient into which the composition was not directly administered.
68. The method of statement 67, wherein the biodegradable microparticle sustains a continuous release of the $T_{reg}$-inducer in the inflammatory arthritis-affected joint of the patient for at least 21 days.
69. The method of statement 67, wherein the biodegradable microparticle sustains a continuous release of the $T_{reg}$-inducer in the inflammatory arthritis-affected joint of the patient for approximately three months.
70. The method of statements 37, 38, or 39, wherein the biodegradable microparticle is resistant to phagocytosis by macrophages or escape from the inflammatory arthritis-affected joint or the draining lymph node that the biodegradable microparticle was directly administered into.
71. The method of statement 37, wherein the $T_{reg}$-inducer induces differentiation of naïve T cells into $T_{reg}$ cells.
72. The method of statements 37, 38, or 39, wherein the biodegradable microparticle does not have TGF-β adsorbed onto the surface of the microparticle.
73. A method for treating inflammatory arthritis in a patient, comprising:
    administering directly into an inflammatory arthritis-affected joint or a draining lymph node of the inflammatory arthritis-affected joint of the patient a composition consisting essentially of:
    a regulatory T cell ($T_{reg}$)-inducer at least partially encapsulated in a biodegradable microparticle.

The specific methods, devices and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications can be made to the invention disclosed herein without departing from the scope and spirit of the invention.

The invention illustratively described herein suitably can be practiced in the absence of any element or elements, or limitation or limitations, which is not specifically disclosed herein as essential. The methods and processes illustratively described herein suitably can be practiced in differing orders of steps, and the methods and processes are not necessarily restricted to the orders of steps indicated herein or in the claims.

Under no circumstances can the patent be interpreted to be limited to the specific examples or embodiments or methods specifically disclosed herein. Under no circumstances can the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed can be resorted to by those skilled in the art, and that such modifications and variations are considered to be within the scope of this invention as defined by the appended claims and statements of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

What is claimed:

1. A method for treating inflammatory arthritis in local and distal joints in a patient, comprising:
    administering a composition directly into an inflammatory arthritis-affected joint or into a draining lymph node associated with the inflammatory arthritis-affected joint of the patient, wherein the composition comprises all trans retinoic acid (ATRA) at least partially encapsulated in biodegradable microparticles;
    wherein the composition administered directly into the joint or draining lymph node associated therewith reduces severity of inflammation or bone loss in at least one other inflammatory arthritis-affected joint of the patient into which the composition was not administered directly or into the draining lymph node associated therewith; and
    wherein a maximum peripheral blood concentration of the ATRA released from the microparticles is below 100 pM.

2. The method of claim 1, wherein the biodegradable microparticles provide sustained release of the ATRA in the injected joint after intra-articular administration.

3. The method of claim 2, wherein the biodegradable microparticles comprise one or more biodegradable polymers.

4. The method of claim 3, wherein the biodegradable polymer comprises poly(lactic-co-glycolic) acid (PLGA).

5. The method of claim 1, wherein the ATRA is approximately 1 wt. % to approximately 30 wt. % of the biodegradable microparticles.

6. The method of claim 1, wherein the biodegradable microparticles have an average diameter of approximately 5 µm to approximately 50 µm.

7. The method of claim 1, wherein approximately 0.08 mg/kg up to approximately 8 mg/kg of the composition is administered.

8. The method of claim 1, wherein approximately 0.02 µg up to approximately 2 µg of the ATRA is administered.

9. The method of claim 1, wherein the injected joint or associated draining lymph node is not actively inflamed, wherein the patient has active inflammation in other non-injected joints, wherein the patient is in at least partial remission for the inflammatory arthritis, and/or wherein the patient is in a pre-symptomatic phase of the inflammatory arthritis.

10. The method of claim 1, wherein the composition reduces inflammation and/or bone loss in the inflammatory arthritis-affected joint.

11. The method of claim 10, wherein the ATRA directly induces local expansion and stabilization of $T_{reg}$ cells in the inflammatory arthritis-affected joint or associated draining lymph node.

12. The method of claim 11, wherein the $T_{reg}$ cells expanded and stabilized in the inflammatory arthritis-affected joint or associated draining lymph node recirculate to at least one other inflammatory arthritis-affected joint, and wherein the $T_{reg}$ cells reduce the severity of the inflammation or bone loss in joints into which they recirculate.

13. The method of claim 1, wherein the reduction in inflammation and/or bone loss in the both the injected and non-injected joints continues for at least 2 months after biodegradation of the composition in the injected joint or associated draining lymph node.

14. The method of claim 2, wherein the biodegradable microparticles sustain a continuous release of the ATRA in the inflammatory arthritis-affected joint of the patient for at least 21 days.

15. The method of claim 1, wherein a release profile of the ATRA from the microparticles in the injected joint or associated draining lymph node is insufficient to cause systemic exposure of the ATRA above a generalized immunosuppressive threshold.

16. The method of claim 1, wherein the composition does not comprise TGF-β.

17. The method of claim 1, wherein the maximum peripheral blood concentration of the ATRA released from the microparticles is below 20 pM.

18. The method of claim 1, wherein the maximum peripheral blood concentration of the ATRA released from the microparticles is below 40 pM.

19. A method for treating inflammatory arthritis in local and distal joints of a patient, comprising:
    administering a composition directly into an inflammatory arthritis-affected joint or into a draining lymph node associated with the inflammatory arthritis-affected joint of the patient, wherein the composition comprises all trans retinoic acid (ATRA) at least partially encapsulated in biodegradable microparticles;
    wherein the composition administered directly into the joint or draining lymph node associated therewith reduces severity of inflammation or bone loss in at least one other inflammatory arthritis-affected joint of the patient into which the composition was not administered directly or into the draining lymph node associated therewith; and
    wherein the composition administered directly into the joint or draining lymph node associated therewith comprises 0.02 µg up to 2 µg of ATRA in the composition.

20. A method for treating inflammatory arthritis in local and distal joints of a patient, comprising:
    administering a composition directly into an inflammatory arthritis-affected joint or into a draining lymph node associated with the inflammatory arthritis-affected joint of the patient, wherein the composition comprises all trans retinoic acid (ATRA) at least partially encapsulated in biodegradable microparticles;
    wherein the composition administered directly into the joint or draining lymph node associated therewith reduces severity of inflammation or bone loss in at least one other inflammatory arthritis-affected joint of the patient into which the composition was not administered directly or into the draining lymph node associated therewith; and
    wherein the composition provides sustained release of the ATRA at therapeutically relevant concentrations in only the joint into which the composition was administered and not into the at least one other inflammatory arthritis-affected joint.

* * * * *

UNITED STATES PATENT AND TRADEMARK OFFICE
CERTIFICATE OF CORRECTION

| | |
|---|---|
| PATENT NO. | : 12,201,598 B2 |
| APPLICATION NO. | : 18/474108 |
| DATED | : January 21, 2025 |
| INVENTOR(S) | : Shah et al. |

It is certified that error appears in the above-identified patent and that said Letters Patent is hereby corrected as shown below:

In the Specification

Column 1, Lines 16-21, please replace the paragraph under the FEDERAL FUNDING from "This invention was made with government support under F31AR079921, T32AR064194, T32CA153915, P30AR073761, R03DE031009, P30CA23100, and UL1TR001442 awarded by the National Institutes of Health and ECCS-2025752 awarded by the National Science Foundation. The government has certain rights in the invention." to --This invention was made with government support under AR079921, AR064194, CA0153915, AR073761, DE031009, CA023100, and TR001442 awarded by National Institutes of Health and under CCS-10 2025752 awarded by the National Science Foundation. The government has certain rights in the invention.--

Signed and Sealed this
Twenty-fifth Day of November, 2025

John A. Squires
*Director of the United States Patent and Trademark Office*